(12) United States Patent
Fujita et al.

(10) Patent No.: US 8,603,001 B2
(45) Date of Patent: Dec. 10, 2013

(54) DEVICE AND COMPUTER PROGRAM FOR ANALYZING BIOLOGICAL BODY STATE

(75) Inventors: Etsunori Fujita, Hiroshima (JP); Yumi Ogura, Hiroshima (JP); Shinichiro Maeda, Hiroshima (JP); Shigeyuki Kojima, Hiroshima (JP)

(73) Assignee: Delta Tooling Co., Ltd., Hiroshima-shi (JP)

( * ) Notice: Subject to any disclaimer, the term of this patent is extended or adjusted under 35 U.S.C. 154(b) by 104 days.

(21) Appl. No.: 13/266,188

(22) PCT Filed: Apr. 24, 2010

(86) PCT No.: PCT/JP2010/057299
§ 371 (c)(1),
(2), (4) Date: Dec. 1, 2011

(87) PCT Pub. No.: WO2010/123125
PCT Pub. Date: Oct. 28, 2010

(65) Prior Publication Data
US 2012/0101395 A1    Apr. 26, 2012

(30) Foreign Application Priority Data

Apr. 25, 2009  (JP) ................................ 2009-107197

(51) Int. Cl.
*A61B 5/02* (2006.01)
*A47C 3/00* (2006.01)

(52) U.S. Cl.
USPC .......................... 600/508; 600/509; 297/284.1

(58) Field of Classification Search
USPC ................ 600/508–509; 297/284.1
See application file for complete search history.

(56) References Cited

U.S. PATENT DOCUMENTS

| | | | |
|---|---|---|---|
| 7,250,029 B2 | 7/2007 | Fujita et al. | |
| 7,470,231 B2 | 12/2008 | Fujita et al. | |
| 7,496,457 B2 | 2/2009 | Fujita et al. | |
| 7,532,964 B2 | 5/2009 | Fujita et al. | |
| 2005/0065663 A1 | 3/2005 | Oyama | |
| 2010/0117411 A1 | 5/2010 | Fujita et al. | |
| 2011/0251522 A1 | 10/2011 | Fujita et al. | |

FOREIGN PATENT DOCUMENTS

| | | |
|---|---|---|
| JP | 2005 71184 | 3/2005 |
| JP | 2006 149470 | 6/2006 |
| JP | 2008 194321 | 8/2008 |

OTHER PUBLICATIONS

International Search Report Issued Aug. 17, 2010 in PCT/JP10/057299 filed Apr. 24, 2010.
U.S. Appl. No. 13/321,367, filed Nov. 18, 2011, Fujita, et al.

*Primary Examiner* — Nicole F Lavert
(74) *Attorney, Agent, or Firm* — Oblon, Spivak, McClelland, Maier & Neustadt, L.L.P.

(57) ABSTRACT

A state change of a person is captured with timing closer to consciousness of the person. A frequency slope waveform of a time series signal of a pulse wave of a body of a person detected by an air pack is obtained by a frequency slope time-series analyzing and a computing device and a frequency fluctuation time-series waveform is obtained by a frequency fluctuation time-series analyzing and computing device. By comparing changes of two waveforms with each other in a waveform determining device, a state change of a person can be captured with timing closer to consciousness of the person.

25 Claims, 34 Drawing Sheets

DEVICE AND COMPUTER PROGRAM FOR ANALYZING BIOLOGICAL BODY STATE

TECHNICAL FIELD

The present invention relates to a technique for analyzing a state of a biological body using a time-series waveform of a biological signal obtained from an upper body of a person.

BACKGROUND ART

Monitoring a biological body state of a driver during driving has attracted attention as a preventive measure against an accident or the like in recent years. The present applicant disclosed techniques of disposing a pressure sensor in a seat cushion section, obtaining and analyzing breech pulse waves, and determining a sleep prediction phenomenon in Patent Literatures 1 to 3.

Specifically, a maximum value and a minimum value of a time-series waveform of a breech pulse wave are obtained by a smoothing differentiation method of Savitzky and Golay, respectively. The maximum value and the minimum value are obtained for each 5 seconds so that their mean values are obtained. Using a square of a difference between the respective mean values of the maximum values and the minimum values obtained as a power value, the power value is plotted for each 5 seconds so that a time-series waveform of the power value is produced. In order to read a global change of the power value from this time-series waveform, a slope of the power value regarding a certain time window Tw (180 seconds) is obtained by least-square method. Next, the slope regarding the next time window Tw is similarly calculated in an overlapped time TI (162 seconds) and the calculation results are plotted. A time-series waveform of the slope of the power value is obtained by repeating this calculation (movement calculation) sequentially. On the other hand, the maximum Lyapunov exponent is obtained by applying Chaos analysis to the time-series waveform of the pulse wave, a maximum value is obtained by a smoothing differentiation like the above, and a time-series waveform of a slope of the maximum Lyapunov exponent is obtained by conducting movement calculation.

Then, the time-series waveform of the slope of the power value and the time-series waveform of the slope of the maximum Lyapunov exponent take phases opposite to each other, and a waveform having a large amplitude at a low frequency in the time-series waveform of the slope of the power value is determined as a characteristic signal indicating a sleep prediction and a point at which the amplitude has become small thereafter is determined as a sleep-onset point.

Further, as Patent Literature 4, a system provided with an airbag (air pack) including a three-dimensional solid fabric inserted therein, where the air pack is disposed at a site corresponding to a waist portion of a person, an air pressure fluctuation in the air pack is measured, a biological signal of the person is detected from the time-series waveform of the air pressure fluctuation obtained, and the biological body state of the person is analyzed is disclosed. Further, in Non-Patent Literatures 1 and 2, trials for detecting a biological signal of a person by disposing an air pack sensor along a lumber iliocostal muscle are reported. A pulse wave near a lumber area shows a circulation fluctuation of blood flowing in a descending aorta according to a heartbeat, namely, the motion of the atrium and the fluctuation of the aorta. Incidentally, in the following, a biological signal due to the motion of the atrium and the fluctuation of the aorta, which is obtained from such a dorsal region (lumbar area) is called "aortic pulse wave". A state change of a person corresponding to a heartbeat fluctuation can be captured in utilization of this aortic pulse wave more accurately than in utilizing the breech pulse wave disclosed in Patent Literatures 1 and 2.

PRIOR ART LITERATURES

Patent Literature
 Patent Literature 1: Japanese Patent Application Laid-Open No. 2004-344612
 Patent Literature 2: Japanese Patent Application Laid-Open No. 2004-344613
 Patent Literature 3: WO2005/092193A1
 Patent Literature 4: Japanese Patent Application Laid-Open No. 2007-90032
 Patent Literature 5: WO2005/039415A1
Non-Patent Literatures
 Non-Patent Literature 1: "APPLICATION OF BIOLOGICAL WANDERING SIGNAL MEASURED BY NON-INVASIVE TYPE SENSOR TO FATIGUE AND SLEEP PREDICTION" by Naoki OCHIAI (and six others), 39th Japan Ergonomics Society Chugoku and Shikoku Branch convention, Collection of Literatures and Papers issued on Nov. 25, 2006 from Japan Ergonomics Society Chugoku and Shikoku Branch Secretariat
 Non-Patent Literature 2: "TRIAL PRODUCTION OF VEHICLE SEAT HAVING NON-INVASIVE BIOLOGICAL SIGNAL SENSING FUNCTION" by Shinichiro MAEDA (and four others), 39th Japan Ergonomics Society Chugoku and Shikoku Branch Convention, Collection of Literatures and Papers issued on Nov. 25, 2006 from Japan Ergonomics Society Chugoku and Shikoku Branch Secretariat

SUMMARY OF INVENTION

Technical Problem

As described above, in the techniques described in Patent Literatures 1 to 4 and Non-Patent Literatures 1 and 2, the time where the time-series waveform of the slope of the power value and the time-series waveform of the slope of the maximum Lyapunov exponent has taken phases opposite to each other and a waveform having a large amplitude at a low frequency has occurred in the time-series waveform of the slope of the power value is regarded as the sleep prediction phenomenon. According to this method, when a person sits on a seat, the sleep prediction phenomenon can be captured. However, regarding this sleep prediction phenomenon, detection of a characteristic signal such as described above does not necessarily involve sleepiness. Of course, there is also a case where an emergence time of the sleep prediction phenomenon coincides with a timing at which a person has become conscious of sleepiness depending on a person or depending on a physical condition of a person.

For example, by combining the above-described detection of a sleep prediction signal with a system for issuing an alert by sound, tilting of a seatback section, vibrations, or the like when this signal is captured, an effect of suppressing driver's dozing can be expected. In fact, such an alert system has been developed by the present applicant and various experiments thereof have been performed, where effect of suppressing dozing have been confirmed. However, such a fact has been found that, when an alert is generated at a timing of detection of the above-described sleep prediction signal, a driver who does not feel sleepy may feel the timing of the alert too early. That is, it has been found that although the time point of occurrence of the sleep prediction signal detected by the above method is useful in effect of suppressing dozing by issuing an alert at that timing, there are cases when the timing does not match with a timing of sleepiness felt by a driver himself/herself, so that the driver feels this alert as malfunction of the apparatus. In view of these circumstances, such a driver demands a system where an alert is issued in synchronous with the timing at which a person becomes conscious of sleepiness.

On the other hand, in Patent Literature 5, the present applicant has also proposed the technique of applying absolute value processing to the time-series waveform of the slope of the power value to calculate a value of integral and obtaining a degree of fatigue from the value of integral. However, the technique described in Patent Literature 5 makes determination about only whether accumulated fatigue due to work is present or absent. When a person works for a predetermined time period, there are cases where a person works without feeling fatigue, where though fatigue is being accumulated, the fatigue is compensated by sympathetic nervous tone or the like so that the fatigue cannot be detected objectively in a short-time examination, where an error or delay of a reaction time is found due to fatigue, where a person gets sleepy, and the like. Since these phenomena emerge variously even in the same working time depending on respective persons, if it is possible to make simple determination about how respective persons changes depending on their work, improvement in work efficiency or the like can be achieved. For example, such information can be utilized for safety driving for a driver.

The present invention has been made in view of these circumstances, and a problem to be solved by the invention is to provide a technique capable of capturing a state change of a person more accurately at a timing closer to a person's consciousness. Further, another problem to be solved by the invention is to provide a technique capable of improving an effect of suppressing dozing by capturing a state change when a person becomes aware of sleepiness. Still another problem to be solved by the invention is to provide a technique of determining a person's fatigued state simply and accurately.

Solution to Problem

The present inventors have keenly studied solutions for solving the above problem, and have newly found that the fact that a state change of a person can be captured at a timing closer to consciousness of the person by utilizing a time-series waveform of a frequency fluctuation of an aortic pulse wave which is a biological signal detected from a dorsal region of the person and a frequency slope time-series waveform obtained from a time-series waveform of a frequency, which has resulted in completion of this invention.

In order to solve the above problem, the present invention is a biological body state analyzing device provided with a state analyzing section which analyzes a time-series waveform of a biological signal obtained from an upper body of a person by a biological signal measuring device to analyze a state of the person, wherein the state analyzing section comprises:

a frequency computing means which obtains a time-series waveform of a frequency in the time-series waveform of the biological signal;

a frequency slope time-series analyzing and computing means which performs movement calculation for obtaining a slope of the frequency for each predetermined time window set in a predetermined overlapped time in the time-series waveform of the frequency of the biological signal obtained by the frequency computing means to output a time series change of the slope of the frequency obtained for each time window as a frequency slope time-series waveform;

a frequency fluctuation time-series analyzing and computing means which performs movement calculation for obtaining a mean value of the frequency for each predetermined time window set in a predetermined overlapped time in the time-series waveform of the frequency of the biological signal obtained by the frequency computing means to output a time series change of the mean value of the frequency obtained for each time window as a frequency fluctuation time-series waveform; and a waveform determining means which analyzes the frequency slope time-series waveform obtained by the frequency slope time-series analyzing and computing means, the frequency fluctuation time-series waveform obtained by the frequency fluctuation time-series analyzing and computing means, and a state of change of a base line of the frequency fluctuation time-series waveform, thereby making determination.

Such a configuration is preferably adopted that the waveform determining means includes a sleep-onset point determining means which, when a fluctuation waveform steep gradient portion indicating a steep gradient change in the frequency fluctuation time-series waveform obtained by the frequency fluctuation time-series analyzing and computing means emerges, a position of the base line of the frequency fluctuation time-series waveform thereafter does not return to the position of the base line of the frequency fluctuation time-series waveform before emergence of the fluctuation waveform steep gradient portion, both the amplitude of the frequency fluctuation time-series waveform and the amplitude of the frequency slope time-series waveform after emergence of the fluctuation waveform steep gradient portion are smaller than the amplitude of the frequency fluctuation time-series waveform and the amplitude of the frequency slope time-series waveform before emergence of the fluctuation waveform steep gradient portion, and the base line of the frequency fluctuation time-series waveform after emergence of the fluctuation waveform steep gradient portion is in a lowering tendency of downward to the right, determines a terminal point of the fluctuation waveform steep gradient portion as sleep-onset point. In this case, such a configuration is preferably adopted that the sleep-onset point determining means performs comparison with teaching data of a sleepiness state leading to sleep onset, and the frequency fluctuation time-series waveform and the frequency slope time-series waveform at an occurrence time of the sleep-onset point, which are preliminarily measured, to determine emergence of the fluctuation waveform steep gradient portion.

Such a configuration is preferably adopted that the waveform determining means further includes a sleepiness waveform determining means which, when a slope line of the fluctuation waveform steep gradient portion obtained by the frequency fluctuation time-series analyzing and computing means is substantially parallel to a slope line of a slope waveform steep gradient portion in the frequency slope time-series waveform immediately before emergence of the fluctuation waveform steep gradient portion, determines a waveform at that time as a sleepiness state. In this case, such a configuration is preferably adopted that the sleepiness waveform determining means performs comparison with teaching data of a sleepiness state leading to sleep onset, and the frequency fluctuation time series analysis waveform and the frequency slope time series analysis waveform at an occurrence time of the sleep-onset point, which are preliminarily measured, to determine emergences of the fluctuation waveform steep gradient portion and the slope waveform steep gradient portion.

Such a configuration is preferably adopted that the waveform determining means further includes a fatigue state estimating means which compares the frequency slope time-series waveform obtained from the frequency slope time-series analyzing and computing means and the frequency fluctuation time-series waveform obtained from the frequency fluctuation time-series analyzing and computing means with each other to estimate a fatigue state from a degree of a difference between both the waveforms. In this case, such a configuration is preferably adopted that the fatigue state estimating means includes a means which determines a case where the frequency fluctuation time-series waveform transitions with an approximately equal amplitude at an approximately equal frequency while involving a predetermined phase delay relative to the frequency slope time-series waveform as a fatigue-free well state and estimates a fatigue state in a stepwise fashion according to whether or not a predetermined or more change occurs from the well state regarding at least one item of an initial phase angle, a phase difference, an amplitude, and an angular frequency. Also, such a configuration can be adopted that the fatigue state estimating means converts the frequency slope time-series waveform and the frequency fluctuation time-series waveform into sinusoidal models of a single harmonic motion, respectively, to perform estimation of the fatigue state between both the sinusoidal models. Further, such a configuration can be adopted that the fatigue state estimating means converts the frequency slope time-series waveform and the frequency fluctuation time-series waveform into sinusoidal models of a single harmonic motion, then synthesizes both the sinusoidal models to obtain a synthesized wave, compares the synthesized wave thus obtained with a synthesized wave obtained in a fatigue-free well state to perform estimation of a fatigue state.

Such a configuration is preferably adopted that the frequency computing means includes at least one means among a means which smoothing-differentiates the time-series waveform of the biological signal to obtain a maximum value and obtain a time-series waveform of the frequency of the biological signal using the maximum value, and a means which obtains a zero-crossing point at which a positive value changes to a negative value in the time-series waveform of the biological signal and obtains a time-series waveform of the frequency of the biological signal using the zero-crossing point.

Such a configuration can be adopted that the frequency computing means includes a first frequency computing means which smoothing-differentiates the time-series waveform of the biological signal to obtain a maximum value and obtain a time-series waveform of the frequency of the biological signal using the maximum value and a second frequency computing means which obtains a zero-crossing point at which a positive value changes to a negative value in the time-series waveform of the biological signal and obtains a time-series waveform of the frequency of the biological signal using the zero-crossing point;

the frequency slope time-series analyzing and computing means includes a first frequency slope time-series analyzing and computing means which performs movement calculation for obtaining a slope of the frequency for each predetermined time window set in a predetermined overlapped time in the time-series waveform of the frequency of the biological signal obtained by the first frequency computing means and outputs a time series change of the slope of the frequency obtained for each time window as a frequency slope time-series waveform, and a second frequency slope time-series analyzing and computing means which performs movement calculation for obtaining a slope of the frequency for each predetermined time window set in a predetermined overlapped time in the time-series waveform of the frequency of the biological signal obtained by the second frequency computing means and outputs a time series change of the slope of the frequency obtained for each time window as a frequency slope time-series waveform; and the waveform determining means includes a first integral curve computing means which applies absolute value processing to the frequency slope time-series waveform obtained by the first frequency slope time-series analyzing and computing means to integrate the same and obtain a first integral curve, a second integral curve computing means which applies absolute value processing to the frequency slope time-series waveform obtained by the second frequency slope time-series analyzing and computing means to integrate the same and obtain a second integral curve, and an integral curve determining means which compares the respective integral curves obtained by the first integral curve computing means and the second integral curve computing means, respectively, with each other. Such a configuration is preferably adopted that the integral curve determining means determines a state of a person from shape patterns of the respective integral curves.

It is preferred that the biological signal measuring device is disposed corresponding to a dorsal region of a person and is for detecting a time-series waveform of a biological signal due to movement of an atrium and fluctuation of an aorta obtained through the dorsal region, and the state analyzing section is for analyzing a state of a person using the time-series waveform of the biological signal.

Further, the present invention is also a computer program configuring a state analyzing section provided in a storage section of a biological body state analyzing device which analyzes a time-series waveform of a biological signal obtained from an upper body of a person by a biological signal measuring device to analyze a state of the person, wherein the computer program comprises:

a frequency calculating step of obtaining a time-series waveform of a frequency in a time-series waveform of the biological signal;

a frequency slope time-series analyzing and computing step of performing movement calculation for obtaining a slope of the frequency for each predetermined time window set in a predetermined overlapped time in the time-series waveform of the frequency of the biological signal obtained by the frequency computing step to output a time series change of the slope of the frequency obtained for each time window as a frequency slope time-series waveform;

a frequency fluctuation time-series analyzing and computing step of performing movement calculation for obtaining a mean value of the frequency for each predetermined time window set in a predetermined overlapped time in the time-series waveform of the frequency of the biological signal obtained by the frequency computing step to output a time series change of the mean value of the frequency obtained for each time window as a frequency fluctuation time-series waveform; and a waveform determining step of analyzing the frequency slope time-series waveform obtained at the frequency slope time-series analyzing and computing step, the frequency fluctuation time-series waveform obtained at the frequency fluctuation time-series analyzing and computing step, and a state of change of a base line of the frequency fluctuation time-series waveform, thereby making determination.

Such a configuration is preferably adopted that the waveform determining step includes a sleep-onset point determining step of, when a fluctuation waveform steep gradient portion indicating a steep gradient change in the frequency fluctuation time-series waveform obtained at the frequency fluctuation time-series analyzing and computing step emerges, a position of the base line of the frequency fluctuation time-series waveform thereafter does not return to the position of the base line of the frequency fluctuation time-series waveform before emergence of the fluctuation waveform steep gradient portion, both the amplitude of the frequency fluctuation time-series waveform and the amplitude of the frequency slope time-series waveform after emergence of the fluctuation waveform steep gradient portion are smaller than the amplitude of the frequency fluctuation time-series waveform and the amplitude of the frequency slope time-series waveform before emergence of the fluctuation waveform steep gradient portion, and the base line of the frequency fluctuation time-series waveform after emergence of the fluctuation waveform steep gradient portion is in a lowering tendency of downward to the right, determining a terminal point of the fluctuation waveform steep gradient portion as a sleep-onset point. In this case, such a configuration is preferably adopted that the sleep-onset point determining step performs comparison with teaching data of a sleepiness state leading to sleep onset, and the frequency fluctuation time-series waveform and the frequency slope time-series waveform at an occurrence time of the sleep-onset point, which are preliminarily measured, to determine emergence of the fluctuation waveform steep gradient portion.

Such a configuration is preferably adopted that the waveform determining step further includes a sleepiness waveform determining step of, when a slope line of the fluctuation waveform steep gradient portion obtained at the frequency fluctuation time-series analyzing and computing step is substantially parallel to a slope line of a slope waveform steep gradient portion in the frequency slope time-series waveform immediately before emergence of the fluctuation waveform steep gradient portion, determining a waveform at that time as a sleepiness state. In this case, such a configuration is preferably adopted that the sleepiness waveform determining step performs comparison with teaching data of a sleepiness state leading to sleep onset, and the frequency fluctuation time-series waveform and the frequency slope time-series waveform at an occurrence time of the sleep-onset point, which are preliminarily measured, to determine emergences of the fluctuation waveform steep gradient portion and the slope waveform steep gradient portion.

Such a configuration is preferably adopted that the waveform determining step further includes a fatigue state estimating step of comparing the frequency slope time-series waveform obtained from the frequency slope time-series analyzing and computing step and the frequency fluctuation time-series waveform obtained from the frequency fluctuation time-series analyzing and computing step with each other to estimate a fatigue state from a degree of a difference between both the waveforms. Such a configuration is preferably adopted that the fatigue state estimating step includes a step of determining a case where the frequency fluctuation time-series waveform transitions with an approximately equal amplitude at an approximately equal frequency while involving a predetermined phase delay relative to the frequency slope time-series waveform as a fatigue-free well state and estimating a fatigue state in a stepwise fashion according to whether or not a predetermined or more change occurs from the well state regarding at least one item of an initial phase angle, a phase difference, an amplitude, and an angular frequency. Such a configuration can be adopted that the fatigue state estimating step converts the frequency slope time-series waveform and the frequency fluctuation time-series waveform into sinusoidal models of a single harmonic motion, respectively, to perform estimation of the fatigue state between both the sinusoidal models. Further, such a configuration can be adopted that the fatigue state estimating step converts the frequency slope time-series waveform and the frequency fluctuation time-series waveform into sinusoidal models of a single harmonic motion, then synthesizes both the sinusoidal models to obtain a synthesized wave, compares the synthesized wave thus obtained with a synthesized wave obtained in a fatigue-free well state to perform estimation of a fatigue state.

Such a configuration is preferably adopted that the frequency calculating step includes at least one of a step which smoothing-differentiates the time-series waveform of the biological signal to obtain a maximum value and obtain a time-series waveform of the frequency of the biological signal using the maximum value, and a step which obtains a zero-crossing point at which a positive value changes to a negative value in the time-series waveform of the biological signal and obtains a time-series waveform of the frequency of the biological signal using the zero-crossing point.

Such a configuration can be adopted that the frequency computing step includes a first frequency computing step of smoothing-differentiating the time-series waveform of the biological signal to obtain a maximum value and obtain a time-series waveform of the frequency of the biological signal using the maximum value and a second frequency computing step of obtaining a zero-crossing point at which a positive value changes to a negative value in the time-series waveform of the biological signal and obtaining a time-series waveform of the frequency of the biological signal using the zero-crossing point;

the frequency slope time-series analyzing and computing step includes a first frequency slope time-series analyzing and computing step of performing movement calculation for obtaining a slope of the frequency for each predetermined time window set in a predetermined overlapped time in the time-series waveform of the frequency of the biological signal obtained by the first frequency computing means and outputting a time series change of the slope of the frequency obtained for each time window as a frequency slope time-series waveform, and a second frequency slope time-series analyzing and computing step of performing movement calculation for obtaining a slope of the frequency for each predetermined time window set in a predetermined overlapped time in the time-series waveform of the frequency of the biological signal obtained by the second frequency computing step and outputting a time series change of the slope of the frequency obtained for each time window as a frequency slope time-series waveform; and the waveform determining step includes a first integral curve computing step of applying absolute value processing to the frequency slope time-series waveform obtained by the first frequency slope time-series analyzing and computing step to integrate the same and obtain a first integral curve, a second integral curve computing step of applying absolute value processing to the frequency slope time-series waveform obtained by the second frequency slope time-series analyzing and computing step to integrate the same and obtain a second integral curve, and an integral curve determining step of comparing the respective integral curves obtained by the first integral curve computing means and the second integral curve computing means, respectively, with each other. Such a configuration is preferably adopted that the integral curve determining step determines a state of a person from shape patterns of the respective integral curves.

Advantageous Effects of Invention

According to the present invention, by capturing a frequency fluctuation time-series waveform of an aortic pulse wave detected from a dorsal region of an upper body of a person, a slope time-series waveform of the time-series waveform at that time (frequency slope time-series waveform), and a change of a base line of the frequency fluctuation time-series waveform, a state change of the person could be captured with timing closer to consciousness of the person based upon the respective time-series waveforms. In particular, based upon the fact that a steep gradient portion of a fluctuation waveform indicating a steep gradient change in the frequency fluctuation time-series waveform emerged, and the amplitude of the frequency fluctuation time-series waveform or the frequency slope time-series waveform thereafter and the position of the base line of the frequency fluctuation time-series waveform were in predetermined ranges, a sleep-onset point could be specified clearly. Further, by adopting such a configuration that in the case where lowering of the base line of the frequency fluctuation time-series waveform occurred and a mean slope line of the steep gradient portion (fluctuation waveform steep gradient portion) was approximately parallel to a mean slope line of the steep gradient portion (slope waveform steep gradient portion) in the frequency slope time-series waveform before emergence of the steep gradient portion of the frequency fluctuation time-series waveform was determined as a waveform indicating a sleepiness state (sleepiness waveform), a sleep prediction phenomenon involving sleepiness could be detected. Since an occurrence time point of the sleepiness waveform is approximately in synchronization with a timing at which a person becomes conscious of sleepiness, if an alert is issued at this timing, a person can become clearly aware that the alert is an alert for preventing dozing, where rising of an activation level is generated so that improvement of a dozing-preventing effect can be expected. Further, by comparing the frequency fluctuation time-series waveform and the frequency slope time-series waveform with each other, the fatigue state of a person can be estimated.

In addition, by adopting such a configuration that two data items of the case where a maximum value obtained by smoothing-differentiating a time-series waveform of a frequency of a biological signal (aortic pulse wave) was used and the case where a zero-crossing point at which a positive value changes to a negative value was obtained and the zero-crossing point was used were obtained and a frequency slope waveform was obtained from these two data items so that an integral curve thereof was depicted, a fatigue degree of a person (a fatigue-free state, a state where a fatigue is compensated for by sympathetic nervous activity, a state where an error or delay of a reaction time emerges due to fatigue, or the like) can be analyzed simply.

BRIEF DESCRIPTION OF DRAWINGS

FIG. 3C being a bottom view thereof, and FIG. 3D being a sectional view thereof taken along line A-A.

DESCRIPTION OF EMBODIMENTS

Figure 1:
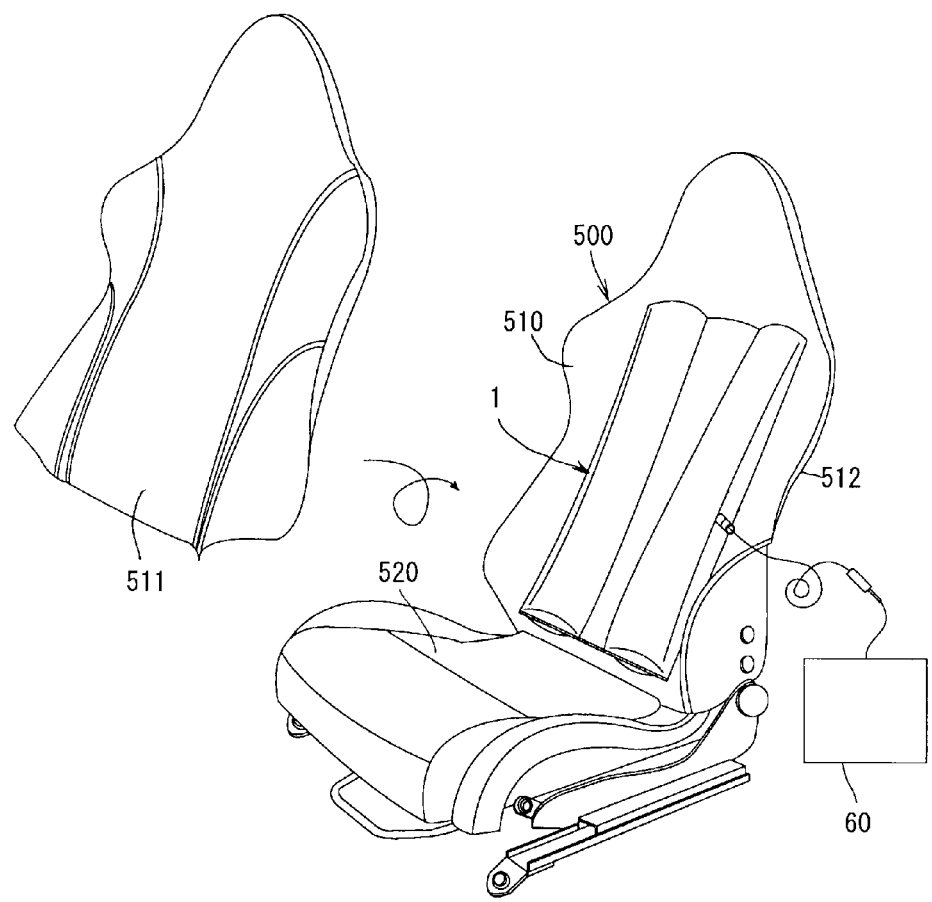
FIG. 1 is a view showing a state where a biological signal measuring device according to an embodiment of the present invention has been assembled into a seat.

Hereinafter, embodiments of the present invention will be explained in detail with reference to the drawings. FIG. 1 is a view showing an exterior of an automobile seat 500 assembled with a biological signal measuring device 1 obtaining aortic pulse waves to be analyzed in a biological body state analyzing device 60 according to this embodiment (biological signals involving motion of an atrium and fluctuation of an aorta detected from a dorsal region of an upper body of a person). As shown in this figure, the biological signal measuring device 1 is used in an assembled state thereof into a seatback section 510. Here, it is desirable that signals obtained by the biological signal measuring device 1 contain less noise signals except for biological signal components. In view of these circumstances, as described below, the biological signal measuring device 1 according to this embodiment has been applied with ingenuity which can reduce noise signals involved in sensor output signals themselves even under a vibration environment such as in a moving automobile.

Figure 4:
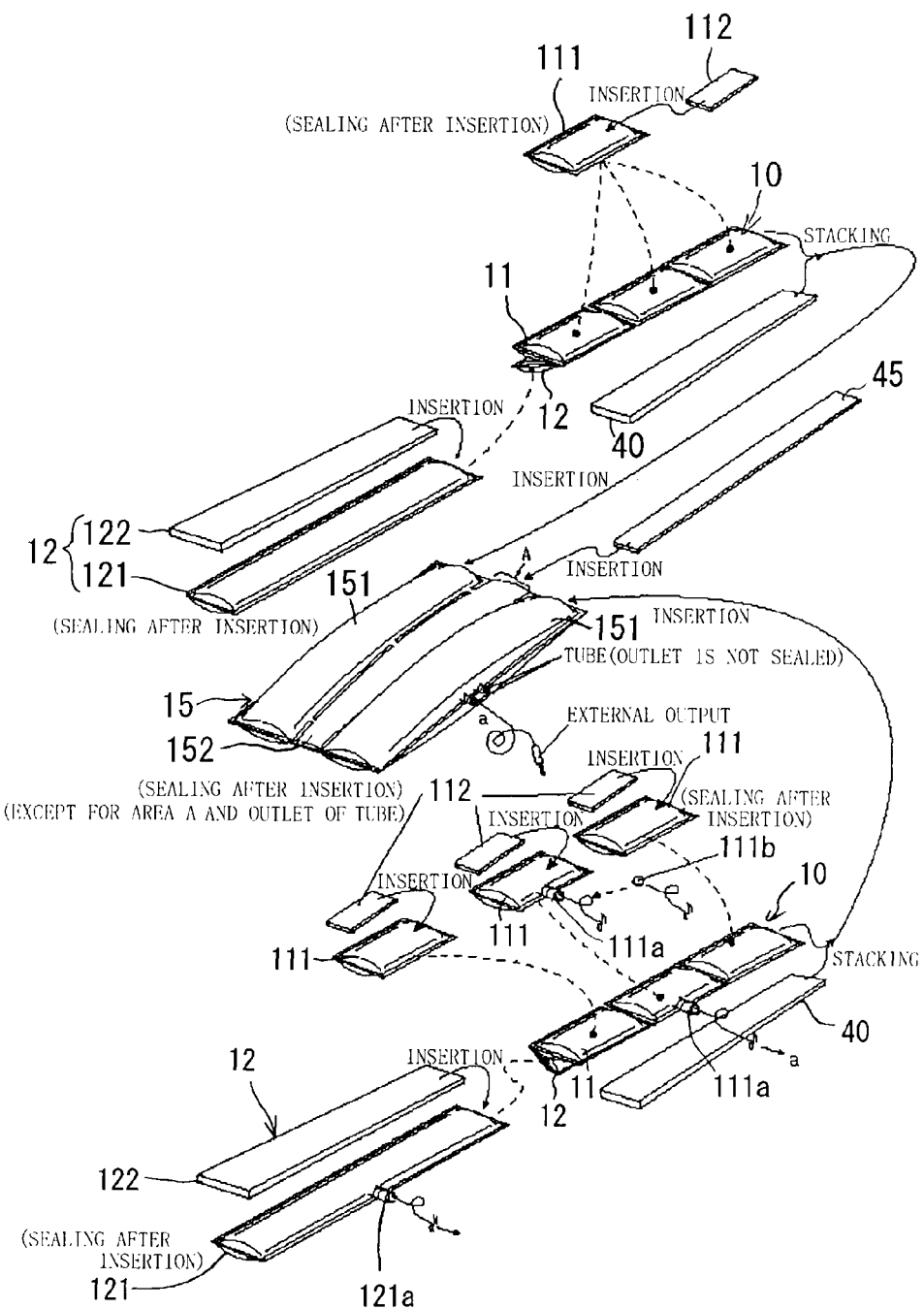
FIG. 4 is an exploded perspective view of the air-pack unit.
Figure 5A:
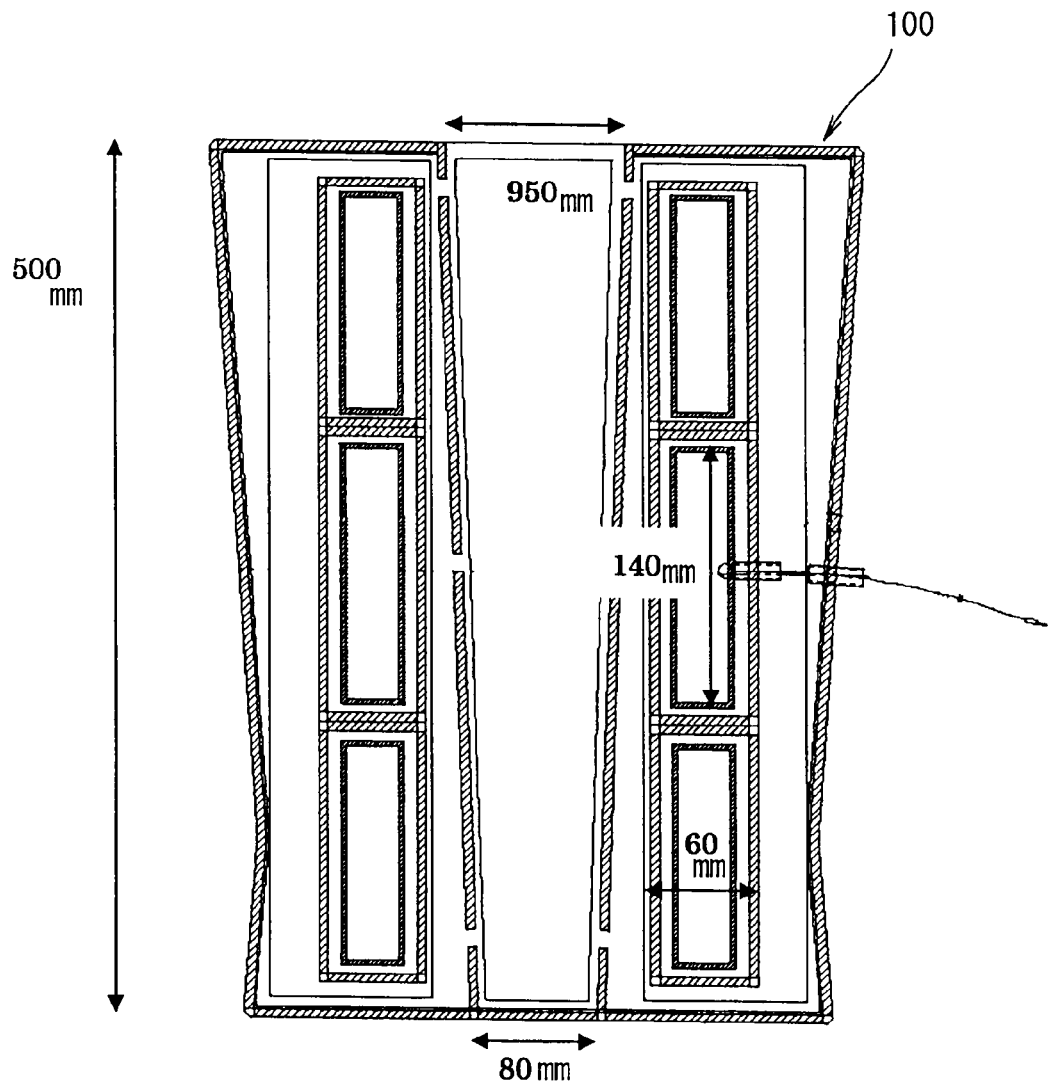
FIGS. 5A and 5B are views for describing a size of an air-pack unit used in a test example.
Figure 5B:
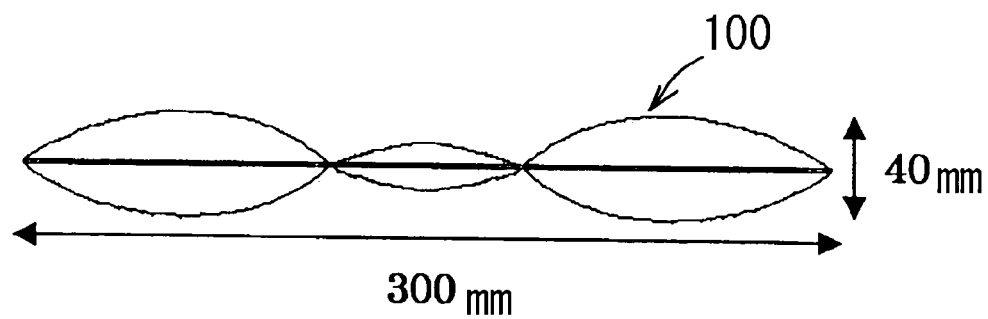

The biological signal measuring device 1 is configured to include an air-pack unit 100, a first elastic member 20 made of expanded resin beads, and a second elastic member 30 made of expanded resin beads. The air-pack unit 100 is configured to include a receiving body 15 and two air packs 10 received in this receiving body 15. As shown in FIGS. 3 and 4, the air packs 10 are each configured by stacking a surface side air pack 11 and a back surface side air pack 12, and they are disposed on the right and the left sides of the receiving body 15, respectively. The surface side air pack 11 is formed such that it comprises three small airbags 111 connected in series in a vertical direction, while air communication among these small airbags 111 is prevented. Three-dimensional solid knitted fabrics 112 serving as resilience-imparting members are disposed within the respective small airbags 111.

The back surface side air pack 12 is configured to include a large airbag 121 with the same length as the entire length of the surface side air pack 11 comprising three small airbags 111 connected in series and a three-dimensional solid knitted fabric 122 serving as a resilience-imparting member and received in the large airbag 121 (see FIG. 4). The surface side air pack 11 and the back surface side air pack 12 are used, after they are joined to each other at their one edges positioned along their longitudinal directions and they are folded about the joined side edges to be stacked on each other (see FIG. 3D and FIG. 4).

In this embodiment, air packs 10 obtained by stacking the surface side air pack 11 and the back surface side air pack 12 mutually in this manner are arranged on the right side and the left side. The arrangement of the respective air packs 10 on the right side and the left side makes contact of the seatback section to the back of a person sitting on the seat bilaterally even, so that the person does not feel uncomfortable. Further, a sensor mounting tube 111a is provided to one of the small airbags 111 configuring one of the right and left surface side air packs 11, 11, and a sensor 111b which measures air pressure fluctuation is fixed inside the small airbag 111. Incidentally, the sensor mounting tube 111a is sealed. Though the sensor may be disposed in the large airbag 121 configuring the back surface side air pack 12, if the sensor is provided in an airbag having a large volume, there is such a possibility that, air pressure fluctuation due to a pulse wave is absorbed by the airbag, so that it is preferred that the sensor is provided in the small airbag 111. As shown in FIG. 4, however, such a configuration can be adopted that the mounting tube 121a is preliminarily provided to the large airbag 121 and the sensor is arranged at the site of the mounting tube 121a, so that a result obtained by measuring air pressure fluctuation in the large airbag 121 can be utilized for verification of the measurement result of the small airbag 111 as necessary. In order to cause the small airbag 111 to respond to air pressure fluctuation due to such a biological signal susceptibly, it is preferred that the size of the small airbag 111 has a width of 40 to 100 mm and a length of 120 to 200 mm. A material for the small airbag 111 is not limited, but the small airbag 111 may be formed of a sheet made of, for example, polyurethane elastomer (for example, Product Number "DUS605-CDR" produced by Sheedom Co., Ltd.). As the sensor 111b, one which can measure air pressure within the small airbag 111 can be used, for example, a capacitive microphone sensor can be used.

As the size of the large airbag 121 and the entire size of the three small airbags 111 connected in series, it is preferred that the width and the entire length fall within a range of 40 to 100 mm and a range of 400 to 600 mm when these airbags 121 and 111 are used in the seatback section 510 of the automobile seat 500. When the length is short, a person sitting on the seat feels uncomfortable only at a portion of the seat positioned near his/her lumber area in the seatback section 510, so that it is preferred that the length is set to 400 mm or more and the airbags accommodate the entire back of the person sitting on the seat as much as possible.

In this embodiment, the sensor 111b which detects air pressure fluctuation is provided in a central small airbag 111 of the surface side air pack 11 configuring the air pack 10 arranged on the left side of the person sitting on the seat. The position of the small airbag 111 corresponds to a region where biological signals (aortic pulse waves) involved in motion of an atrium and fluctuation of an aorta (especially, "downward aorta") obtained from the dorsal region of the person are detectable. The region where the aortic pulse waves are detectable is not uniform due to the frame of a person sitting on the seat, but, as a result of measuring 20 subjects of various build from a 158-centimeter-tall Japanese woman to a 185-centimeter-tall Japanese man, the aortic pulse waves regarding all the subjects could be detected when an intersecting portion P (see FIG. 2 and FIG. 3) of a side edge of the small airbag 111 (having a width of 60 mm and a length of 160 mm) positioned nearer to the center of the seatback section 510 and a lower edge thereof was set such that a length L from an upper face of the seat cushion section 520 along a surface of the seatback section 510 was 220 mm and a distance M from the center of the seatback section 510 was 80 mm. When the size of the small airbag 111 is set such that its width is in a range of 40 to 100 mm and its length is in a range of 120 to 200 mm, it is preferred that the position of the intersecting portion P is set such that the length from the upper face of the seat cushion section 520 along the surface of seatback section 510 is in a range of 150 to 280 mm and the distance from the center of the seatback section 510 is in a range of 60 to 120 mm.

Figure 2:
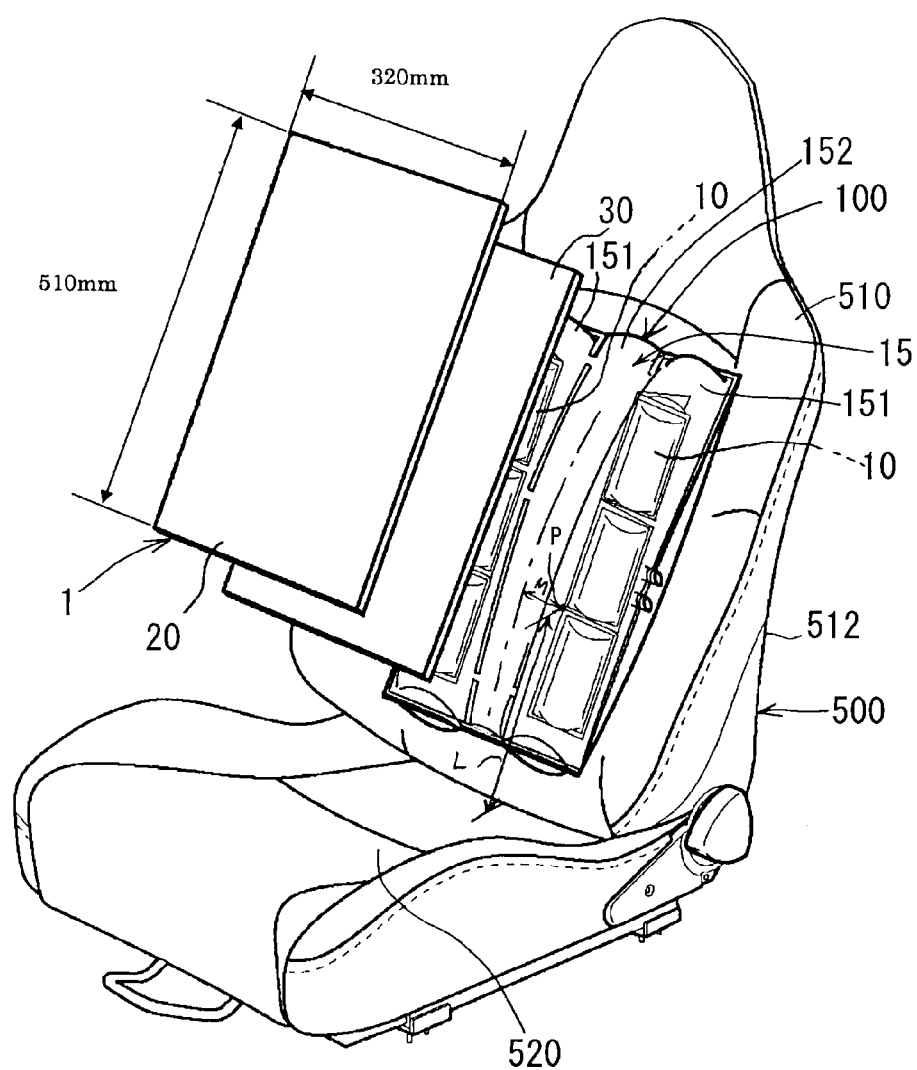
FIG. 2 is a view showing the biological signal measuring device according to the embodiment in more detail.
Figure 3A:
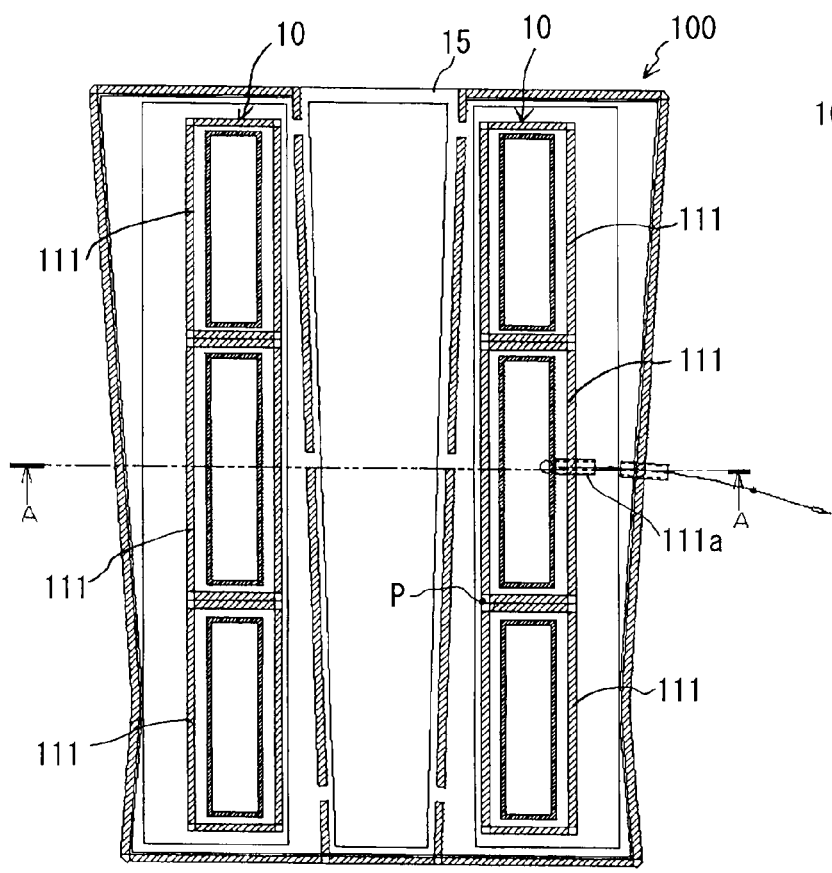
FIGS. 3A to 3D are views showing an air-pack unit, FIG. 3A being a sectional view of the air-pack unit as viewed from the front, FIG. 3B being a side view thereof.
Figure 3B:
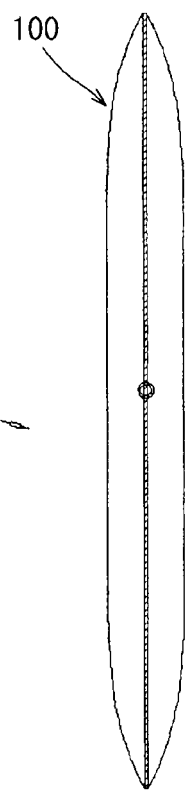
Figure 3C:
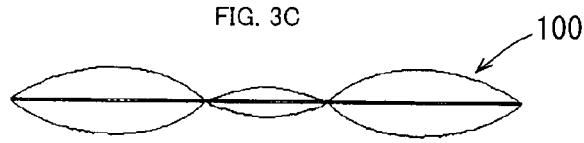
Figure 3D:
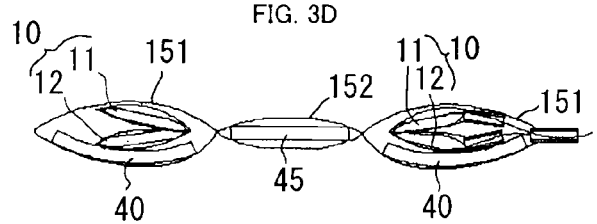

It is preferred that the above-described two air packs 10 are unitized such that they can be easily set at predetermined positions in the seatback section 510. Therefore, it is preferred that an air-pack unit 100 obtained by loading the air packs 10 into a receiving body 15 such as shown in FIG. 2 to FIG. 4 is configured. The receiving body 15 has bag-shaped air pack receiving portions 151 receiving the air pack 10 on both sides and, and it has a connecting portion 152 between two air pack receiving portions 151.

The air packs 10 are inserted into two air pack receiving portions 151, respectively. It is also preferred that a three-dimensional solid knitted fabric 40 with approximately the same size as the air pack 10 is inserted into the air pack receiving portion 151 so as to be positioned on a back face of the back surface side air pack 12 of the air pack in a stacking state (see FIG. 3D). By arranging the three-dimensional solid knitted fabric 40, the air pack 10 is supported in a so-called floating manner by the three-dimensional solid knitted fabric 40, so that transmission of external vibrations from the seatback section 510 becomes difficult. That is, by arranging the three-dimensional solid knitted fabric 40, a spring-mass-damper system with a low spring constant is produced within the air pack from piles of the three-dimensional solid knitted fabric 40 and fluctuation of air pressure at an inputting time of high-frequency external vibrations with small amplitude. Then, the spring-mass-damper system serves as filters to low-frequency and high-frequency inputs (a low-pass filter and a high-pass filter) in the air pack 10 housing the three-dimensional solid knitted fabric 40 therein to damp the external vibrations.

The connecting portion 152 may be a member which can support two air packs 151 spaced from each other by a predetermined distance, and it is formed to have a width of about 60 to 120 mm. It is preferred that the connecting portion 152 is formed in a bag shape, so that a three-dimensional solid knitted fabric 45 is inserted therein (see FIG. 3D and FIG. 4). Thereby, vibrations inputted through the connecting portion 152 can also be removed effectively by inserting the three-dimensional solid knitted fabric 45 into the connecting portion 152, so that transmission of external vibrations to the air pack 10 provided with the sensor 111b can be suppressed.

Incidentally, as described above, the small airbag 111 can be formed of a sheet made of, for example, polyurethane elastomer (for example, Product Number "DUS605-CDR" produced by Sheedom Co., Ltd.), but it is preferred that the large airbag 121 forming the back surface side air pack 12 and the receiving body 15 are also made of the same material as that for the small airbag 111. The respective three-dimensional solid knitted fabrics loaded into the small airbags 111, the large airbag 121, the air pack receiving portion 151, and the connecting portion 152 are knitted fabrics having a solid three-dimensional structure having a pair of ground knitted fabrics arranged so as to be spaced from each other and many connecting strands reciprocating between the pair of ground knitted fabrics to connect both the ground knitted fabrics, as disclosed in Japanese Patent Application Laid-Open No. 2002-331603.

One of the ground knitted fabrics is formed of, for example, a flat knitted fabric texture (fine mesh) continuous both in a wale direction and in a course direction from strands obtained by twisting monofilaments, while the other ground knitted fabric is formed of, for example, a knitted stitch structure having a honeycomb shape (hexagonal shape) meshes from strands obtained by twisting monofilaments. Of course, the knitted fabric texture is arbitrary, and a knitted fabric texture other than the fine mesh texture or the honeycomb shape can be adopted, and any combination of knitted fabric textures such as adoption of the fine mesh texture in both the ground knitted fabrics can be adopted in both the ground knitted fabrics. The connecting strands are knitted between the two ground knitted fabrics such that one of the ground knitted fabrics and the other are kept away from each other by a predetermined distance. As such a three-dimensional solid knitted fabric, for example, materials described below can be used. Incidentally, the respective three-dimensional solid knitted fabrics can also be used in a state that a plurality of three-dimensional solid knitted fabrics has been stacked one on another as necessary.

(1) Product Number: 49076D (produced by Suminoe Textile Co., Ltd.) Material:

Surface side ground knitted fabric . . . twisted yarn of polyethylene terephthalate fiber false-twisted yarn of 300 decitex/288f and polyethylene terephthalate fiber false-twisted yarn of 700 decitex/192f Back surface side ground knitted fabric . . . combination of polyethylene terephthalate fiber false-twisted yarn of 450 decitex/108f and poly-trimethylene telephthalate monofilament of 350 decitex/1f Connecting strand . . . poly-trimethylene terephthalate monofilament of 350 decitex/1f (2) Product Number: 49011D (produced by Suminoe Textile Co., Ltd.) Material:

Ground knitted fabric (warp) . . . polyethylene terephthalate fiber false-twisted yarn of 600 decitex/192f Ground knitted fabric (weft) . . . polyethylene terephthalate fiber false-twisted yarn of 300 decitex/72f Connecting strand . . . polyethylene terephthalate monofilament of 800 decitex/1f (3) Product Number: 49013D (produced by Suminoe Textile Co., Ltd.) Material:

Surface side ground knitted fabric . . . twisted yarn of two polyethylene terephthalate fiber false-twisted yarns of 450 decitex/108f Back surface side ground knitted fabric . . . twisted yarn of two polyethylene terephthalate fiber false-twisted yarns of 450 decitex/108f Connecting strand . . . poly-trimethylene terephthalate monofilament of 350 decitex/1f (4) Product Number: 49030D (produced by Suminoe Textile Co., Ltd.) Material:

Surface side ground knitted fabric . . . twisted yarn of two polyethylene terephthalate fiber false-twisted yarns of 450 decitex/144f Back side surface ground knitted fabric . . . combination of polyethylene terephthalate fiber false-twisted yarn of 450 decitex/144f and poly-trimethylene telephthalate monofilament of 350 decitex/1f Connecting strand . . . poly-trimethylene terephthalate monofilament of 350 decitex/1f (5) Product Number produced by Asahi Kasei Fibers Corporation: T24053AY5-1S The first elastic member made of expanded rein beads 20 and the second elastic member made of expanded resin beads 30 are disposed between a skin member of the seatback section 510 and the receiving body 15 (air-pack unit 100) which has received the air packs 10 therein. They have a length corresponding to the entire length of two air packs 10 and they have a width corresponding to a length between top portions of two air packs 10. Therefore, it is preferred that members having such a size that a length is in a range of 400 to 600 mm and a width is in a range of about 250 to 350 mm are used. Thereby, since two air packs 10 are covered with these members, undulation feeling due to the two air packs 10 is reduced.

The first elastic member made of expanded resin beads 20 is composed of an expanded bead body formed in a flat-plate shape and a covering material caused to adhere to an outer face of the expanded bead body. As the expanded bead body, an expanded formation body obtained by a bead method of resin containing at least one of polystyrene, polypropylene, and polyethylene is used. Incidentally, an expansion ratio is set arbitrarily and it is not limited. The covering material is caused to adhere to an outer face of the expanded bead body by adhesive, and it is a material having a high extension percentage and a high recovery rate, so that an elastic fiber nonwoven fabric whose extension percentage is at least 200% and whose recovery rate at 100% extension time is 80% is preferably used. For example, a nonwoven fabric where thermoplastic elastomer elastic fibers have been caused to adhere to one another in a melting manner, which is disclosed in Japanese Patent Application Laid-Open NO. 2007-92217, can be used. Specifically, Trade Name "Espansione" produced by KB SEIREN, LTD. can be used.

The second elastic member made of expanded resin beads 30 is configured to have an expanded bead body like the first elastic member made of expanded resin beads 20, but as a covering material for covering an outer face of the expanded bead body, a material with a retractility smaller than that of the elastic fiber nonwoven fabric used in the first elastic member made of expanded resin beads 20, for example, a nonwoven fabric made of thermoplastic polyester is used. Specifically, a biaxial fabric (longitudinal: 20/inch, horizontal: 20/inch) formed from polyethylene naphthalate (PEN) fibers (1100 dtex) produced by TEIJIN LIMITED can be used.

The order of stacking the first elastic member made of expanded resin beads 20 and the second elastic member made of expanded resin beads 30 is not limited, but it is preferred that the first elastic member made of expanded resin beads 20 having a higher elasticity is disposed on a side closer to the skin member 511 of the seatback section 510. Further, the expanded bead body constituting the first and second elastic member made of expanded resin beads 20 and 30 is set to have a thickness of about 5 to 6 mm, and formation thereof is achieved by causing a nonwoven fabric made of the above-described elastic fiber nonwoven fabric or thermoplastic polyester having a thickness of about 1 mm or less to adhere to an outer face thereof. Incidentally, in the embodiment, polyester films such as a PEN film are caused to adhere to a face of the first elastic member made of expanded resin beads 20 opposed to the skin member 511 and a face of the second elastic member made of expanded resin beads 30 opposed to the air-pack unit 100, respectively. Thereby, transmissibility of a biological signal is improved.

In the embodiment, the seatback section 510 of the seat 500 configuring a human body supporting unit is provided with the skin member 511 and a cushion supporting member 512 disposed on a back surface side of the skin member 511, and the receiving body 15 (air-pack unit 100) holding the air packs 10 and the first and second elastic members made of expanded resin beads 20 and 30 are assembled between the skin member 511 and the cushion supporting member 512. At this time, the receiving body 15 (air-pack unit 100) holding the air packs 10 is first disposed on the side of the cushion supporting member 512, the second elastic member made of expanded resin beads 30 is disposed on a surface side of the receiving body 15, and after the first elastic member made of expanded resin beads 20 is further disposed on a surface side of the second elastic member made of expanded resin beads 30, these members are covered with the skin member 511. Incidentally, the cushion supporting member 512 can be formed by stretching a three-dimensional solid knitted fabric between rear end edges of a pair of right and left side frames of the seatback section 510 or can be formed of a synthetic resin plate. The skin member 511 can be provided by stretching, for example, a three-dimensional solid knitted fabric, an artificial leather, a leather, or a laminated body of these members between front edges of the pair of right and left side frames.

In this embodiment, thus, since the configuration where the first elastic member made of expanded resin beads 20 and the second elastic member made of expanded resin beads 30 which have predetermined sizes are disposed on the back surface side of the skin member 511 in a stacking state and the receiving body 15 (air-pack unit 100) holding the a pair of right and left air packs 10 is further disposed behind them is adopted, a person sitting on the seat is prevented from feeling undulation of the air packs 10 on his/her back, and sitting feeling is improved though the configuration having the air packs 10 for measuring biological signals is adopted.

Next, the configuration of the biological body state analyzing device 60 will be described with reference to FIG. 6. The biological body state analyzing device 60 is assembled with a state analyzing section 610 which analyzes a state of a person from a time-series waveform of an aortic pulse wave (hereinafter, called "air-pack pulse wave" in some cases) which is a biological signal detected by the biological signal measuring device 1. Incidentally, since the biological signal measuring device 1 used in this embodiment has been applied with measure against noise, as described above, mixing of noise into detected signals is reduced, but such a case where noise other than pulse waves is contained in detected signals especially under a dynamic environment such as during automobile driving often occurs. In such a case, therefore, it is preferred that, as pre-processing performed before processing is performed in the state analyzing section 610, processing such as filtrating a detected signal at a predetermined frequency containing an aortic pulse wave is performed, and the pre-processed detected signal is used as a time-series waveform of the aortic pulse wave (air-pack pulse wave).

In this embodiment, the state analyzing section 610 is composed of a computer program set in a storage section of the biological body state analyzing device 60. That is, the state analyzing section 610 is composed of a frequency computing means (frequency computing step) 611, a frequency slope time-series analyzing and computing means (frequency slope time-series analyzing and computing step) 612, a frequency fluctuation time-series analyzing and computing means (frequency fluctuation time-series analyzing and computing step) 613, and a waveform determining means (waveform determining step) 614. Incidentally, the computer program can be provided in a state stored in such a recording medium as a flexible disk, a hard disk, a CD-ROM, an MO (magnetooptic disk), or a DVD-ROM, and it may also be transmitted through a communication line.

The frequency computing means (frequency computing step) 611 obtains a time-series waveform of a frequency in a time-series waveform of an aortic pulse wave (air-pack pulse wave) obtained from the biological signal measuring device 1. Specifically, first of all, a maximum value (peak) is obtained by smoothing-differentiating the time-series waveform of the air-pack pulse wave. For example, the maximum value is obtained by a smoothing-differentiation method according to Savitzky and Golay. Next, the maximum value is obtained for each 5 seconds, a reciprocals of time intervals between the maximum values (top portion on an upper side of a waveform) of the time-series waveform contained in the 5 seconds are obtained as individual frequencies f, and a mean value of the individual frequencies f for the 5 seconds is adopted as a value of a frequency F for the 5 seconds (Step [1] in FIG. 7). Then, a time-series waveform of the frequency is obtained by plotting the frequency F obtained for each 5 seconds (Step [2] in FIG. 7).

The frequency time-series analyzing slope and computing means (frequency slope time-series analyzing and computing step) 612 sets a time window having a predetermined time width from the time-series waveform of the frequency of the air-pack pulse wave obtained from the frequency computing means 611, and obtains the slope of the frequency of the air-pack pulse wave for each time window by least-square method to output a time series wave thereof. Specifically, first, a slope of a frequency in a certain time window Tw1 is obtained by least-square method to be plotted (Steps [3] and [5] in FIG. 7). Next, the next time window Tw2 is set in an overlapped time T1 (Step [6] in FIG. 7) and a slope of a frequency in this time window Tw2 is similarly obtained by least-square method to be plotted. This calculation (movement calculation) is repeated sequentially to output a slope time-series waveform of the frequency of the air-pack pulse wave as a frequency slope time-series waveform (Step [8] in FIG. 7). Incidentally, it is preferred that the time width of the time window Tw is set to 180 seconds, and it is preferred that the overlapped time T1 is set to 162 seconds. These values were selected as values at which a characteristic signal emerged with the best sensitivity from sleep experiments performed while changing the time width of the time window Tw and the overlapped time T1 variously, as shown in the above-described Patent Literature 3 (WO 2005/092193A1) of the present applicant.

Figure 7:
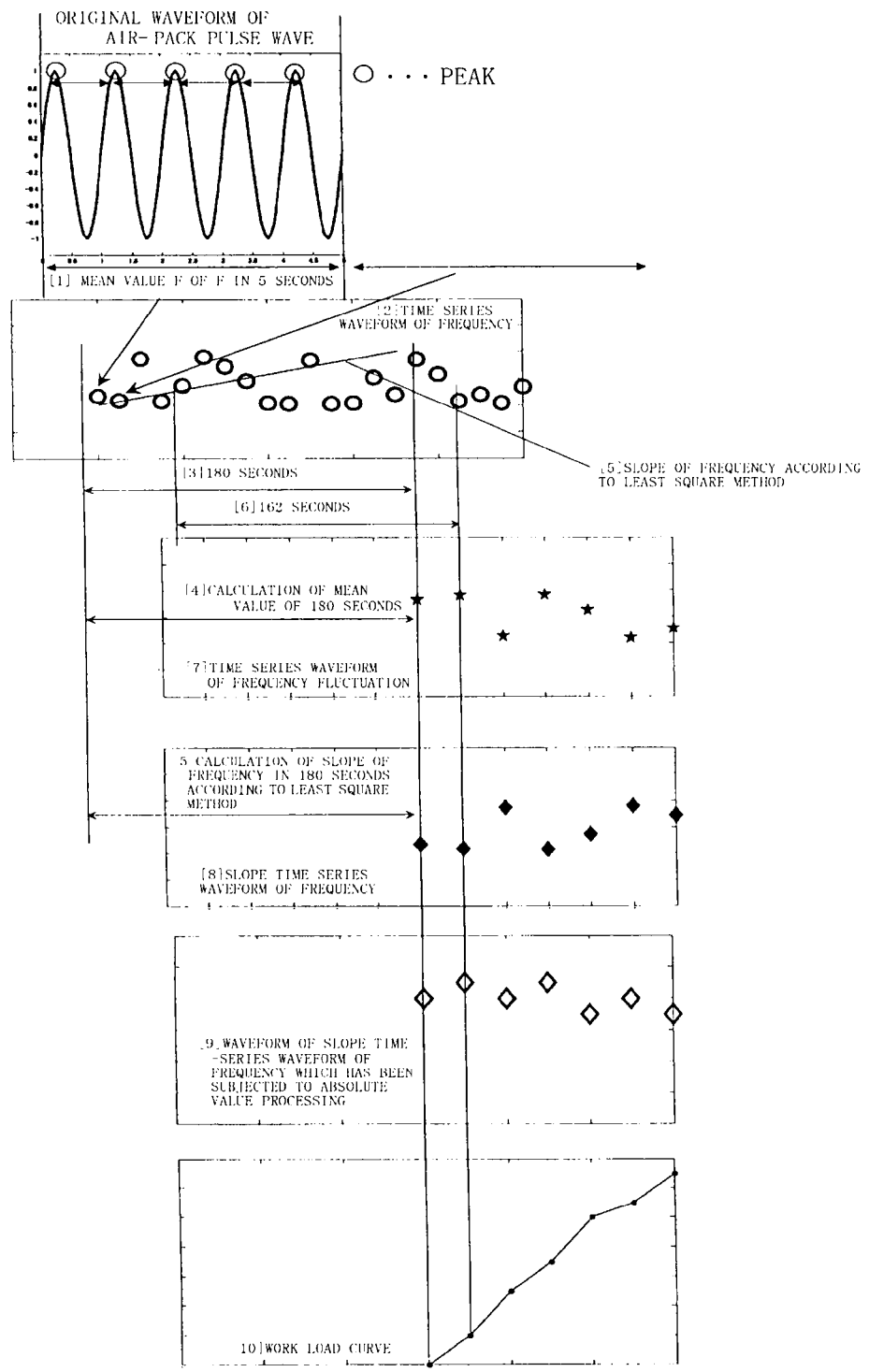
FIG. 7 is a diagram for describing a method for obtaining a frequency fluctuation time-series waveform, a base line of the frequency fluctuation time-series waveform, a frequency slope time-series waveform which is a slope time series of a frequency fluctuation, and an integral curve using a peak value of a pulse wave (heartbeat fluctuation) detected by the biological signal measuring device.

The frequency fluctuation time-series analyzing and computing means (frequency fluctuation time-series analyzing and computing step) 613 sets a time window with a predetermined time width (preferably, 180 seconds) to the time-series waveform of the frequency of the air-pack pulse wave obtained by the frequency computing means 611 (Step [2] in FIG. 7) to obtain a mean value of the frequency (Steps [3] and [4] in FIG. 7). Next, movement calculation for obtaining a mean value of the frequency of the air-pack pulse wave for each predetermined time window (preferably, 180 seconds) set in the predetermined overlapped time (preferably, 162 seconds) is performed so that the mean value is plotted. Then, the time series change of the mean value of the frequency plotted for each time window is outputted as a frequency fluctuation time-series waveform (Step [7] in FIG. 7). Further, a base line computing means (base line computing step) 613a is set in the frequency fluctuation time-series analyzing and computing means 613. The base line computing means 613a obtains a base line of the frequency fluctuation time-series waveform to output the same.

The pulse wave frequency computing means (pulse wave frequency computing step) 611, the frequency slope time-series analyzing and computing means (frequency slope time-series analyzing and computing step) 612, and the frequency fluctuation time-series analyzing and computing means (frequency fluctuation time-series analyzing and computing step) 613 can perform processing (hereinafter, called "zero-crossing method") according to steps in FIG. 8 instead of the processing (hereinafter, called "peak detecting method") according to steps in FIG. 7. The peak detecting method in FIG. 7 is configured such that the frequency computing means 611 smoothing-differentiates the times series waveform of the air-pack pulse wave obtained from the biological signal measuring device 1 to obtain the maximum value (peak value), while the zero-crossing method in FIG. 8 obtains a switching point from a positive value to a negative value (hereinafter, called "zero-crossing point") in the time-series waveform of the air-pack pulse wave. Then, the zero-crossing point is obtained for each 5 seconds, reciprocals of time intervals between the zero-crossing points of the time-series waveform contained in this 5 seconds are obtained as individual frequencies f, and a mean value of the individual frequencies f for the 5 seconds is adopted as a value of the frequency F for the 5 seconds (Step [1] in FIG. 8). Then, the time-series waveform of the frequency is obtained by plotting the frequency F obtained for each 5 seconds (Step [2] in FIG. 8).

Thereafter, movement calculation is performed to obtain the frequency slope time-series waveform by the frequency slope time-series analyzing and computing means 612 (Steps [3], [5], [6], and [8] in FIG. 8) and movement calculation is performed to obtain the frequency fluctuation time-series waveform by the frequency fluctuation time-series analyzing and computing means 613 (Steps [3], [4], [6], and [7] in FIG. 8) like the case shown in FIG. 7.

When the frequency slope time-series waveform, the frequency fluctuation time-series waveform, and the base line thereof are used to determine a state of a person in the waveform determining means 614 described later, either one of the peak detecting method and the zero-crossing method can be used. It is preferred that, since clear indication of a state of a person depends on differences among individuals, an appropriate method can be preliminarily set depending on individuals. On the other hand, when a state of a person is estimated using an integral curve described in another embodiment described later, either one of the peak detecting method and the zero-crossing method can be used in measuring a stable state under a static environment such as on an examination table, but it is preferred that when measuring is performed in a state that corresponds to an external stimulation in such a dynamic environment as in a moving automobile, an activation level is obtained on the basis of the zero-crossing method and an compensating action of a sympathetic nerve is identified on the basis of the peak detecting method. Incidentally, this point will be described in detail later.

Figure 10A:
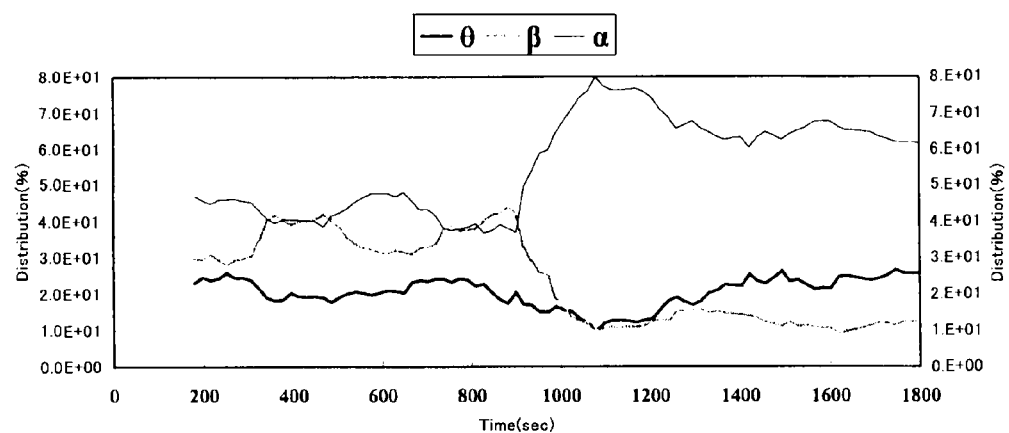
FIGS. 10A to 10D are graphs showing test results of a subject B, FIG. 10A showing time-series waveforms of distribution rates of θ wave, β wave, and α wave of a prefrontal area measured by an electroencephalograph, FIG. 10B showing time-series waveforms of HF component and LF/HF component obtained from a digital pulse volume, FIG. 10C showing time-series waveforms of a slope of a power value (finger photoplethysmogram power value slope) and a slope of a maximum Lyapunov exponent (finger photoplethysmogram lyapunov slope) obtained from the digital pulse volume, and FIG. 10D showing a frequency slope time-series waveform and a frequency fluctuation time-series waveform obtained using an air-pack pulse wave obtained from the biological signal measuring device according to the embodiment.
Figure 10B:
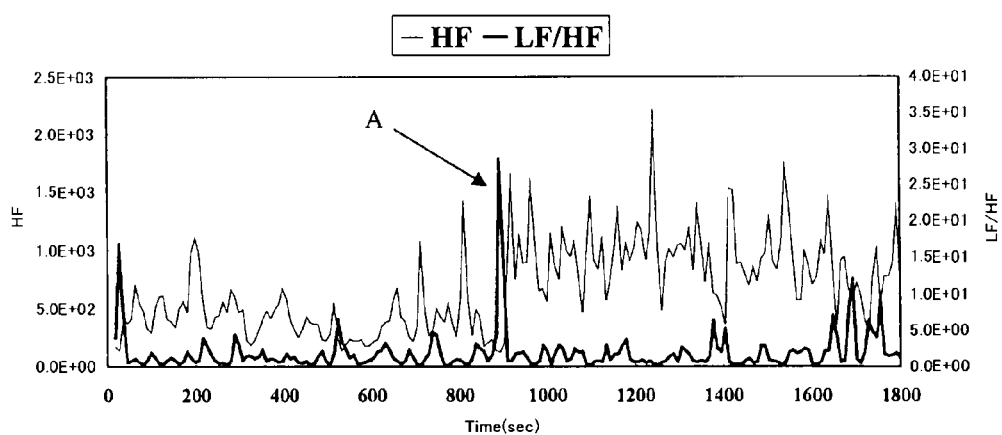
Figure 10C:
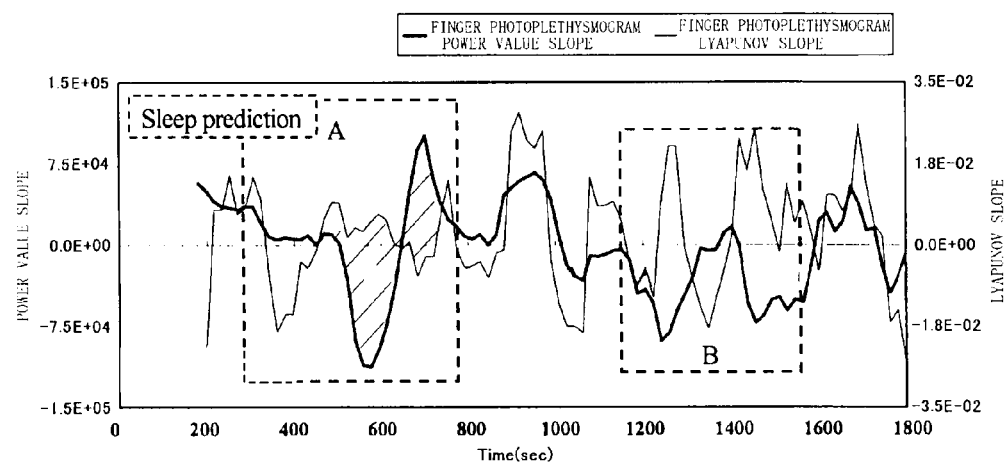
Figure 10D:
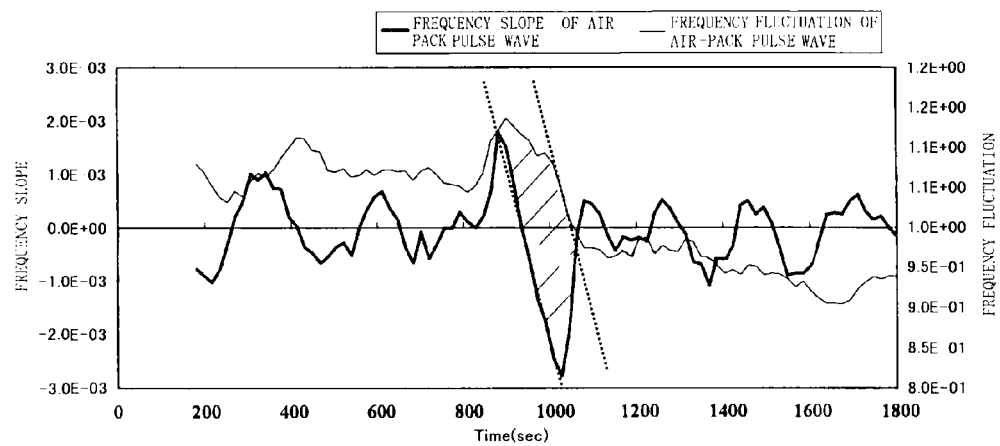
Figure 11A:
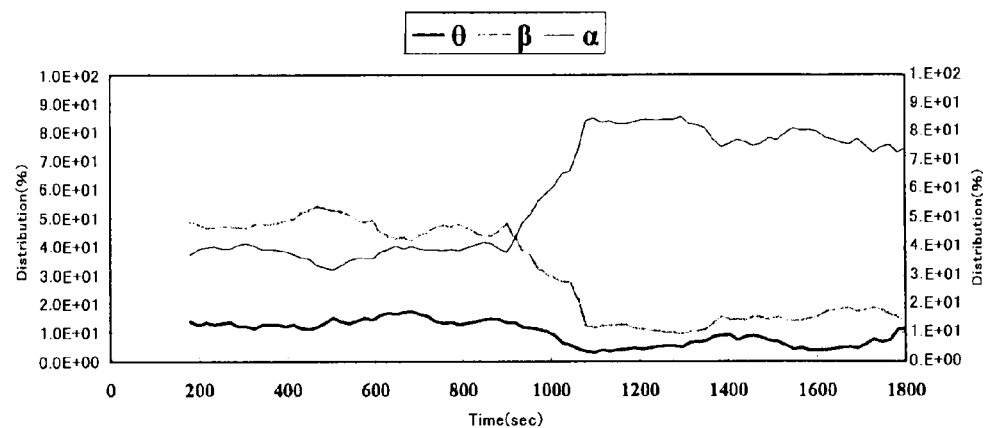
FIGS. 11A to 11D are graphs showing test results of a test subject C, FIG. 11A showing time-series waveforms of distribution rates of θ wave, β wave, and α wave of a prefrontal area measured by an electroencephalograph, FIG. 11B showing time-series waveforms of HF component and LF/HF component obtained from a digital pulse volume, FIG. 11C showing time-series waveforms of a slope of a power value (finger photoplethysmogram power value slope) and a slope of a maximum Lyapunov exponent (finger photoplethysmogram lyapunov slope) obtained from the digital pulse volume, and FIG. 11D showing a frequency slope time-series waveform and a frequency fluctuation time-series waveform obtained using an air-pack pulse wave obtained from the biological signal measuring device according to the embodiment.
Figure 11B:
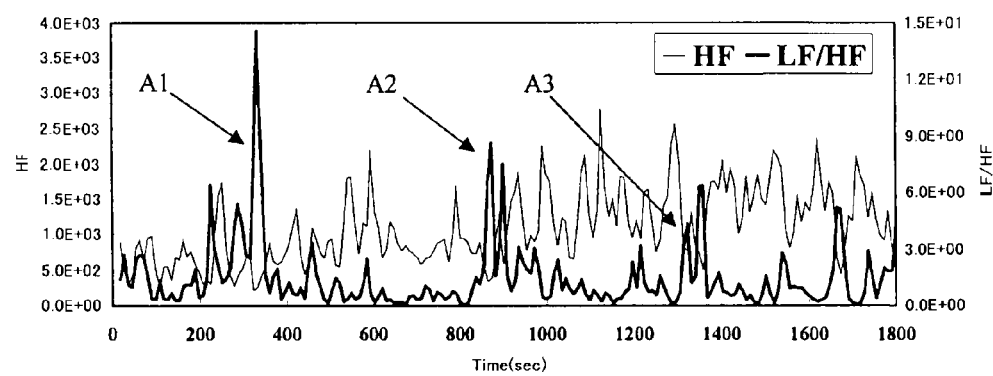
Figure 11C:
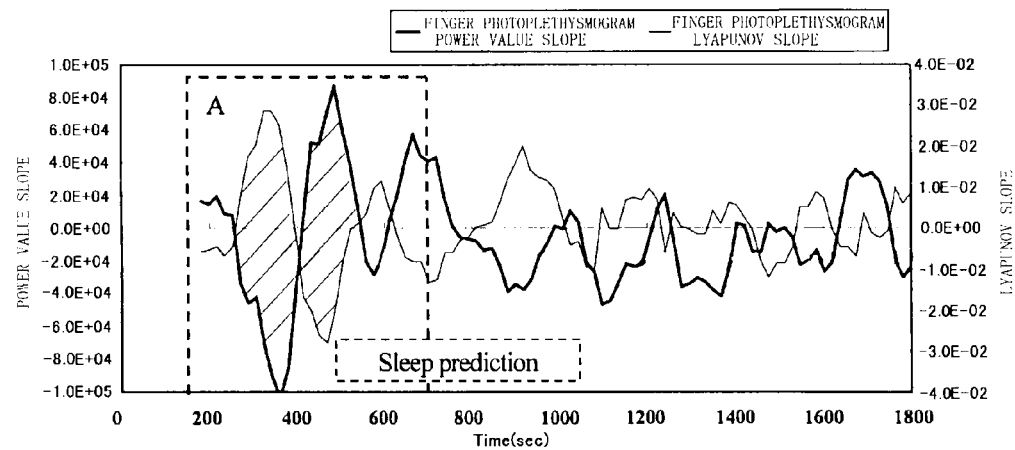
Figure 11D:
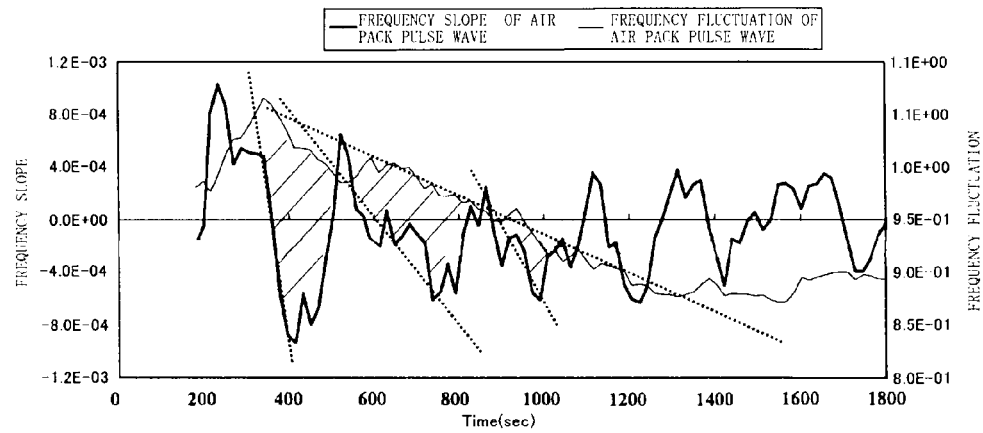
Figure 12A:
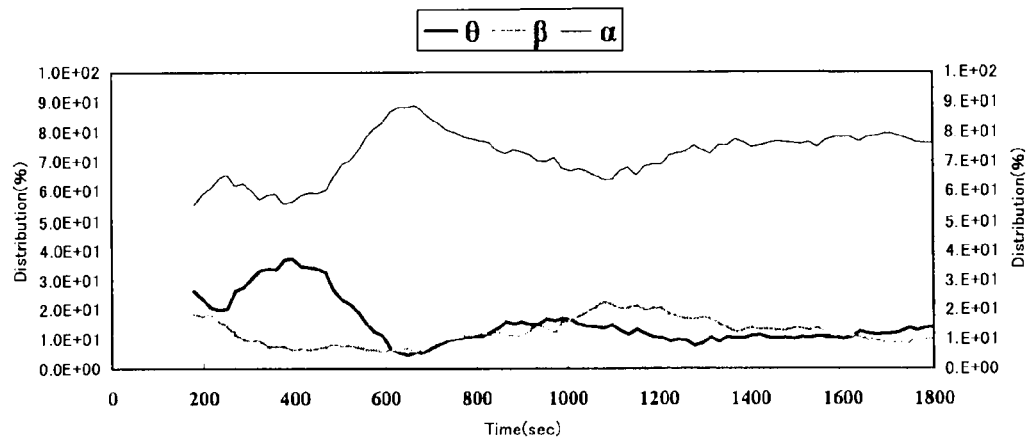
FIG. 12A to 12D are graphs showing test results of a subject D, FIG. 12A showing time-series waveforms of distribution rates of θ wave, β wave, and α wave of a prefrontal area measured by an electroencephalograph, FIG. 12B showing time-series waveforms of HF component and LF/HF component obtained from a digital pulse volume, FIG. 12C showing time-series waveforms of a slope of a power value (finger photoplethysmogram power value slope) and a slope of a maximum Lyapunov exponent (finger photoplethysmogram lyapunov slope) obtained from the digital pulse volume, and FIG. 12D showing a frequency slope time-series waveform and a frequency fluctuation time-series waveform obtained using an air-pack pulse wave obtained from the biological signal measuring device according to the embodiment.
Figure 12B:
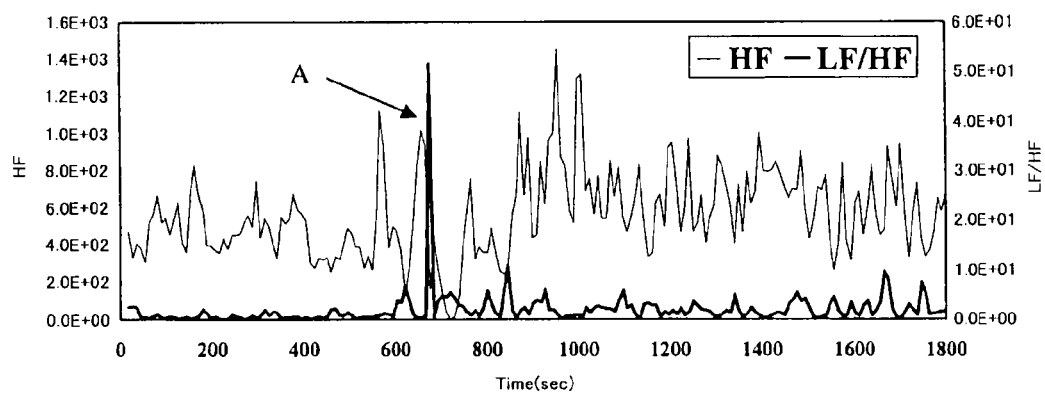
Figure 12C:
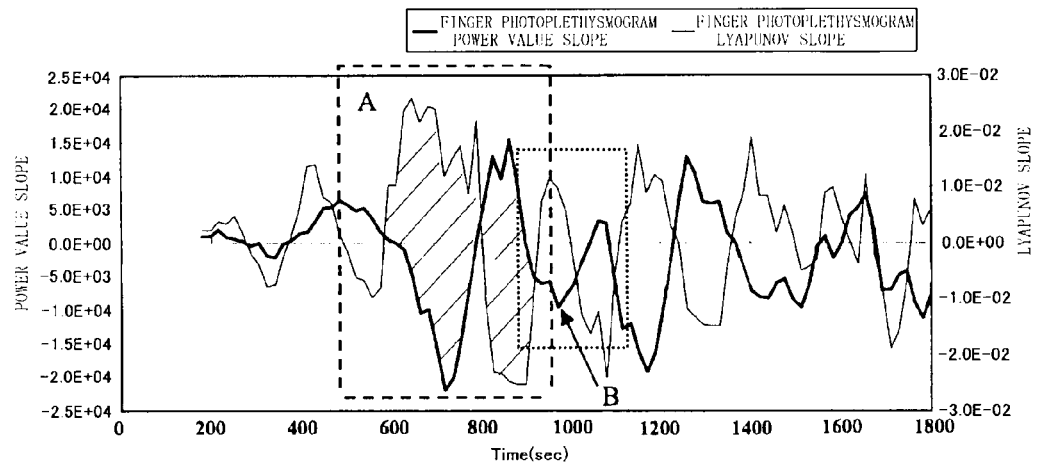
Figure 12D:
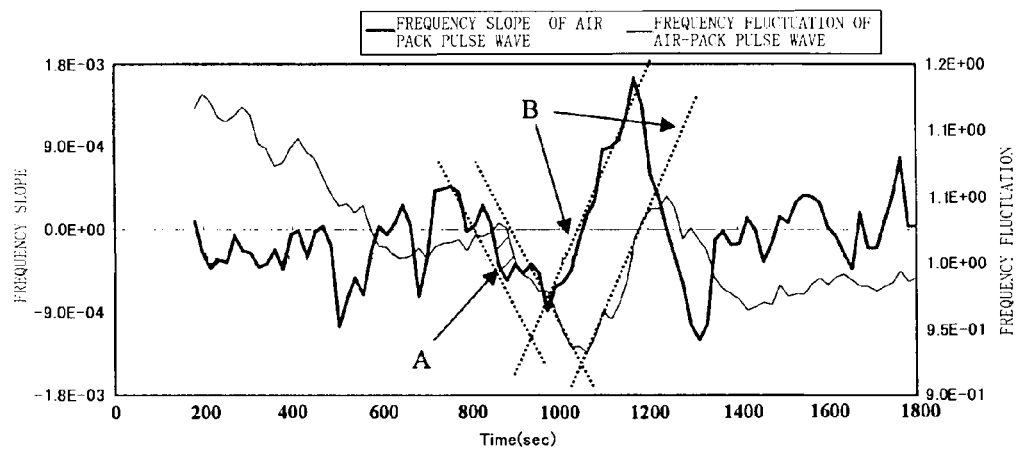

Incidentally, the frequency slope time-series analyzing and computing means 612 and the frequency fluctuation time-series analyzing and computing means 613 sequentially output the frequency slope time-series waveform and the frequency fluctuation time-series waveform of the air-pack pulse wave obtained therefrom on the same time axis from the start of the measurement thereof according to time elapsing (see FIG. 10D, FIG. 11D, and FIG. 12D).

The waveform determining means (waveform determining step) 614 performs comparison of the frequency slope time-series waveform, the frequency fluctuation time-series waveform and the base line of the frequency fluctuation time-series waveform outputted on the same time axis to analyze a state of a person from the waveform change of the both.

Figure 6:
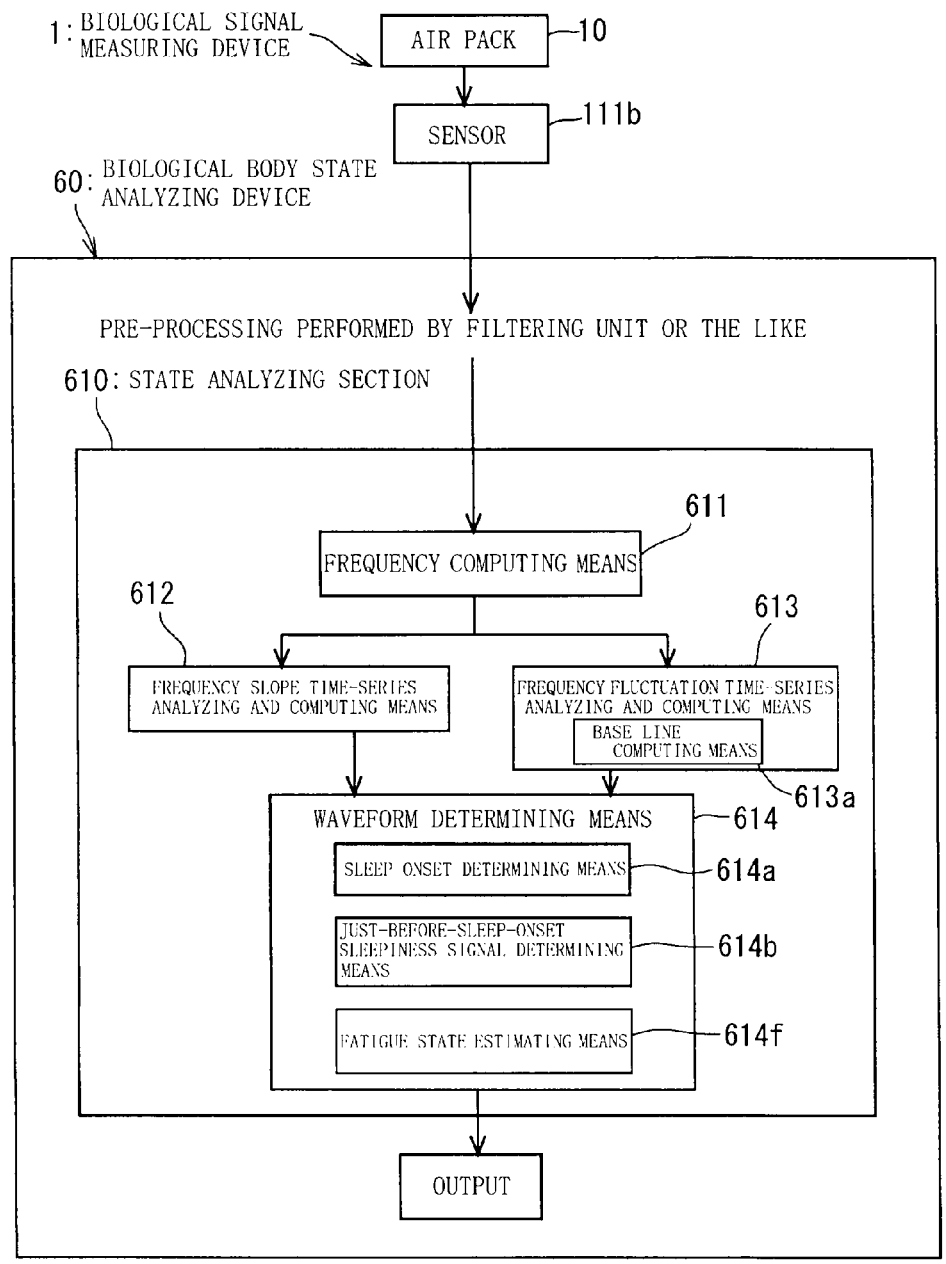
FIG. 6 is a diagram showing a configuration of the biological body state analyzing device according to the embodiment.

In this embodiment, as shown in FIG. 6, the waveform determining means 614 is provided with a sleep-onset point determining means (sleep onset determining step) 614a. When a fluctuation waveform steep gradient portion (a steep gradient portion extending along a slope line Y) indicating steep gradient change emerges in the frequency fluctuation time-series waveform obtained from the frequency fluctuation time-series analyzing and computing means 613, a base line position (the position of a base line E) of the frequency fluctuation time-series waveform thereafter does not return to a base line position (the position of a base line D) of the frequency fluctuation time-series waveform before emergence of the fluctuation waveform steep gradient portion, the base line E emerges in a downward sloping manner, and both an amplitude P of the frequency fluctuation time-series waveform and an amplitude Q of the frequency slope time-series waveform after emergence of the fluctuation waveform steep gradient portion are smaller than an amplitude R of the frequency fluctuation time-series waveform and an amplitude S of the frequency slope time-series waveform before emergence of the fluctuation waveform steep gradient portion, the sleep onset determining means 614a determines a terminal point of the fluctuation waveform steep gradient portion (a steep gradient portion extending along the slope line Y (a slope except for noise components contained in the waveform), namely, the vicinity of an intersecting point between an extension line of the base line E and an extension line of the slope line Y as a sleep-onset point C, with reference to FIG. 9D shown as a test example described below.

After the fluctuation waveform steep gradient portion extending along the slope line Y has occurred, when entrance into a sleep onset occurs, the base line E does not return to the position of the base line D, and the amplitudes P and Q become small, so that the determination utilizing the frequency fluctuation time-series waveform of this embodiment can specify the sleep-onset point C clearly.

When such a sleep-onset point C is specified, it is necessary to specify a point at which the fluctuation waveform steep gradient portion (the steep gradient portion extending along the slope line Y) emerges in the frequency fluctuation time-series waveform. For this specification, for each subject, a sleepiness state when he/she has reached a sleep onset, and a frequency fluctuation time-series waveform and a frequency slope time-series waveform at an entrance time of sleep onset are measured to be stored in a storage section of the computer as teaching data. The teaching data includes a fluctuation waveform steep gradient portion which has occurred just before each subject reaches a sleep onset, namely, when each subject has become conscious of sleepiness at an entrance time of sleep onset, as data. Therefore, the fluctuation waveform steep gradient portion in the teaching data is compared with the frequency fluctuation time-series waveform outputted by the frequency fluctuation time-series analyzing and computing means 613. As a result, when a steep gradient waveform occurs in the frequency fluctuation time-series waveform which is being currently measured, whether or not a slope line thereof approximates a slope line of the fluctuation waveform steep gradient portion of the teaching data which has occurred just before the sleep-onset point is determined, and the sleep-onset point is determined according to whether or not the base line position or the amplitude of a waveform emerging thereafter coincides with the above-described conditions. Incidentally, since whether or not the slope line approximates the slope line of the fluctuation waveform steep gradient portion of the teaching data which has occurred just before the sleep-onset point may differ depending on respective persons, setting such as, for example, a difference within 30° or preferably a difference within 20° is made preliminarily. Further, even if the slope line approximates the slope line of the fluctuation waveform steep gradient portion of the teaching data which has occurred just before the sleep-onset point, when the steep gradient waveform only occurs by a slight time, the steep gradient waveform cannot be said to be the fluctuation waveform steep gradient portion emerging just before the sleep-onset point. As shown in FIG. 9D, the fluctuation waveform steep gradient portion emerging just before the sleep-onset point continues for a predetermined time. In the case shown in FIG. 9D, the steep gradient waveform occurs for about 200 seconds. Accordingly, it is preferred that, for determining whether or not the slope approximates the slope line of the fluctuation waveform steep gradient portion, a time period of occurrence of a steep gradient waveform, for example, a time period such as 30 seconds or more is set preliminarily together with the above-described angles of the slope line.

In this embodiment, as shown in FIG. 6, the waveform determining means 614 is further provided with a sleepiness waveform determining means (sleepiness waveform determining step) 614b. The above-described fluctuation waveform steep gradient portion (the slope line Y in FIG. 9D) occurs in the frequency fluctuation time-series waveform just before the sleep-onset point. On the other hand, as apparent from FIG. 9D, it is considered that the frequency slope time-series waveform indicates a foresight of the frequency fluctuation time-series waveform. That is, a point A and a point B on the frequency slope time-series waveform mean points indicating foresights where the frequency decreases from a point "a" and a point "b" in the frequency fluctuation time-series waveform. Therefore, when the fluctuation waveform steep gradient portion rapidly descending from the point "a" or the point "b" in the frequency fluctuation time-series waveform is detected, whether or not a slope waveform steep gradient portion approximately parallel to the fluctuation waveform steep gradient portion is present in the frequency slope time-series waveform prior to emergence of the fluctuation waveform steep gradient portion is determined. In the case shown in FIG. 9D, it is found that a slope waveform steep gradient portion rapidly descending after emergence of the point A or the point B which is a top point on an upper side of the cycle is present. Therefore, the sleepiness waveform determining means 614a is set such that, when the slope line Y of the fluctuation waveform steep gradient portion of the frequency fluctuation time-series analyzing and computing means 613 is approximately parallel to the slope line X of the slope waveform steep gradient portion in the frequency slope time-series waveform just before emergence of the fluctuation waveform steep gradient portion, the waveform at this time is determined as a sleepiness waveform which is a sleepiness state leading to sleep onset. Thereafter, when the base line E of the time-series waveform emerges in a downward sloping manner in the frequency fluctuation, the sleep-onset point is specified as described above, so that determination about whether or not the base line E emerges in the downward sloping manner is also important.

Since a time period where the fluctuation waveform steep gradient portion of the frequency fluctuation time-series waveform and the slope waveform steep gradient portion determined by the sleepiness waveform determining means 614b show waveform changes approximately parallel to each other depends on a difference among individuals, it can be preferably set arbitrarily, but it is preferred that the time period is set in a range from 20 to 60 seconds from the tests described later. Regarding whether or not these steep gradient portions are approximately parallel to each other, setting can be made such that when a difference between slope angles (slope angles of the slope lines X and Y) from top points on an upper side to top points on a lower side of two waveforms to be handled falls within 30°, preferably within 15°, these steep gradient portions are determined to be approximately parallel to each other. This is based upon the fact that a slope angle difference between the both (a difference between the slope angles of the slope lines X and Y in FIG. 12D) was about 30° in the case where a subject did not become conscious of sleepiness regardless of occurrence of a waveform with a large amplitude in the test example described later. However, since there is a difference among individuals regarding this setting, it is preferred that an angle range to be set can be adjusted preliminarily.

According to the embodiment, when a person sits on the seat 500, an aortic pulse wave is detected from a dorsal region of the person as a biological signal by the biological signal measuring device 1. The biological body state analyzing device 60 analyzes the detected biological signal by the state analyzing section 610. First of all, a time-series waveform of a frequency in a time-series waveform of the biological signal (aortic pulse wave) is obtained by the frequency computing means 611. Next, using the time-series waveform of the frequency of the biological signal, the frequency slope time-series analyzing and computing means 612 obtains a frequency slope time-series waveform and the frequency fluctuation time-series analyzing and computing means 613 obtains a frequency fluctuation time-series waveform. Then, emergence of the fluctuation waveform steep gradient portion in the frequency fluctuation time-series waveform and emergence of a downward sloping base line of the frequency fluctuation time-series waveform after emergence of the fluctuation waveform steep gradient portion are determined and further a sleep-onset point is specified in the above manner by the sleep onset determining means 614a of the waveform determining means 614.

On the other hand, regarding detection of a sleepiness waveform in the waveform determining means 614, as described above, when the sleepiness waveform determining means 614b detects a fluctuation waveform steep gradient portion in the frequency fluctuation time-series analyzing and computing means 613, the fluctuation waveform steep gradient portion is compared with a frequency slope time-series waveform showing change prior thereto. Whether or not an approximately parallel slope waveform steep gradient portion emerges in the frequency slope time-series waveform over a predetermined or more time period prior to emergence of the fluctuation waveform steep gradient portion is determined. Further, the base line of the frequency fluctuation time-series waveform before emergence of the fluctuation waveform steep gradient portion and the base line of the frequency fluctuation time-series waveform after emergence of the fluctuation waveform steep gradient portion are compared with each other. Then, such a fact is confirmed that the base line after emergence of the fluctuation waveform steep gradient portion emerges in a downward sloping manner. It becomes clear from the confirmation of the downward sloping base line that the above-described fluctuation waveform steep gradient portion indicates a sleepiness waveform.

When the above analysis is performed as test or diagnosis in order to grasp a person's health or sleeping situation, analysis can be performed by the biological body state analyzing device 60 after termination of the measurement performed by the biological signal measuring device 1. That is, the frequency slope time-series waveform, the frequency fluctuation time-series waveform, and the base line of the frequency fluctuation time-series waveform are outputted on the same time axis for a whole measurement time and the sleepiness waveform or the sleep-onset point is then specified so that it can be used for diagnosis for a sleeping situation or the like.

On the other hand, when the biological body state analyzing device 60 is actually mounted on a vehicle and it is applied to a system for detecting a state of a driver to issue an alert, processing for specifying the sleepiness waveform or the sleep-onset point is performed approximately concurrently with detection of a biological signal. That is, setting is made such that an alert is issued just after the above-described approximately parallel steep gradient waveform change continues for the predetermined time period while the frequency slope time-series waveform, the frequency fluctuation time-series waveform, and the base line of the frequency fluctuation time-series waveform are being outputted on the same time axis. Thereafter, setting is made such that, when the slope of the fluctuation waveform steep gradient portion in the frequency fluctuation time-series waveform changes, the downward sloping base line of the frequency fluctuation time-series waveform emerges, and when the sleep-onset point is indicated by the sleep-onset point determining means 614a, an alert having larger stimulation is issued.

Incidentally, in the above-described embodiment, the air packs 10, and the first and second elastic members made of expanded resin beads 20 and 30 configuring the biological signal measuring device 1 are assembled into the automobile seat, but they may be assembled into not only the automobile seat but also into such bedding as a bed, a chair for diagnosis in a hospital facility or the like. Further, in the above-described embodiment, the air pack 10 has been arranged at a position at which an aorta (descending aorta) of a dorsal region is detectable, but it may be disposed at a position at which another artery of a human body is detectable.

TEST EXAMPLE 1

Four healthy Japanese men in their 30s (subjects A to D) were made to sit on the above-described seat 500 and a 30-minutes dozing detecting experiments for the subjects were conducted under a static condition. They were maintained in an eye-opening state for the first 10 to 15 minutes of the start of the experiment and then, they were made to close their eyes. Simultaneously, each subject wore an optical digital pulse volume sphygmograph and an electroencephalograph to measure his digital pulse volume and his brain wave. The measurement results are shown in FIGS. 9A to 12D. In FIGS. 9A to 12D, each of FIGS. 9A, 10A, 11A, and 12A shows time-series waveforms of distribution rates of θ wave, α wave, and β wave of a prefrontal area obtained by the electroencephalograph, each of FIGS. 9B, 10B, 11B, and 12B shows time-series waveforms of an HF component and an LF/HF component obtained from the digital pulse volume, each of FIGS. 9C, 10C, 11C, and 12C shows time-series waveforms of a slope of a power value (finger photoplethysmogram power value slope) and a slope of a maximum Lyapunov exponent (finger photoplethysmogram Lyapunov slope) obtained using the digital pulse volume and explained in Background Art of this text, and each of FIGS. 9D, 10D, 11D, and 12D shows a frequency slope time-series waveform and a frequency fluctuation time-series waveform obtained using a biological signal (air-pack pulse wave) obtained by the biological signal measuring device 1 attached to the seat 500 of the above-described embodiment.

Subject A

Figure 9A:
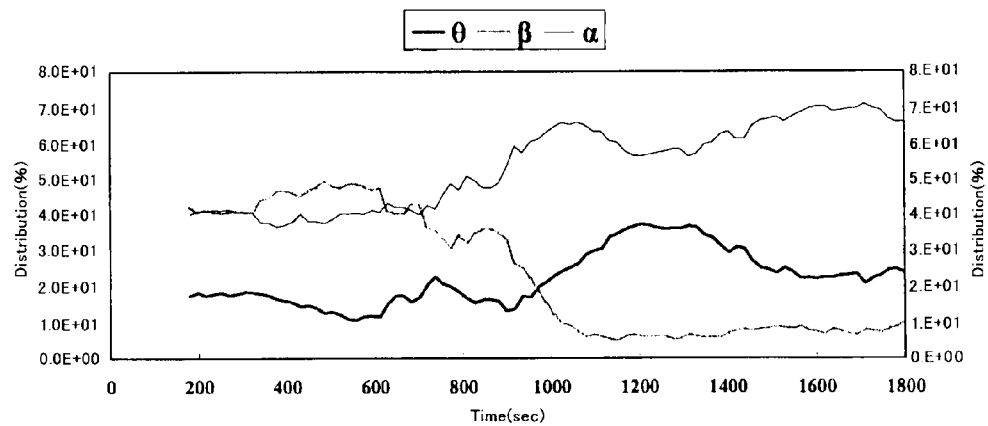
FIG. 9A to FIG. 9D are graphs showing test results of a subject A, FIG. 9A showing time-series waveforms of distribution rates of θ wave, β wave, and α wave of a prefrontal area measured by an electroencephalograph, FIG. 9B showing time-series waveforms of HF component and LF/HF component obtained from a digital pulse volume, FIG. 9C showing time-series waveforms of a slope of a power value (finger photoplethysmogram power value slope) and a slope of a maximum Lyapunov exponent (finger photoplethysmogram lyapunov slope) obtained from the digital pulse volume, and FIG. 9D showing a frequency slope time-series waveform and a frequency fluctuation time-series waveform obtained using an air-pack pulse wave obtained from the biological signal measuring device according to the embodiment.

When the time-series waveform of the brain wave distribution rate shown in FIG. 9A is observed, increase of the distribution rate of α wave and decrease of the distribution rate of β wave in the eyes-closed state after 600 seconds are found. This is because an α wave block was released by eye-closing. Thereafter, increase of the distribution rate of θ wave and decrease of the distribution rate of α wave are confirmed, from which it is thought that the subject A fell asleep together with occurrence of sleepiness after 1050 seconds from the start of the experiment.

Figure 9B:
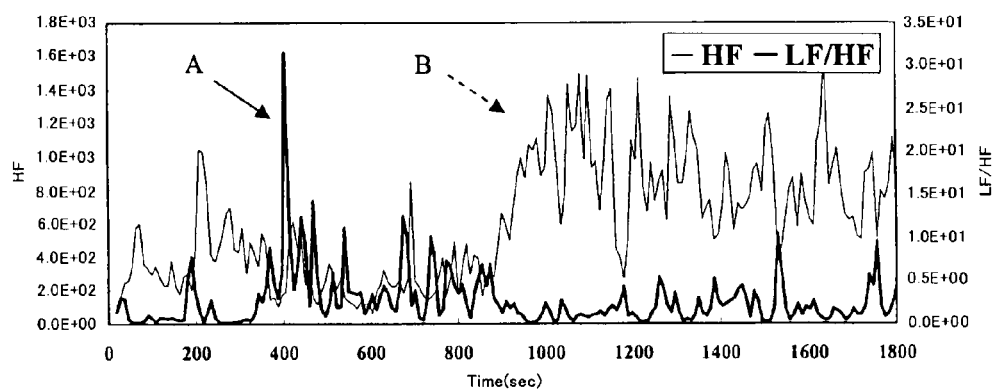

FIG. 9B shows an aspect of fluctuation of the autonomic nerve system of the subject which was captured from a peripheral system of the subject A, where a burst wave of the LF/HF which occurred after 400 seconds from the start of the experiment indicates that a sleep prediction phenomenon occurred before occurrence of the burst wave or in the vicinity thereof. Thereafter, FIG. 9B shows a dominant state of a parasympathetic nerve after about 900 seconds. Accordingly, FIG. 9B suggests that the subject A fell asleep together with occurrence of sleepiness after about 900 seconds.

Figure 9C:
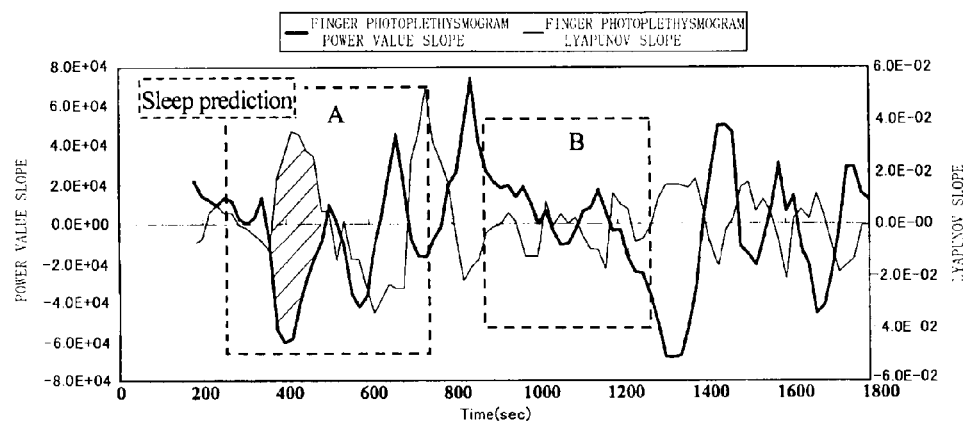
Figure 9D:
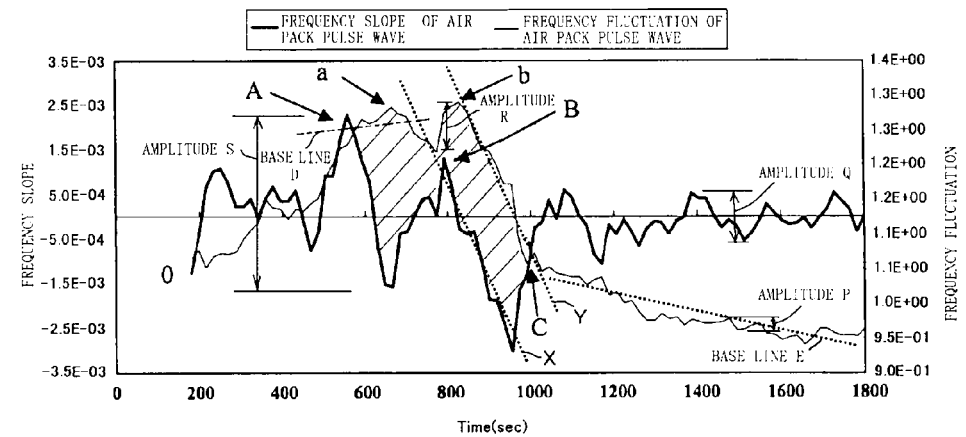

When time-series waveforms of the power value slope and the Lyapunov slope of the digital pulse volume shown in FIG. 9C are observed, an area A surrounded by a broken line indicates that the respective slope time-series waveforms of the power value and the Lyapunov exponent take waveforms having opposite phases having a low frequency and a large amplitude. This indicates that a sleep prediction phenomenon developed in the vicinity of the area A. Thereafter, an area B where the amplitude became small and waveforms with a higher frequency and a smaller amplitude was formed as compared with the time-series waveforms meaning the development of the sleep prediction phenomenon is recognized as a sleep introduction section, from which it is thought that the subject A reached sleep onset in about 10 minutes after development of the sleep prediction phenomenon.

When the frequency fluctuation time-series waveform and the frequency slope time-series waveform of the air-pack pulse wave shown in FIG. 9D are observed, first, the frequency fluctuation time-series waveform of the air-pack pulse wave increases from a point 0 after the start of the experiment, after it temporarily decreases from the vicinity of 680 seconds (point "a"), it increases again from the vicinity of about 800 seconds, and it rapidly decreases from the vicinity of 850 seconds (point "b") and gently decreases from the vicinity of 1050 seconds (point "C"). It is thought that the frequency of the air-pack pulse wave increases due to resistance to sleepiness during a transition from the point 0 to the point "a". It is also thought that the subject A temporarily fell into a relaxed state due to eye-closing and increase of the frequency occurred in a rebounding manner due to temporal occurrence of resistance to sleepiness during a transition from the point "a" to the point "b". It is thought that, since the subject A accepted sleepiness thereafter, the frequency rapidly decreased. The terminal point of the rapid decreasing change is the point "C" and thereafter the base line E of the frequency fluctuation time-series waveform transitions approximately linearly in a downward sloping manner. Therefore, the point "C" can be specified as the sleep-onset point. Further, it is thought that a gentle change after the point "C" indicates a stable state of the heartbeat of the subject A and progress of the sleeping stage.

On the other hand, it is thought that the frequency slope time-series waveform indicates a foresight of the frequency fluctuation waveform. That is, the point A and the point B on the frequency slope time-series waveform means points indicating foresights at which the frequency decreases from the points "a" and "b" on the frequency fluctuation time-series waveform.

The waveform determining means 614 detects the fluctuation waveform steep gradient portion rapidly descending from the point "a" or "b" on the frequency fluctuation time-series waveform and determines whether or not a slope waveform steep gradient portion approximately parallel to the fluctuation waveform steep gradient portion is present in the frequency slope waveform prior to emergence of the fluctuation waveform steep gradient portion. In the case shown in FIG. 9D, after emergence of the point A or the point B which is a top point on an upper side of the cycle, a slope waveform steep gradient portion rapidly descending is present. Further, an approximately parallel waveform change is found for about 60 seconds from the point "a", while an approximately parallel waveform change is found for about 200 seconds from the point "b". As described above, the frequency fluctuation time-series waveform is an index indicating the process of transition to sleeping while the frequency slope time-series waveform indicates change prior to a waveform change of the frequency fluctuation time-series waveform. Therefore, if a time period of approximately parallel waveform changes of the above-described two waveforms reaches a predetermined time period (for example, 30 seconds), a sign indicating imminence of sleep onset can be captured at an early stage where the frequency fluctuation time-series waveform begins to indicate a sign of transition toward sleeping by determining the time point of elapsing of the predetermined time period as a sign indicating imminence of sleep onset. Even if a waveform descending from the point "a" or the point "b" is captured by observing only the frequency fluctuation time-series waveform, the waveform may occur, for example, due to body movement of a person, so that a sleepiness waveform cannot be determined based upon only emergence of the fluctuation waveform steep gradient portion, but since the frequency slope time-series waveform indicates change of the frequency fluctuation time-series waveform beforehand, it is possible to determine a sleepiness waveform early and securely by comparing two waveforms with each other. Further, it is confirmed that the base line E of the frequency fluctuation time-series waveform after emergence of the fluctuation waveform steep gradient portion emerges in a downward sloping manner. It is made clear by confirming the downward sloping base line that the above-described fluctuation waveform steep gradient portion is the sleepiness waveform.

Incidentally, it is understood from change of θ wave in the brain wave distribution rate shown in FIG. 9A or the like that a time band shown by a shaded area in FIG. 9D is a region where the subject A is clearly conscious of sleepiness. On the other hand, it is understood that in a sleep prediction phenomenon shown by a shaded area in the area A shown in FIG. 9C, since a sympathetic nerve is in an increasing state and change in brain wave is poor, a person does not feel sleepiness yet. The air-pack pulse wave is delayed by 7 to 8 minutes as compared with the digital pulse volume capturing an aspect of the reaction of a sympathetic nerve of the peripheral system, and the sleepiness waveform captured by analyzing the air-pack pulse wave according to the method of the present invention develops about 3 minutes before the sleep onset. Since this phenomenon involves sleepiness, it well coincides with a person's sense.

Subject B

When the time series fluctuation of the brain wave distribution rate shown in FIG. 10A is observed, increase of the distribution rate of α wave and decrease of the distribution rate of β wave due to the eye-closing state after 900 seconds are found. This is because an α wave block was released by the eye-closing. Thereafter, increase of the distribution rate of θ wave and decrease of the distribution rate of α wave were confirmed, and occurrence of sleepiness could be confirmed. It is thought that there is a possibility that the subject B fell asleep after 1300 seconds, where θ wave increased.

FIG. 10B shows an aspect of fluctuation of an autonomic nerve, and shows that a burst wave of the LF/HF which occurred after 900 seconds from the start of the experiment indicating that a sleep prediction phenomenon occurred before occurrence of the burst wave or in the vicinity thereof. Thereafter, FIG. 10B shows a dominant state of a parasympathetic nerve after about 900 seconds. Accordingly, it is thought that sleepiness occurred after about 900 seconds.

FIG. 10C shows that a sleep prediction phenomenon developed in the vicinity of an area A surrounded by a broken line. The amplitude further becomes small and an area B in FIG. 10C is a sleep introduction section, so that it is thought that the subject B reached sleep onset when about 10 minutes elapsed after emergence of the sleep prediction phenomenon.

In FIG. 10D, the frequency fluctuation time-series waveform of the air-pack pulse wave shows an ascending tendency up to 400 seconds, then it gently decreases down to the vicinity of about 800 seconds, it temporarily increases from 800 seconds, it rapidly decreases down up to 1100 seconds, and it gently decreases thereafter. It is thought that the subject B was in a tensioned state up to 400 seconds after the start of the experiment but he transitioned to a relaxed state thereafter. It is thought that the frequency increased due to temporal occurrence of resistance to sleepiness in a time period from 800 seconds to 900 seconds. It is thought that decrease of the frequency occurred thereafter because of transition to a relaxed state due to the eye-closing and acceptance of sleepiness.

In FIG. 10D, the frequency slope time-series waveform rapidly descends from a top point on an upper side thereof in the vicinity of 900 seconds, while a rapid descending waveform (fluctuation waveform steep gradient portion) approximately parallel to the frequency slope time-series waveform thereafter occurs on the frequency fluctuation time-series waveform, and an inflection point (sleep-onset point) occurs on the frequency fluctuation time-series waveform in the vicinity of 1100 seconds. That is, the base line of the frequency fluctuation time-series waveform does not return to the base line before emergence of the fluctuation waveform steep slope section to change to small amplitude after 1100 seconds, and the base line shows a downward sloping shape. Further, though the frequency slope time-series waveform changes to small amplitude, it changes to large amplitude after 1600 seconds, from which it is understood that the subject B is wakeful. A shaded area where two waveforms become approximately parallel to each other indicates a sleepiness waveform, so that it is confirmed from FIG. 10A and FIG. 10B that the subject B is clearly conscious of sleepiness at this time point. On the other hand, it is confirmed from FIG. 10A and FIG. 10B that the subject B is not clearly conscious of sleepiness in the sleep prediction phenomenon shown by a shaded area in FIG. 10C. Further, a sleepiness waveform specified by FIG. 10D was developed with a delay of 6 to 8 minutes as compared with the sleep prediction phenomenon of the digital pulse volume shown in FIG. 10C like the case of the subject A.

Subject C

In FIG. 11A, increase of the distribution rate of α wave and decrease of the distribution rate of β wave are found due to the eye-closing state after 900 seconds. Thereafter, occurrence of sleepiness is found. Further, since β wave shows a decreasing tendency after 1100 seconds from the start of the experiment, it is confirmed that sleepiness continuously occurs in the subject C. Further, it is confirmed that the subject C is in a relaxed state owing to a compensating action of a sympathetic nerve, but it can be determined that is not sleeping yet.

A-1, A-2 and A-3 shown in FIG. 11B indicate a burst wave of LF/HF and indicate that an active level of the sympathetic nerve rose after 350 seconds, 900 seconds and 1380 seconds from the start of the experiment. FIG. 11B shows a dominant state of the parasympathetic nerve from about 900 seconds. The dominant state of the parasympathetic nerve indicates an aspect where the subject C felt sleepiness while relaxed.

A shaded region in an area A in FIG. 11C shows development of a sleep prediction phenomenon. Such a fact can be read that the subject C transitioned to a relaxed state thereafter, but it is thought that the subject C did not reach a sleeping state because large decrease of the amplitude of the waveform did not occur. That is, it is thought that the subject C was sleepy but he was in a relaxed state.

Considering the frequency slope time-series waveform and the frequency fluctuation time-series waveform of the air-pack pulse wave shown in FIG. 11D, waveforms with a steep slope occurred in the frequency slope time-series waveform in the vicinity of 250 seconds and in the vicinity of 500 seconds, but an approximately parallel waveform with a steep slope did not occur in the frequency fluctuation time-series waveform thereafter (for example, since a difference between a slope angle of an slope line X between a top portion on an upper side and a top portion on a lower side of a waveform with a large amplitude and a slope angle of an slope line Y of the frequency fluctuation time-series waveform in the vicinity of 250 seconds of the frequency slope time-series waveform is such large as about 25°, it cannot be said that both the slope lines are approximately parallel to each other). Accordingly, the waveform determining means 614 of this embodiment cannot capture a sleepiness waveform. It is thought from the brain wave shown in FIG. 11A that a shaded area shown in FIG. 11D indicates that the subject C is in a relaxed state. It is thought that this is because the amplitude of the frequency slope time-series waveform was relatively large as compared with change of the frequency fluctuation and the active level of the sympathetic nerve rose so that the subject C did not reach a sleeping state. It is thought from this that rising of the active level of the sympathetic nerve serves to reduce the degree of sleepiness. Incidentally, these points coincided with the subject's comment after the experiment. It can be said from FIG. 11D that, even if the frequency slope time-series waveform of the air-pack pulse wave shows the foresight of the frequency fluctuation time-series waveform, the sleepiness waveform cannot be captured accurately by only emergence of the steep gradient portion of the frequency slope time-series waveform.

Subject D

It is confirmed from FIG. 12A that the subject D fell asleep just after the start of the experiment, thereafter wakened again and fell in a relaxed state.

In FIG. 12B, a burst wave near 700 seconds shown by an area A indicates a re-wakening point. Thereafter, a dominant state of a parasympathetic nerve continued from about 1000 seconds.

In FIG. 12C, a shaded region shown by an area A indicates a developed state of a sleep prediction phenomenon, and suggests that the subject D is in a waking state. In an area B near 900 seconds, the amplitude is reduced to cause a micro-sleep, but a large amplitude reduction does not occur so that the subject D is in a relaxed state.

Though the frequency fluctuation time-series waveform of the air-pack pulse wave shown in FIG. 12D is high just after the start of the experiment, thereafter it gradually decreases, from which it is understood that a dominant state of a parasympathetic nerve was maintained just after the start of the experiment and the subject D gradually entered a relaxed state. Though portions of the frequency fluctuation time-series waveform and the frequency slope time-series waveform approximately parallel to each other are slightly present in the vicinity of 900 to 1000 seconds in a region indicated by A, the amplitudes of the frequency fluctuation time-series waveform and the frequency slope time-series waveform do not decrease and fluctuations of the base lines thereof do not occur, from which it can be estimated that micro-sleep occurred in the vicinity of 900 seconds but after temporal re-waking, the subject D transitioned to a relaxed state.

As shown in FIG. 6, it is preferred that the waveform determining means 614 is further provided with a fatigue state estimating means (fatigue state estimating step) 614f. The fatigue state estimating means 614f compares the frequency slope time-series wave form obtained by the frequency slope time-series analyzing and computing means 612 and the frequency fluctuation time-series waveform obtained by the frequency fluctuation time-series analyzing and computing means 613 with each other and estimates a fatigue state from a degree of a difference between both the waveforms. Specifically, the fatigue state estimating means 614f estimates the case where while the frequency fluctuation time-series waveform involving a predetermined phase delay to the frequency slope time-series waveform (preferably, a phase delay of 30 to 180 seconds), an initial phase angle, a phase difference, an amplitude, and an angular frequency transition approximately similarly as a fatigue-free state (well state). That is, the case where while a proper biological fluctuation is maintained, a frequency fluctuation time-series waveform similar to a frequency slope time-series waveform serving as a foresight is produced with a delay from the frequency slope time-series waveform is estimated as a fatigue-free state (well state). According to whether or not a predetermined or more change to the well state occurred in at least one item of the initial phase angle, the phase difference, the amplitude, and the angular frequency, the fatigue state can be estimated according to rank (for example, a state where a compensating action of sympathetic nerve serves, a state where a person does not reach sleep onset but is conscious of sleepiness, and the like).

Figure 13A:
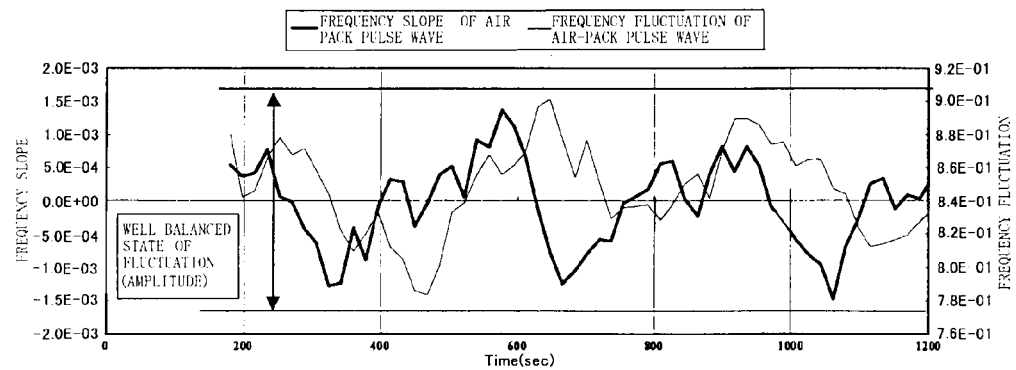
FIGS. 13A to 13C are graphs showing one example of a fatigue estimation result of a well state (a fatigue-free state), FIG. 13A showing a frequency slope time-series waveform and a frequency fluctuation time-series waveform of an air-pack pulse wave, FIG. 13B showing time-series waveforms of distribution rates of θ wave, β wave, and α wave of a prefrontal area measured by an electroencephalograph, and FIG. 13C showing time-series waveforms of HF component and LF/HF component obtained from a digital pulse volume.
Figure 13B:
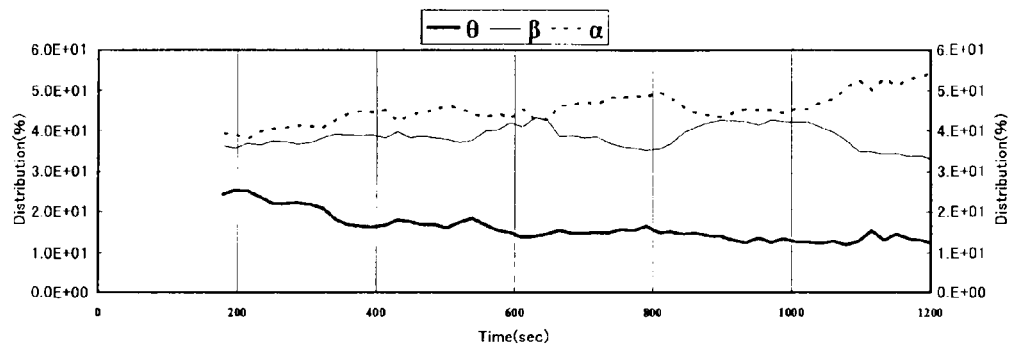
Figure 13C:
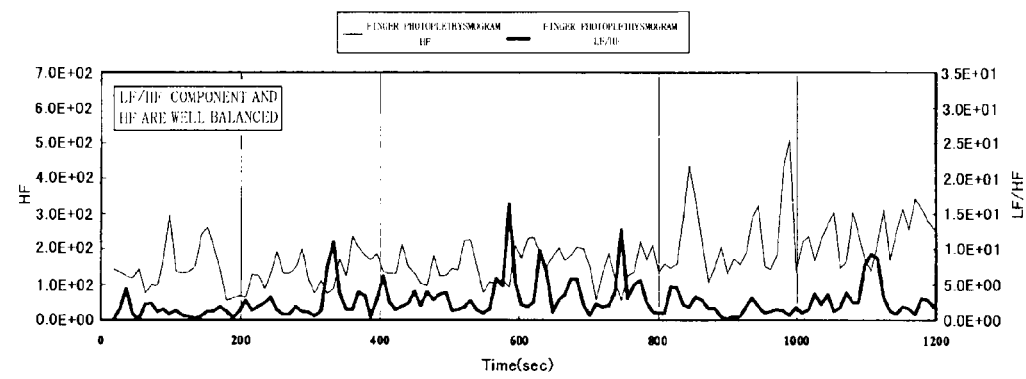

FIG. 13A to FIG. 17C show specific fatigue states estimated by the fatigue state estimating means 614f according to rank. Each case is considered disregarding high-frequency noise signals. In FIG. 13A, first of all, a frequency fluctuation time-series waveform transitions involving a phase delay of about 60 to 150 seconds to a frequency slope time-series waveform. Further, both the waveforms have amplitudes approximately equal to each other and have good balances regarding plus and minus, and they are also approximately similar to each other regarding the initial phase angle, the phase difference, and the angular frequency. It is understood from FIG. 12C that a sympathetic nerve and a parasympathetic nerve are well balanced. Accordingly, it is understood from FIGS. 13A to 13D that a subject is in a fatigue-free well state.

Figure 14A:
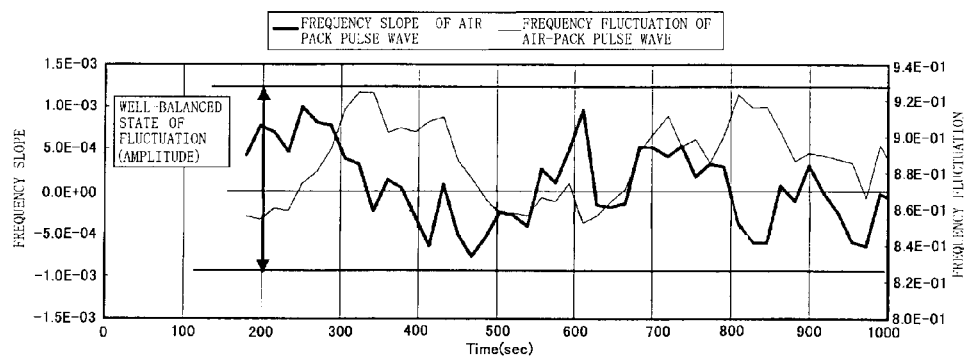
FIGS. 14A to 14C are graphs showing one example of a fatigue estimation result of the case where a compensating action of a sympathetic nerve has occurred after becoming conscious of feeling of fatigue, FIG. 14A showing a frequency slope time-series waveform and a frequency fluctuation time-series waveform of an air-pack pulse wave, FIG. 14B showing time-series waveforms of distribution rates of θ wave, β wave, and α wave of a prefrontal area measured by an electroencephalograph, and FIG. 14C showing time-series waveforms of HF component and LF/HF component obtained from a digital pulse volume.
Figure 14B:
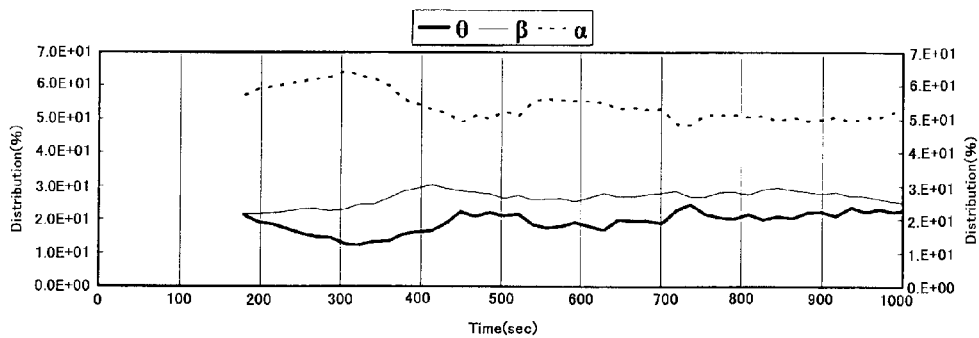
Figure 14C:
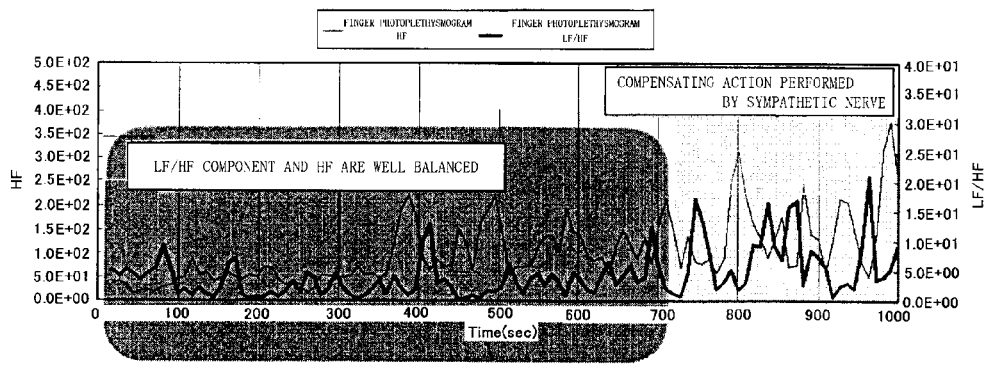

In data shown in FIG. 14A, a frequency fluctuation time-series waveform transitions to the vicinity of 500 seconds with a constant phase delay to a frequency slope time-series waveform, where the amplitudes of both the waveforms are well balanced, but both the waveforms emerge with opposite phases in the vicinity of 800 to 900 seconds, and phase change occurs instead of the constant phase delay. Such a phase change indicates a state that the subject becomes conscious of feeling of fatigue from a state where the subject is not conscious of feeling of fatigue and thereafter the subject does not become conscious of feeling of fatigue due to further occurrence of a compensating action of a sympathetic nerve. When FIG. 14C is observed, it is understood that the sympathetic nerve and the parasympathetic nerve are well balanced up to the vicinity of 700 seconds but a compensating action thereafter occurs due to increase of activity of a sympathetic nerve.

Figure 15A:
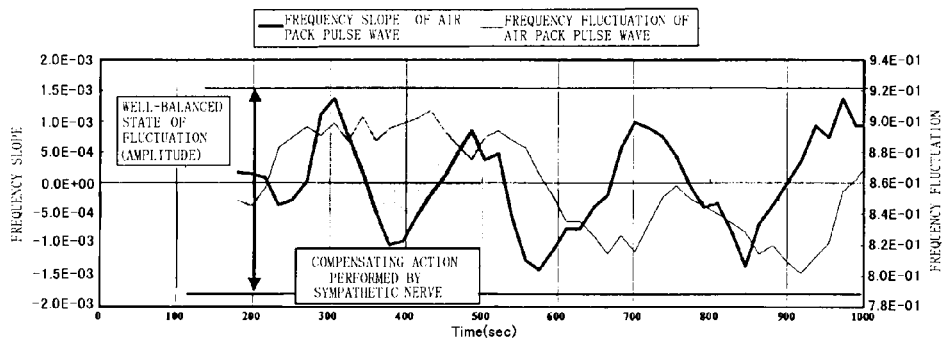
FIGS. 15A to 15C are graphs showing another example of a fatigue estimation result of the case where a compensating action of a sympathetic nerve has occurred, FIG. 15A showing a frequency slope time-series waveform and a frequency fluctuation time-series waveform of an air-pack pulse wave, FIG. 15B showing time-series waveforms of distribution rates of θ wave, β wave, and α wave of a prefrontal area measured by an electroencephalograph, and FIG. 15C showing time-series waveforms of HF component and LF/HF component obtained from a digital pulse volume.
Figure 15B:
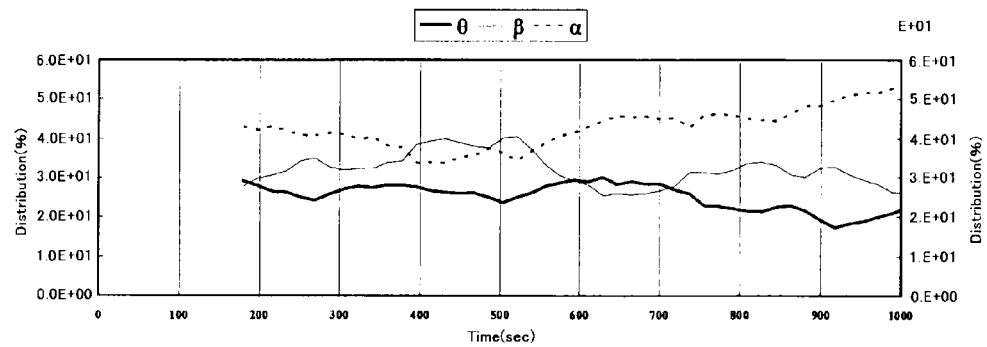
Figure 15C:
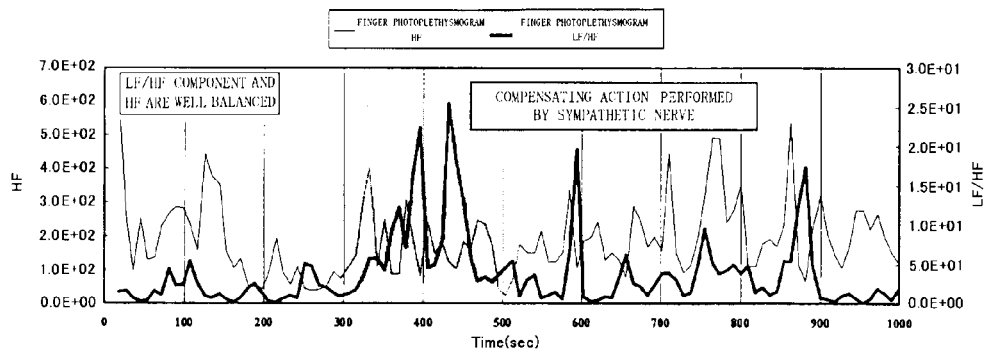

In FIG. 15A, two waveforms transition with opposite phases after 300 seconds, where the subject does not become conscious of feeling of fatigue due to the compensating action of the sympathetic nerve. This is also understood from the fact that the activity of the sympathetic nerve increases after 300 seconds in FIG. 15C.

Figure 16A:
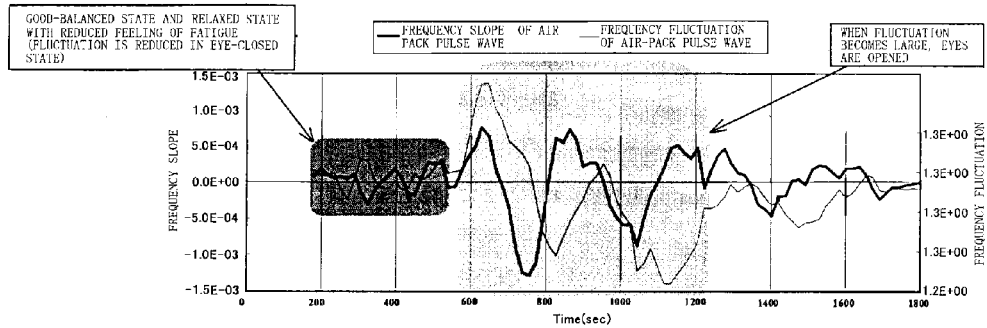
FIGS. 16A to 16C are graphs showing an example of a fatigue estimation result of the state where recovery from fatigue occurs owing to rest, FIG. 16A showing a frequency slope time-series waveform and a frequency fluctuation time-series waveform of an air-pack pulse wave, FIG. 16B showing time-series waveforms of distribution rates of θ wave β, wave, and α wave of a prefrontal area measured by an electroencephalograph, and FIG. 16C showing time-series waveforms of HF component and LF/HF component obtained from a digital pulse volume.
Figure 16B:
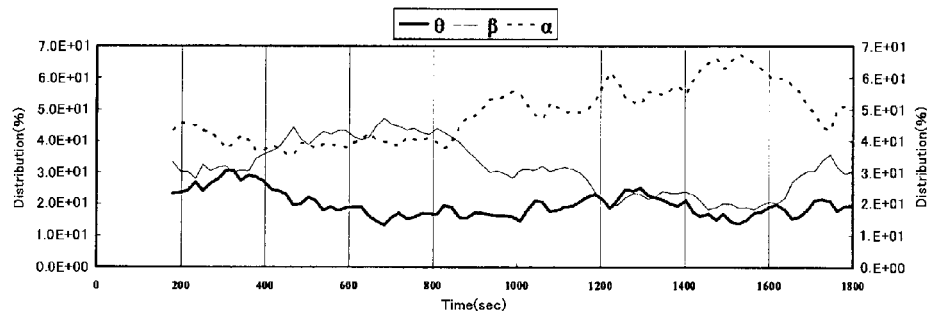
Figure 16C:
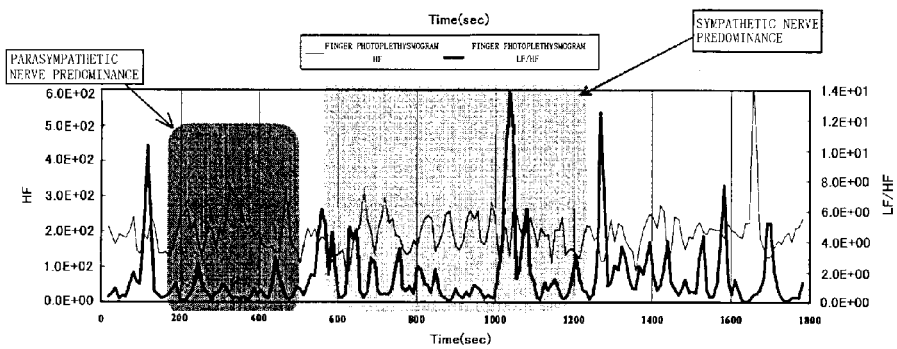

In FIG. 16A, since the subject closes the eyes up to the vicinity of 550 seconds, both the waveforms are small in amplitude so that the subject transitions with a relaxed state with reduced feeling of fatigue and is in a resting (micro-sleep) state. Therefore, after 600 seconds where the subject opens the eyes, both the waveforms become large in amplitude and the frequency fluctuation time-series waveform transitions with a phase delay of about 60 to 150 seconds to the frequency slope time-series waveform, from which it is understood that the subject has relieved fatigue (namely, the subject has returned to the well state).

Figure 17A:
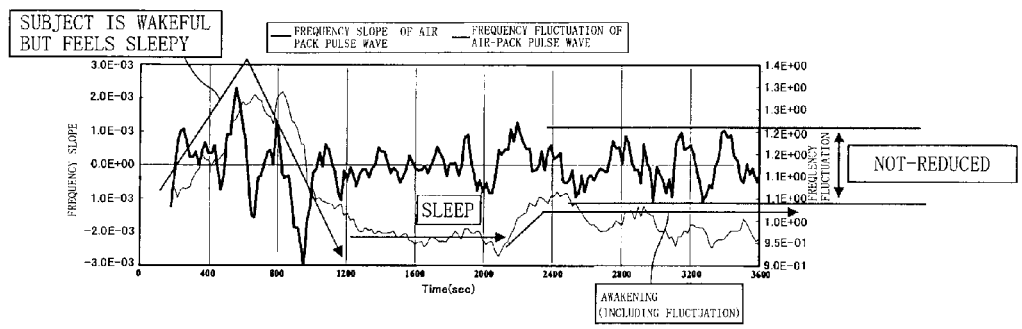
FIGS. 17A to 17C are graphs showing another example of a fatigue estimation result of the state where recovery from fatigue occurs owing to rest, FIG. 16A showing a frequency slope time-series waveform and a frequency fluctuation time-series waveform of an air-pack pulse wave, FIG. 16B showing time-series waveforms of distribution rates of θ wave, β wave, and α wave of a prefrontal area measured by an electroencephalograph, and FIG. 16C showing time-series waveforms of HF component and LF/HF component obtained from a digital pulse volume.
Figure 17B:
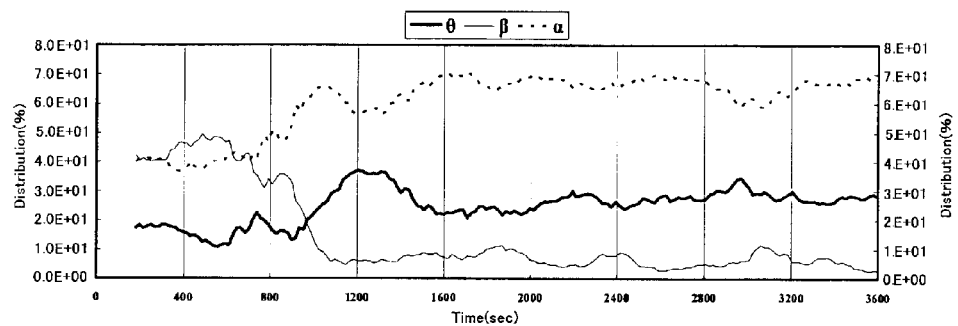
Figure 17C:
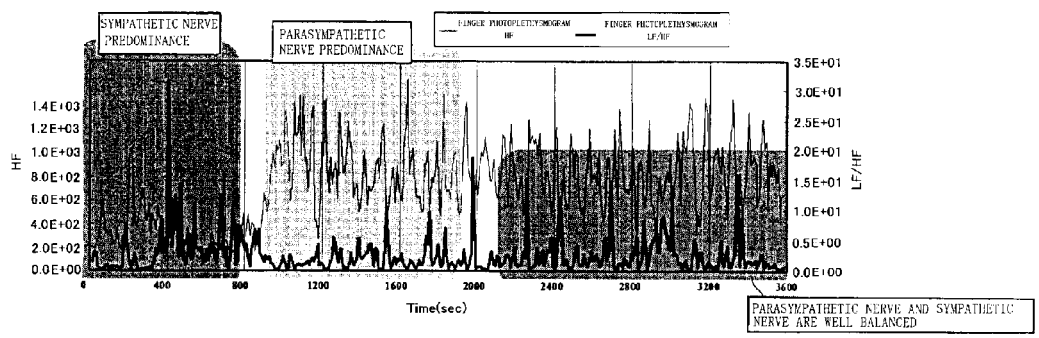

In FIG. 17A, a steep gradient change of the frequency fluctuation time-series waveform occurs in the vicinity of 800 to 900 seconds and a steep slope portion approximately parallel to the steep gradient change of the frequency fluctuation time-series waveform emerges in the frequency slope time-series waveform. Further, the base line of the frequency fluctuation time-series waveform changes to a downward sloping shape from the vicinity of 900 seconds, from which it is understood that the subject fell asleep. The base line of the frequency fluctuation time-series waveform changes to a upward sloping shape in the vicinity of 2000 seconds, and thereafter the frequency fluctuation time-series waveform transitions with a phase delay of about 30 to 100 seconds to the frequency slope time-series waveform, from which it is understood that the subject have relieved fatigue (namely, the subject has returned to the well state). When FIG. 17C is observed, change from a sympathetic nerve predominance to a parasympathetic nerve predominance occurs in the vicinity of 800 seconds where the subject felt sleepiness, and the sympathetic nerve and the parasympathetic nerve are well balanced after 2000 seconds following waking.

As described above, the fatigue state estimating means 614f compares the phases, the amplitudes, or the frequencies of the frequency slope time-series waveform and the frequency fluctuation time-series waveform with each other so that it can make determination about the well state (fatigue-free state), the state where the compensating action of the sympathetic nerve serves, the state where the subject feels sleepiness where the subject does not reach sleep onset, the state where the subject has relieved fatigue owing to rest (micro-sleep), or the state where an error or delay of a reaction time emerges due to fatigue (the sleep-onset point and the sleepiness waveform leading to sleep onset can be determined by the above-described sleep-onset point determining means 614a and sleepiness waveform determining means 614b, respectively, in this embodiment). Incidentally, regarding such a well state (fatigue-free state) that the frequency fluctuation time-series waveform transitions with a predetermined phase delay to the frequency slope time-series waveform and both waveforms have amplitudes approximately equal to each other and frequencies approximately equal to each other, there is a difference among individuals regarding the degree of the phase delay, the magnitude of the amplitude, the frequency and the like. Therefore, regarding the degree of the phase delay, the magnitude of the amplitude, the frequency and the like in the well state (fatigue-free state), it is preferred that a configuration where teaching data is prepared for each individual, it is stored in the computer, and a fatigue state is estimated by comparing actual measured data and the teaching data with each other is adopted.

Further, in order to estimate the fatigue state more clearly, without using the frequency slope time-series waveform obtained from the frequency slope time-series analyzing and computing means 612 and the frequency fluctuation time-series waveform obtained from the frequency fluctuation time-series analyzing and computing means 613 as they are, the above-described estimation of the fatigue state can be performed by obtaining at least one simple-harmonic motion sinusoidal model of the frequency slope time-series waveform and at least one simple-harmonic motion sinusoidal model of the frequency fluctuation time-series waveform from these waveforms and using the at least one simple-harmonic motion sinusoidal model of the frequency slope time-series waveform and the at least one simple-harmonic motion sinusoidal model of the frequency fluctuation time-series waveform. That is, the fatigue state is estimated by comparing the initial phase angles, the phase differences the amplitudes or the angular frequencies of the sinusoidal model of the frequency slope time-series waveform and the sinusoidal model of the frequency fluctuation time-series waveform with each other.

In other words, a frequency slope time-series waveform and a frequency fluctuation time-series waveform are produced from an original waveform of a heartbeat fluctuation obtained from a biological body and a basic harmonic wave obtained when a sympathetic nerve and a parasympathetic nerve are well balanced is identified from these waveforms utilizing Fourier series analysis. Then, a trigonometric function when the sympathetic nerve is dominant (when a burst wave occurs in a wavelet analysis of a digital pulse volume) is identified. Further, a trigonometric function when the parasympathetic nerve is dominant (when rising of a base line of a parasympathetic nerve and a burst wave occur in a wavelet analysis of a digital pulse volume) is identified. The state of a person can be developed as the sum of the series of these trigonometric functions obtained by adding the nth order harmonic wave to the basic harmonic wave and further including effect of an autonomic nerve system.

For example, in the above-described fatigue-free well state shown in FIG. 13A, cyclic functions of the frequency slope time-series waveform and frequency fluctuation time-series waveform can be expressed as the sum of the basic harmonic wave and the nth order harmonic wave. On the other hand, in FIG. 14A, a trigonometric function: $f(t)=\sin 2^t n t/T$ (T=cycle; t=time) is synthesized in the vicinity of 600 to 700 seconds and in the vicinity of 850 to 900 seconds in the frequency slope time-series waveform showing a foresight of the frequency fluctuation time-series waveform and it expresses a compensating action of the sympathetic nerve. In the frequency fluctuation time-series waveform, a trigonometric function where the sympathetic nerve is dominant is similarly synthesized with timing delayed from the frequency slope time-series waveform, namely, in the vicinity of 750 seconds and in the vicinity of 900 to 950 seconds.

Further, a synthesized wave of at least one simple-harmonic motion sinusoidal model of the frequency slope time-series waveform and at least one simple-harmonic motion sinusoidal model of the frequency fluctuation time-series waveform can be obtained from both the waveforms to estimate the fatigue state. The synthesized wave configures one vibration whose amplitude gently increases and decreases, but a vibration waveform of the synthesized wave varies according to whether or not amplitudes, vibration frequencies or the like of simple-harmonic motion sinusoidal models to be synthesized are equal to each other. Therefore, based upon a vibration waveform of a synthesized wave of a fatigue-free state (well state), for example, its state equation is preliminarily obtained and the fatigue state can also be estimated by determining a degree of a difference between a waveform of the synthesized waveform of the fatigue-free state (well state) and a waveform of a synthesized wave to be compared.

Incidentally, the method for obtaining a sinusoidal model from the frequency slope time-series waveform obtained from the frequency slope time-series analyzing and computing means 612 and the frequency fluctuation time-series waveform obtained from the frequency fluctuation time-series analyzing and computing means 613 to use this sinusoidal model can also be used in the above-described sleep-onset point determining means 614a and sleepiness waveform determining means 614b.

Figure 18:
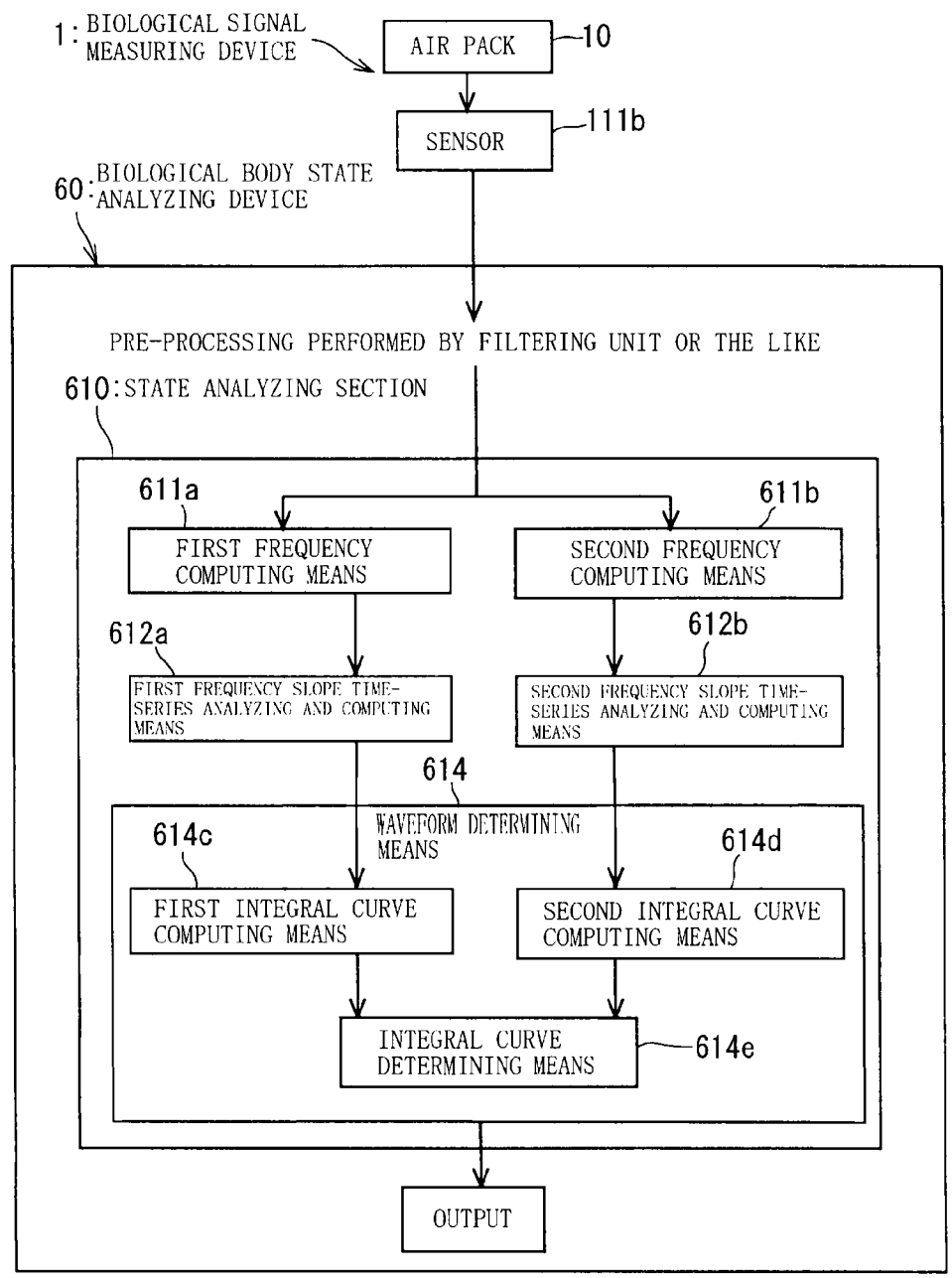
FIG. 18 is a diagram showing a configuration of the biological body state analyzing device according to another embodiment.

FIG. 18 is a diagram showing a main section of another embodiment of a biological body state analyzing device 60 of the present invention. In this embodiment, a first frequency computing means (first frequency computing step) 611a, a second frequency computing means (second frequency computing step) 611b, a first frequency slope time-series analyzing and computing means (first frequency slope time-series analyzing and computing step) 612a, and a second frequency slope time-series analyzing and computing means (second frequency slope time-series analyzing and computing step) 612b which are computer programs are set in the state analyzing section 610, and a first integral curve computing means (first integral curve computing step) 614c, a second integral curve computing means (second integral curve computing step) 614d, and an integral curve determining means (integral curve determining step) 614e are set in the waveform determining means (waveform determining step) 614.

A program for obtaining a time-series waveform of a frequency of a biological signal according to the peak detecting method shown in FIG. 7 is set in the first frequency computing means (first frequency computing step) 611a. That is, as described in the above embodiment, a time-series waveform of an air-pack pulse wave is smoothing-differentiated to obtain a maximum value (peak), the maximum value is obtained for each 5 seconds, reciprocals of time intervals between maximum values (top portions on an upper side of a waveform) of the time-series waveform contained in the 5 seconds are obtained as individual frequencies f, a mean value of the individual frequencies f in the 5 seconds is adopted as a value of a frequency F for the 5 seconds (Step [1] in FIG. 7), and the frequency F obtained for each 5 seconds is further plotted to obtain a time-series waveform of the frequency (Step [2] in FIG. 7).

Figure 8:
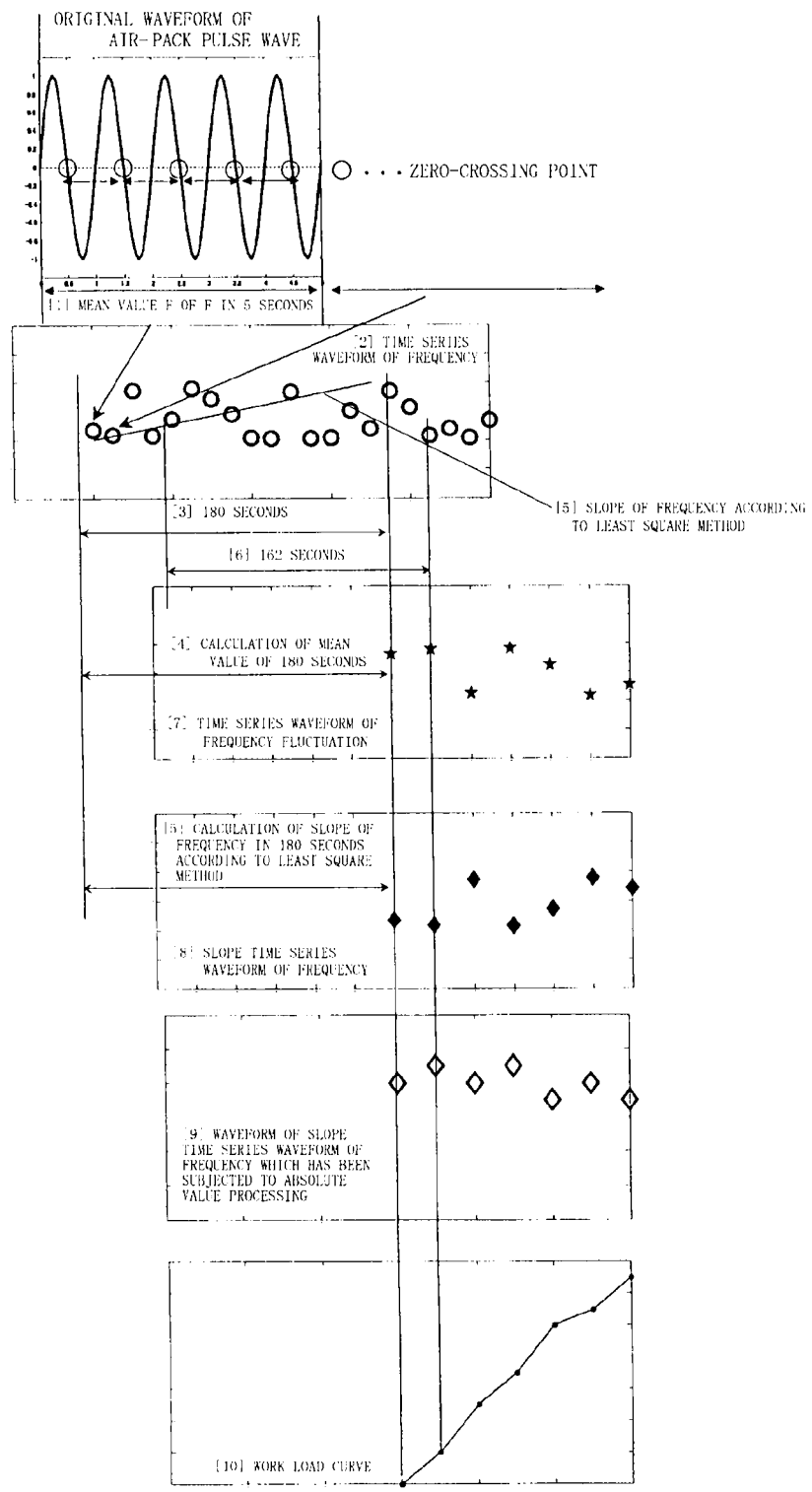
FIG. 8 is a diagram for describing a method for obtaining a frequency fluctuation time-series waveform, a base line of the frequency fluctuation time-series waveform, a frequency slope time-series waveform which is a slope time series of a frequency fluctuation, and an integral curve using a zero-crossing point of a pulse wave (heartbeat fluctuation) detected by the biological signal measuring device.

A program for obtaining a time-series waveform of a pulse wave frequency according to the zero-crossing method shown in FIG. 8 is set in the second frequency computing means (second frequency computing step) 611b. That is, as described in the above-described embodiment, a zero-crossing point at which a positive value changes to a negative value is obtained in the time-series waveform of the air-pack pulse wave, the zero-crossing point is next obtained for each 5 wave, reciprocals of time intervals between the zero-crossing points of the time-series waveform contained in the 5 seconds are obtained as individual frequencies f, a mean value of the individual frequencies f for the 5 seconds is adopted as a value of a frequency F for the 5 seconds (Step [1] in FIG. 8), and the frequency F obtained for each 5 seconds is further plotted to obtain a time-series waveform of the frequency (Step [2] in FIG. 8).

That is, in this embodiment, both the time-series waveforms of the frequency of the biological signal obtained according to two calculation methods of the peak detecting method shown in FIG. 7 and the zero-crossing method shown in FIG. 8 are utilized.

A frequency slope time-series waveform according to the peak detecting method is obtained by applying the processing [3], [4], [5] and [8] shown in FIG. 7 to the time-series waveform of the frequency obtained by the first frequency computing means 611a in the first frequency slope time-series analyzing and computing means (first frequency slope analyzing and computing step) 612a. A frequency slope time-series waveform according to the zero-crossing method is obtained by applying the processing [3], [4], [5], and [8] shown in FIG. 8 to the time-series waveform of the frequency obtained by the second frequency computing means 611b in the second frequency slope time-series analyzing and computing means (second frequency slope time-series analyzing and computing step) 612b.

The first integral curve computing means (first integral curve computing step) 614c applies an absolute value processing to the frequency slope time-series waveform obtained in the first frequency slope time-series analyzing and computing means 612a to integrate the same (the processing [9] and [10] in FIG. 7), while the second integral curve computing means (second integral curve computing step) 614d applies an absolute value processing to the frequency slope waveform obtained in the second frequency slope computing means 612b to integrate the same (the processing [9] and [10] in FIG. 8).

The integral curve determining means (integral curve determining step) 614e outputs the integral curve which is obtained by applying the absolute value processing to the frequency slope time-series waveform based upon the peak detecting method from the first integral curve computing means 614c and the integral curve which is obtained by applying the absolute value processing to the frequency slope time-series waveform based upon the zero-crossing method from the second integral curve computing means 614d on the same time axis and compares them with each other.

In comparison between two integral curves performed by the integral curve determining means 614e, measurement data of 20 samples is collected and considered, and a shape pattern of the integral curve is specified in the following manner.

Figure 19:
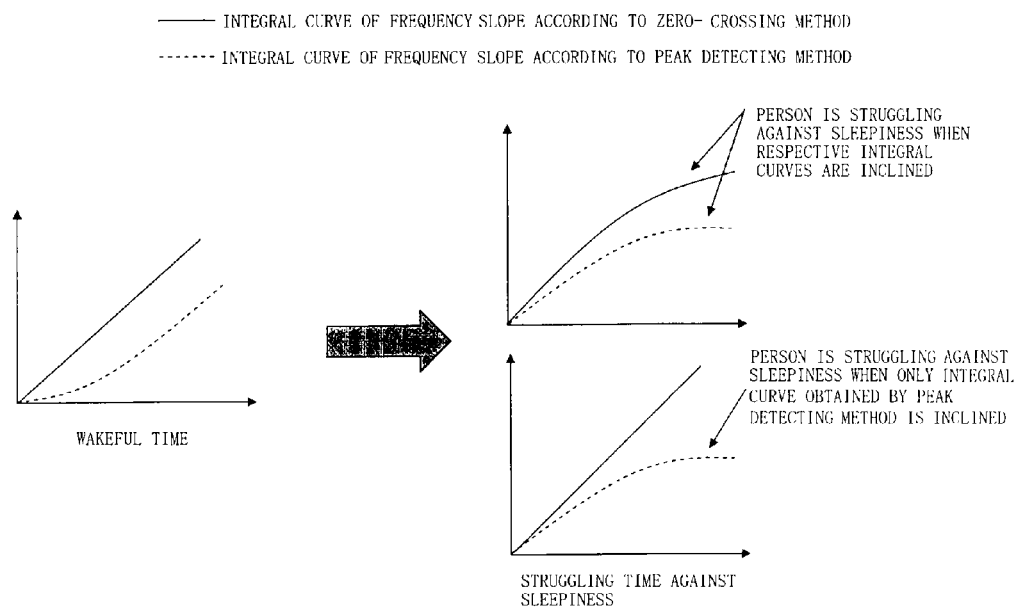
FIG. 19 is a diagram for describing a method for determining an integral curve in a dominant state of a sympathetic nerve.

As shown in FIG. 19, first of all, the case where the integral curve which is obtained by applying the absolute value processing to the frequency slope time-series waveform according to the zero-crossing method from the second integral curve computing means 614d transitions with a value higher than that of the integral curve which is obtained by applying the absolute value processing to the frequency slope time-series waveform according to the peak detecting method from the first integral curve computing means 614c indicates a dominant state of the sympathetic nerve. Then, the case where both the two integral curves or the integral curve according to the peak detecting method changes to have a smaller value with time from the shape of a wakeful time indicates such a state that a person is struggling against sleepiness.

Figure 20:
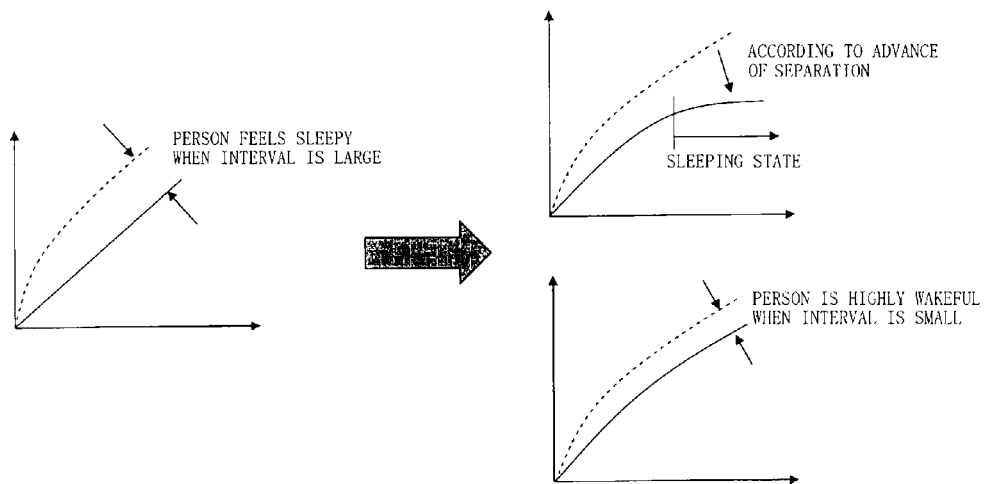
FIG. 20 is a diagram for describing a method for determining an integral curve in a dominant state of a parasympathetic nerve.

As shown in FIG. 20, inversely with the case shown in FIG. 19, the case where the integral curve which is obtained by applying the absolute value processing to the frequency slope time-series waveform according to the peak detecting method from the first integral curve computing means 614c transitions with a value higher than that of the integral curve which is obtained by applying the absolute value processing to the frequency slope time-series waveform according to the zero-crossing method from the second integral curve computing means 614d indicates a dominant state of the parasympathetic nerve. The case where a mutual distance between two integral curves is relatively large indicates a case where a person is in a fatigued state, but the case where the mutual distance is relatively small indicates a case where a person is in a relaxed state and has a high waking degree. The case where the distance between the both is increasing according to time elapsing indicates a case where fatigue of a person proceeds according to the time elapsing.

Figure 21:
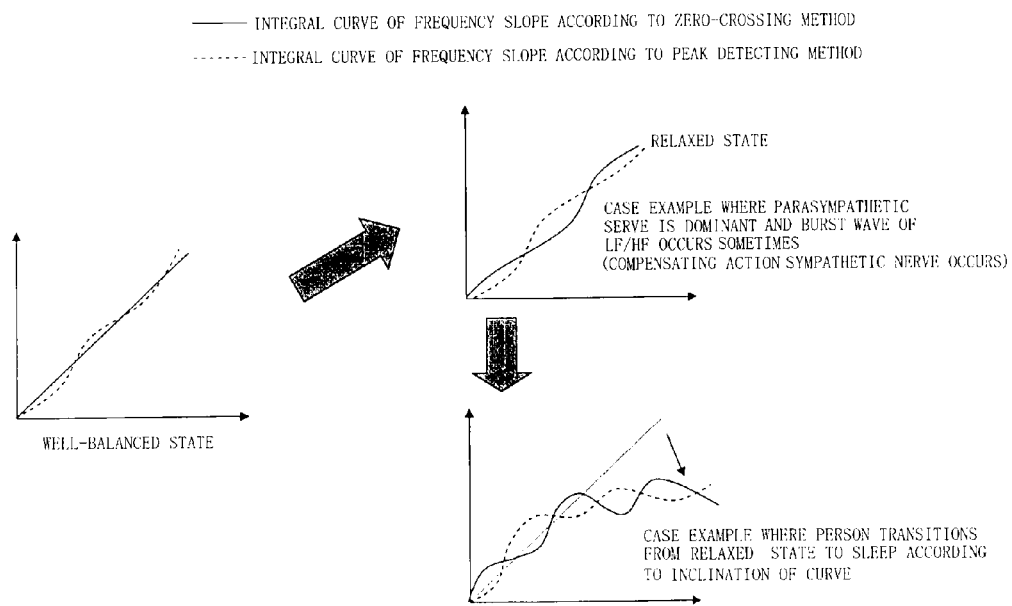
FIG. 21 is a diagram for describing a method for determining an integral curve in a state where a sympathetic nerve and a parasympathetic nerve are well balanced.

As shown in FIG. 21, the case where two integral curves change while intersecting indicates a state where a sympathetic nerve and a parasympathetic nerve are well balanced, the case where two curves intersect but intervals of the intersecting points are expanded indicates a state where a person is in a relaxed state where a parasympathetic nerve is dominant while a compensating action of a sympathetic nerve also occurs, and when two curves intersect but they are inclined according to time elapsing, it is predicted that fatigue occurs in a person from a relaxed state and the person transitions to sleep.

The shape patterns of the integral curves shown in FIG. 19 to FIG. 21 are stored in the storage section of the computer in advance. After the integral curve determining means 614e outputs the integral curve which is obtained by applying the absolute value processing to the frequency slope time-series waveform based upon the peak detecting method from the first integral curve computing means 614c and the integral curve which is obtained by applying the absolute value processing to the frequency slope time-series waveform based upon the zero-crossing method from the second integral curve computing means 614d on the same time axis, it compares the outputted shape pattern with the respective shape patterns shown in FIG. 19 to FIG. 21 stored in the storage section and makes determination about one of the respective shape patterns closer to the output shape pattern to output the determination result.

TEST EXAMPLE 2

The above-described biological signal measuring device, the air pack, and the like were set in a seatback section of a driver's seat of a large truck, real vehicle experiments were conducted, an integral curve which was obtained by applying an absolute value processing to a frequency slope time-series waveform based upon the peak detecting method and an integral curve which was obtained by applying an absolute value processing to a frequency slope time-series waveform based upon the zero-crossing method were outputted on the same time axis and determination of shape patterns was made. Determination results of respective subjects are shown in FIG. 22 to FIG. 25. In FIG. 22 to FIG. 25, 6 stages from the state where a subject is in the most relaxed state where the parasympathetic nerve is dominant to the state where a subject is in the most tensioned state where the sympathetic nerve is dominant are shown in a separated manner based upon the shape patterns shown in FIG. 19 to FIG. 21 in order to make the determination easily viewable. Incidentally, the experiment conditions are as follows:

Experiment vehicle: HINO PROFIA 20t
Experiment Section: Between Tokyo and Osaka (about 520 kilometers)
Experiment time: 21:00 pm to 4:00 am
Experiment term: February to April
Subjects: four (men in 30s to 40s)

Figure 22:
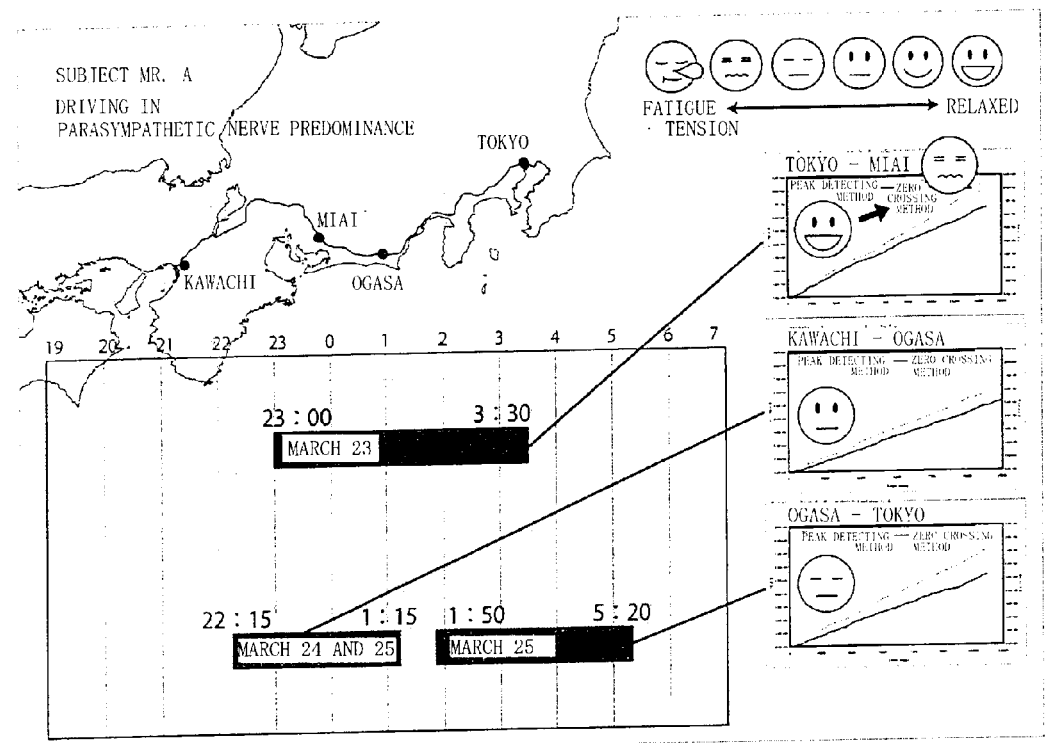
FIG. 22 is a diagram showing a determination result of the subject A in a test example 2.
Figure 23:
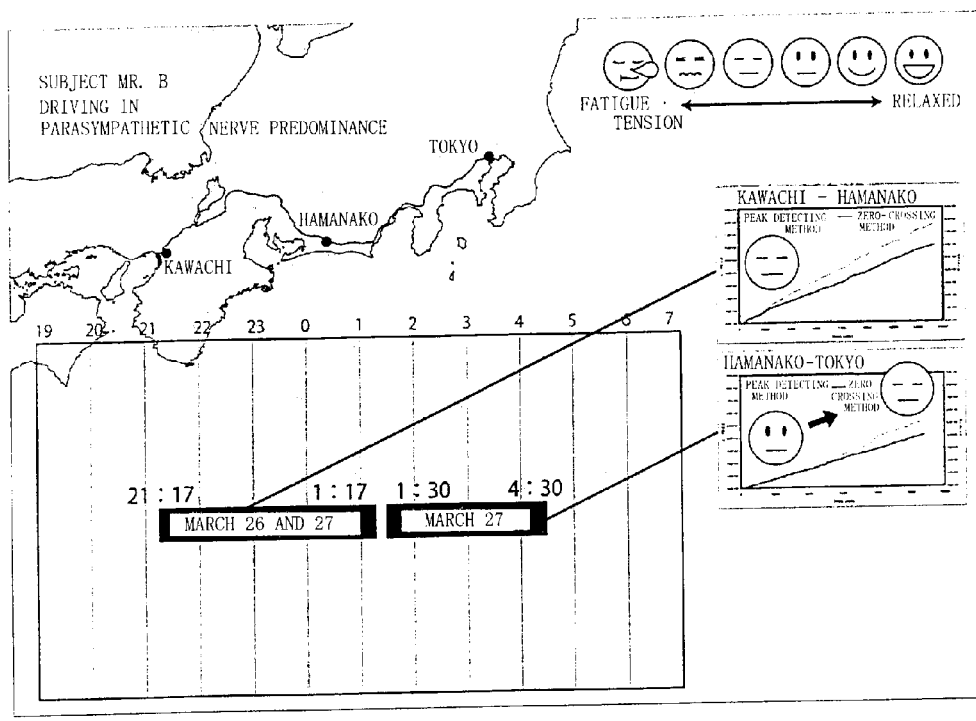
FIG. 23 is a diagram showing a determination result of the subject B in the test example 2.
Figure 24:
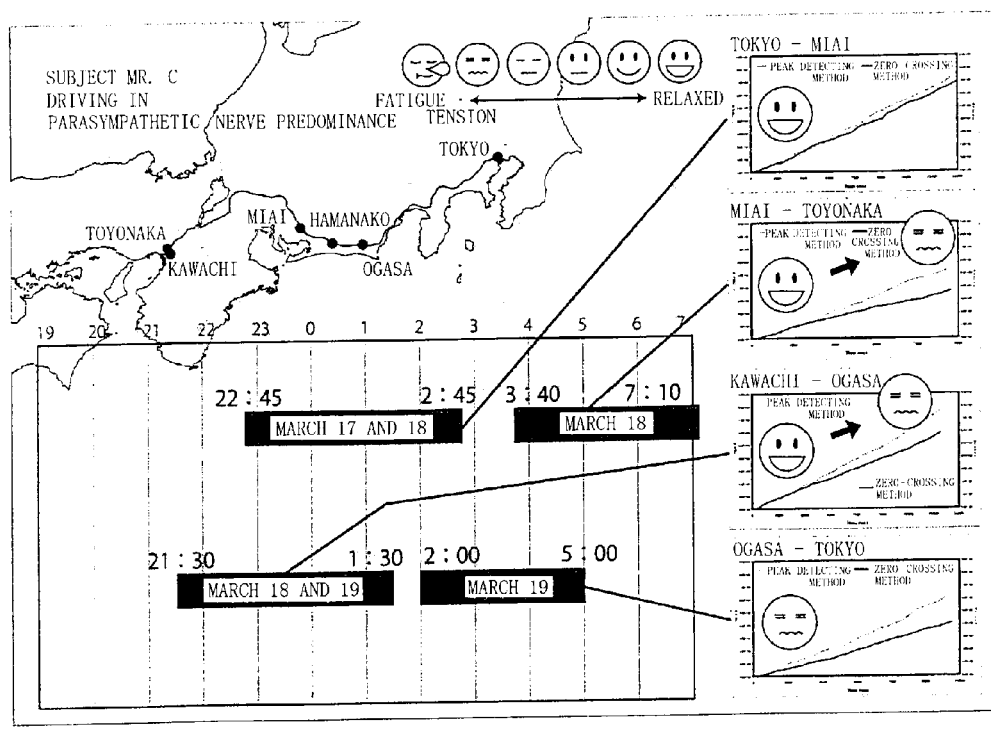
FIG. 24 is a diagram showing a determination result of the subject C in the test example 2.
Figure 25:
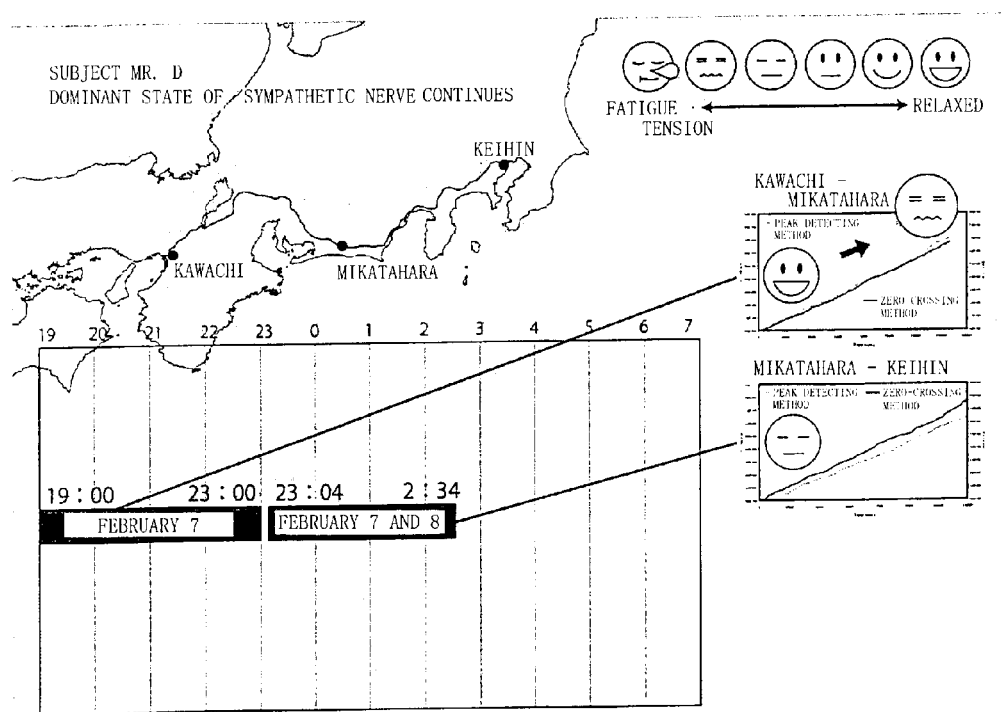
FIG. 25 is a diagram showing a determination result of the subject D in the test example 2.
Figure 26A:
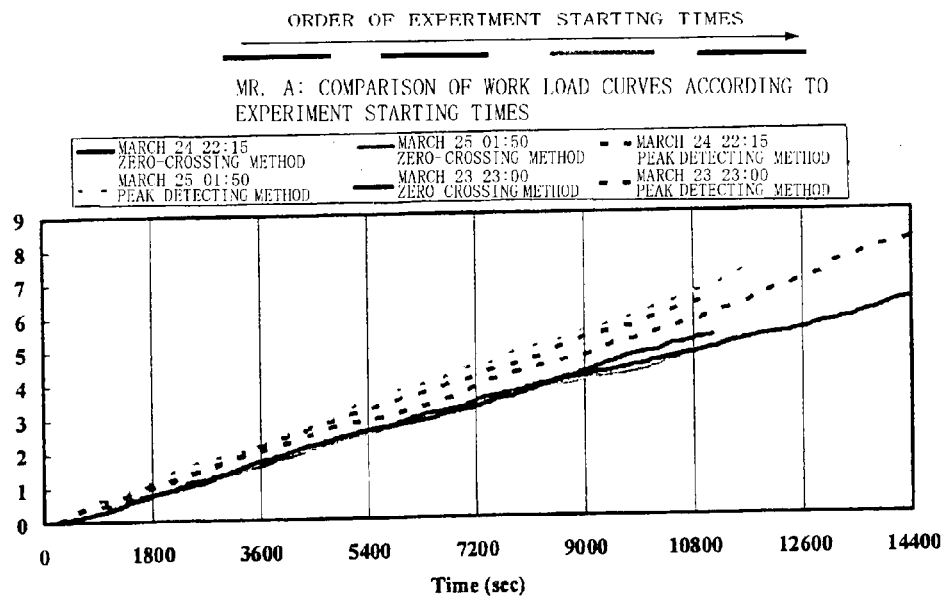
FIGS. 26A to 26D are graphs depicting integral curves of the respective subjects according to the order of experiment starting times, FIG. 26A showing a graph of the subject A, FIG. 26B showing a graph of the subject B, FIG. 26C showing a graph of the subject C, and FIG. 26D showing a graph of the subject D.
Figure 26B:
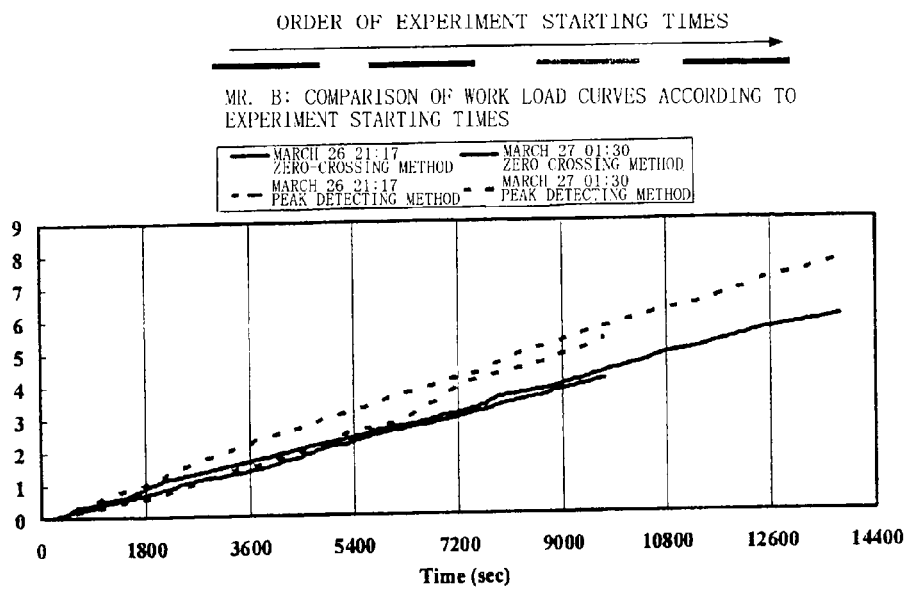
Figure 26C:
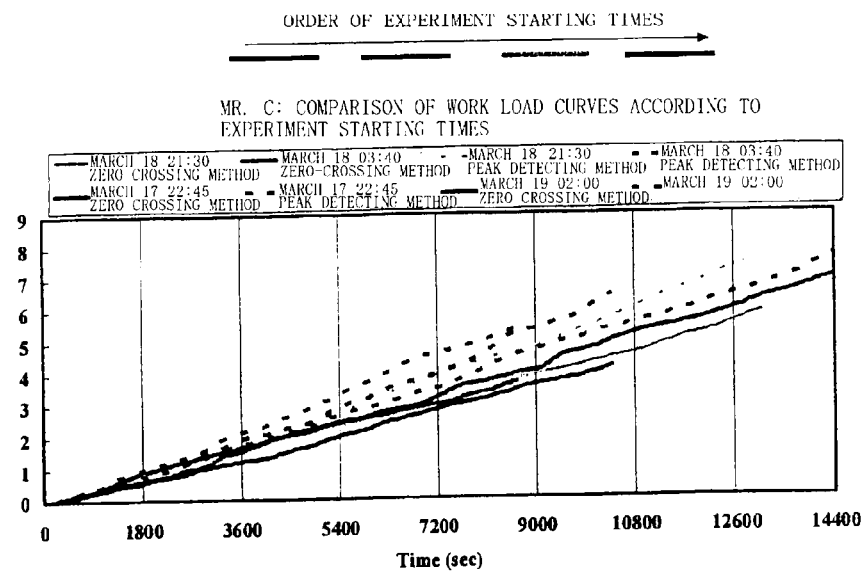
Figure 26D:
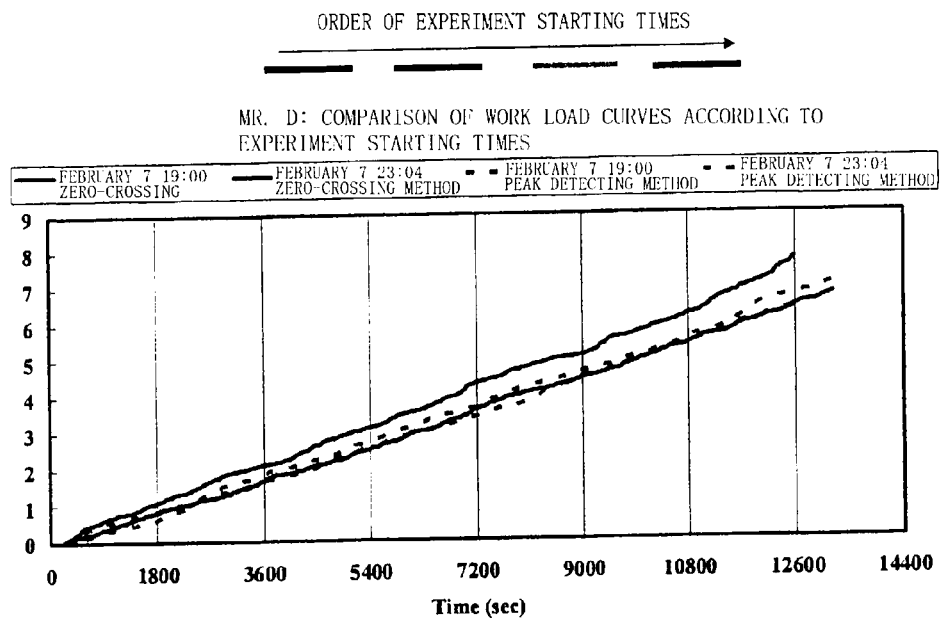

From FIG. 22 to FIG. 24, it can be determined that all subjects A, B and C were driving in their relaxed states where a parasympathetic nerve was dominant as a whole. It can be determined that subject D shown in FIG. 25 was slightly in a state where a sympathetic nerve was dominant and he was driving in a slightly tensioned state. Though they were driving over a long distance, such a state that they were struggling against sleepiness or a state close to a sleeping state as shown in FIG. 19 to FIG. 21 did not occur.

Figure 27:
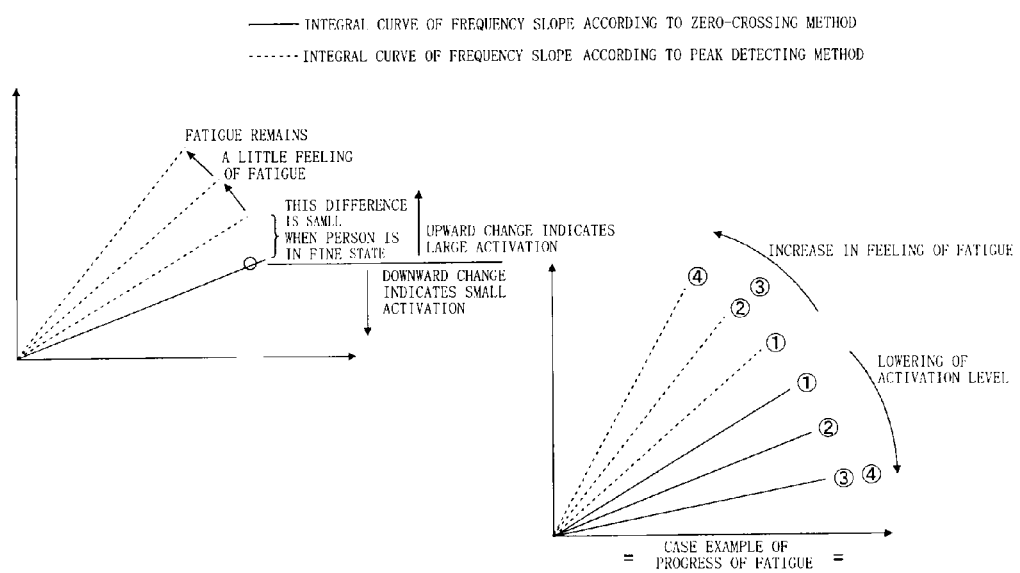
FIG. 27 is a diagram for describing a determining method utilized when a tendency regarding a homeostatic function is determined from an integral curve obtained by a peak detecting method and an integral curve obtained by a zero-crossing method.

Graphs of integral curves of respective subjects which were illustrated according to the order of experiment starting time are shown in FIG. 26. From this figure, it is found that respective outputting positions of the integral curve according to the peak detecting method and the integral curve according to the zero-crossing method were different according to the experiment starting times. It is thought that this is because the respective subjects' homeostatic functions change according to their daily driving. When these results are classified to respective tendencies, the result shown in FIG. 27 is obtained. That is, it can be determined that the smaller the difference between two integral curves, the higher the homeostatic function becomes, which results in good shape. On the other hand, it can be determined that when the integral curve according to the zero-crossing method changes upwardly according to time elapsing, the activation level is increased but when it changes downward, the activation level is decreased. Further, it can be determined that upward change of the integral curve according to the peak detecting method indicates increase of fatigue.

By performing comparisons according to the order of the experiment starting times in this manner, a time band where, a driver can maintain better shape when he/she starts can also be determined.

Incidentally, it is preferred that the biological body state analyzing device 60 is linked to an alert apparatus (sound, vibrations of a seat, inclining motion of a seatback, or the like) provided in a driver's seat. For example, such a configuration can be adopted that the sleepiness state, the fatigued state, or the like described in the above-described respective embodiments is estimated, and when the state leads to a predetermined stage, the alert apparatus (sound, vibrations of a seat, inclining motion of a seatback, or the like) is activated to cause the driver to return to his/her wakeful state. Further, such a configuration can be adopted that a communication apparatus is attached to the biological body state analyzing device 60 and output data of the biological body state analyzing device 60 is transmitted to a computer in a management center which automatically manages operations of trucks or the like. A timing of communication can be set arbitrarily, and such a configuration can be adopted that, when the biological body state analyzing device 60 detects the sleepiness state or the fatigued state described in the above-described respective embodiments, it issues an automatic notification to the management center and an alert is issued from the management center to the driver through the communication apparatus or the above-described alert apparatus provided in the driver's seat is remotely operated from the management center. Further, such a configuration can be adopted that the output data of the biological body state analyzing device 60 is always monitored on the side of the management center and change of the biological body state of the driver or the physical condition thereof is always checked.

Figure 28:
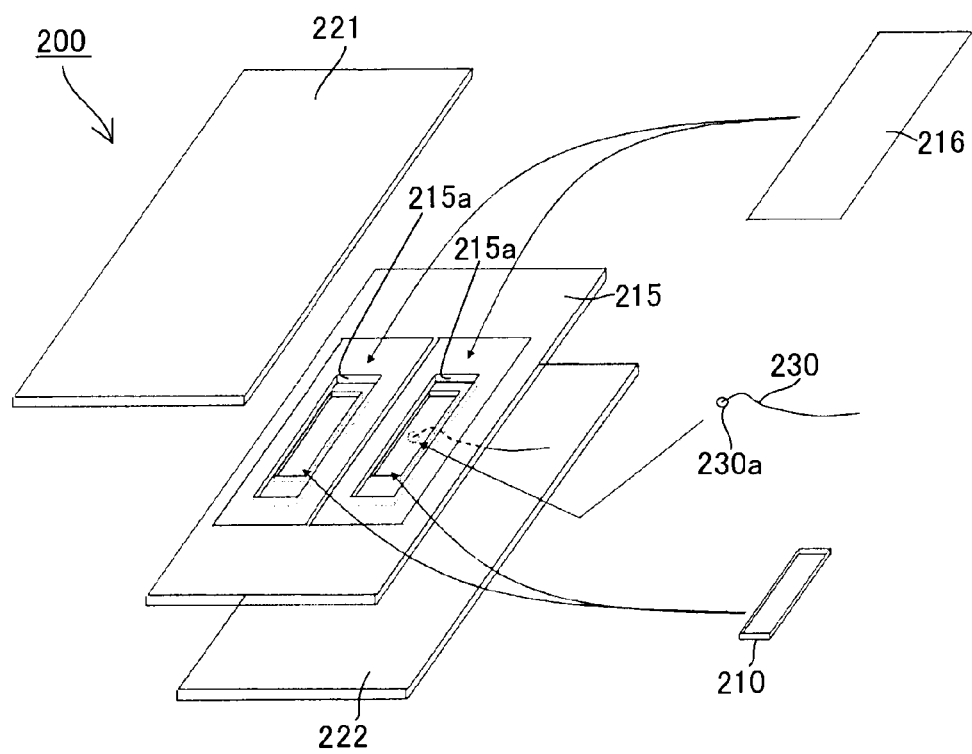
FIG. 28 is a view showing another aspect of the biological signal measuring device to which the present invention can be applied.
Figure 29:
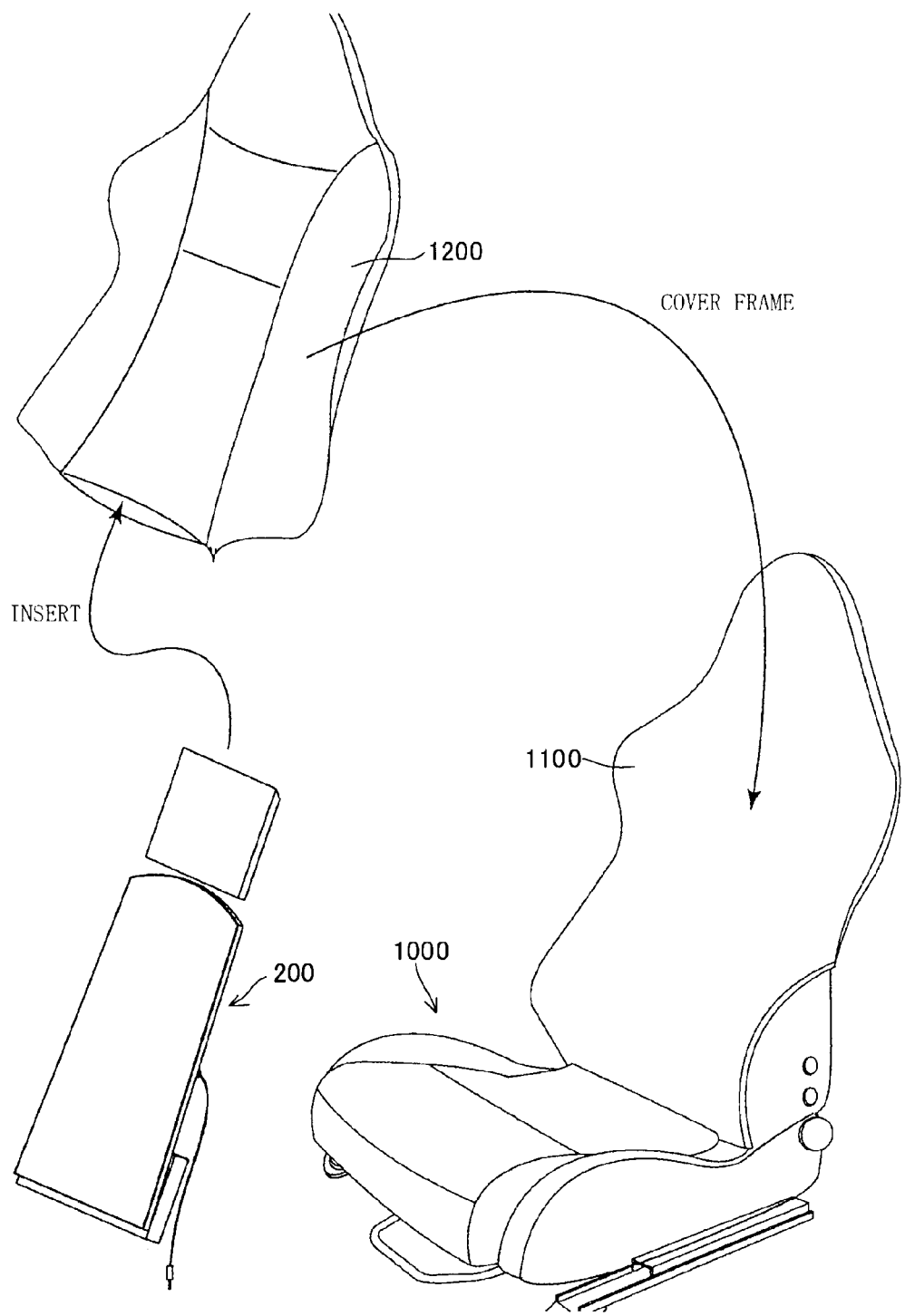
FIG. 29 is a view showing a process for assembling the biological signal measuring device shown in FIG. 28 into a seat.

Further, the biological signal measuring device is not limited to ones using the above-described air pack, but a device shown in FIG. 28 to FIG. 29 can be used. A biological signal measuring device 200 shown in FIG. 28 to FIG. 29 is configured to have a three-dimensional solid knitted fabric 210, a three-dimensional solid knitted fabric supporting member 215, a film 216, plate-shaped expanded bodies 221, 222, and a vibration sensor 230.

As the three-dimensional solid knitted fabric 210, one similar to the material used in the biological signal measuring device 1 shown in FIG. 1 and the like can be used. It is preferred that the three-dimensional solid knitted fabric 210 has a load-deflection characteristic in a thickness direction where when it is placed on a measurement plate and it is pressed by a pressing plate having a diameter of 30 mm or a diameter of 98 mm, a spring constant falls in a range up to a load of 100N and is similar to a load-deflection characteristic of a muscle of the breach of a person. Specifically, it is preferred that a three-dimensional solid knitted fabric having a spring constant which falls in a range of 1 to 5 N/mm when it is pressed by the pressing plate having a diameter of 30 mm or having a spring constant which falls in a range of 1 to 10 N/mm when it is pressed by the pressing plate having a diameter of 98 mm. Since the load-deflection characteristic of the three-dimensional solid knitted fabric 210 is similar to the load-deflection characteristic of the muscle of a person, the three-dimensional solid knitted fabric and the muscle are balanced, so that when a biological signal is transmitted to the three-dimensional solid knitted fabric, the three-dimensional solid knitted fabric vibrates similarly to the muscle of a person, whereby transmission of the biological signal can be performed without causing large damping.

It is preferred that the plate-shaped expanded bodies 221, 222 are composed of expanded bead bodies. As the expanded bead body, for example, an expanded formation body of a resin containing at least one of polystyrene, polypropylene, and polyethylene according to a bead method can be used. The plate-shaped expanded bodies 221, 222 composed of expanded bead bodies transmit a biological signal involving fine vibrations as a membrane oscillation according to characteristics of spherical resin membranes formed of foams constituting individual fine beads. The membrane oscillation is transmitted to the three-dimensional solid knitted fabric as a string vibration, and these membrane oscillation and string vibration are overlapped with each other, so that the biological signal is detected by a vibration sensor 230 described later as a mechanical vibration amplified by overlapping of the membrane oscillation and the string vibration with each other. Accordingly, detection of the biological signal is made easy.

When the plate-shaped expanded bodies 221, 222 are composed of expanded bead bodies, it is preferred that an expansion ratio is in a range of 25 to 50 times and a thickness of the bodies is set to be equal to or less than an average diameter of beads. For example, when an average diameter of beads having an expansion ratio of 30 times is in a range of about 4 to 6 mm, the plate-shaped expanded bodies 221, 222 are sliced cut to have a thickness of about 3 to 5 mm. Thereby, soft elasticity is imparted to the plate-shaped expanded bodies 221, 222, so that a solid vibration resonated with a vibration with small amplitude occurs easily. Incidentally, the plate-shaped expanded bodies 221, 222 may be disposed on both sides of the three-dimensional solid knitted fabric 210 in a sandwiching manner like this embodiment, but such a configuration can be adopted that the plate-shaped expanded body is disposed only on one side of the three-dimensional solid knitted fabric 210, preferably, it is disposed only on the side of the seatback.

Here, as the three-dimensional solid knitted fabric 210, a reed-shaped one having a width of 40 to 100 mm and a length of 100 to 300 mm is used. When a three-dimensional solid knitted fabric 210 having such a size is used, pre-compression (a state where tension occurs in connection stands) occurs easily, and a balanced state between a person and the three-dimensional solid knitted fabric 210 is produced easily. In this embodiment, two three-dimensional solid knitted fabrics are disposed at positions symmetrical to each other so as to sandwich a site corresponding to a backbone in order to reduce a feeling of strangeness when the back of a person abuts on the seatback. It is preferred that such a configuration is adopted in order to dispose the three-dimensional solid knitted fabrics 210 at predetermined positions easily, the three-dimensional solid knitted fabrics 210 are supported by a three-dimensional solid knitted fabric supporting member 215, as shown in FIG. 28. The three-dimensional solid knitted fabric supporting member 215 is formed in a plate shape, and is also formed with two vertically-long through-holes for arrangement 215a, 215a at positions symmetrical to each other so as to sandwich a site corresponding to a backbone. It is preferred that the three-dimensional solid knitted fabric supporting member 215 is composed of a expanded bead body formed in a plate shape like the above-described plate-shaped expanded bodies 221, 222. Preferable expansion ratio and thickness range when the three-dimensional solid knitted fabric supporting member 215 is composed of an expanded bead body are similar to those of the above-described plate-shaped expanded bodies 221, 222. However, it is preferred in order to cause a biological signal to generate membrane oscillation more significantly that the thickness of the plate-shaped expanded bodies 221, 222 disposed above and below the three-dimensional solid knitted fabrics 210, 210 in a stacking manner is thinner than that of the three-dimensional solid knitted fabric supporting member 215.

In a state where two three-dimensional solid knitted fabrics 210, 210 are inserted and disposed in the through-holes for arrangement 215a, 215a formed in the three-dimensional solid knitted fabric supporting member 215, films 216, 216 are stacked on surface sides and back surface sides of the three-dimensional solid knitted fabrics 210, 210. It is preferred that formation positions of the through-holes for arrangement 215a, 215a (namely, arrangement positions of the three-dimensional solid knitted fabrics 210, 210) are set to positions corresponding to regions where fluctuation occurring due to motion involved in pumping of an atrium and an aorta (especially, a descending aorta) and motion of an aorta valve can be detected. As a result, the three-dimensional solid knitted fabrics 210, 210 are sandwiched in their upper and lower faces between the plate-like expanded bodies 221, 222, and peripheral portions thereof are surrounded by the three-dimensional solid knitted fabric supporting member 215, so that the plate-like expanded bodies 221, 222, and the three-dimensional solid knitted fabric supporting member 215 serve as resonant-vibration boxes (resonance boxes).

Further, it is preferred that the three-dimensional solid knitted fabrics 210, 210 thicker than the three-dimensional solid knitted fabric supporting member 215 are used. That is, such a thickness relationship that, when the three-dimensional solid knitted fabrics 210, 210 are disposed in the through-holes for arrangement 215a, 215a, surfaces and back surfaces of the three-dimensional solid knitted fabrics 210, 210 are protruded beyond the through-holes for arrangement 215a, 215a is satisfied. Thereby, when peripheries of the films 216, 216 are made to adhere to peripheral edge portions of the through-holes for arrangement 215a, 215a, the three-dimensional solid knitted fabrics 210, 210 are pressed in a thickness direction thereof, so that tensions are produced due to reaction forces of the films 216, 216, which results in easy occurrence of solid vibration (membrane oscillation) in the films 216, 216. On the other hand, pre-compression also occurs in the three-dimensional solid knitted fabrics 210, 210 and tension due to reaction force also occurs in connecting strands holding a thickness shape of the three-dimensional solid knitted fabric, which results in easy occurrence of string vibration. Incidentally, it is preferred that the films 216, 216 are provided on both sides of the surface sides and the back surface sides of the three-dimensional solid knitted fabrics 210, 210, but such a configuration can be adopted that the films are provided on one sides of the three-dimensional solid knitted fabrics 210, 210. As the films 216, 216, plastic films made of polyurethane elastomer (for example, Product Number "DUS605-CDR" produced by Sheedom Co., Ltd.) or the like can be used.

The vibration sensor 230 is disposed in one three-dimensional solid knitted fabric 210 in a fixed state before stacking of the above-described films 216, 216. The three-dimensional solid knitted fabric 210 is composed of a pair of ground knitted fabrics and connecting strands, but since string vibrations of respective connecting strands are transmitted to the films 216, 216 and the plate-shaped expanded bodies 221, 222 through node points with the ground knitted fabric, it is preferred that a sensing portion 230a of the vibration sensor 230 is fixed to a surface of the three-dimensional solid knitted fabric 210 (a surface of the ground knitted fabric). It is preferred that as the vibration sensor 230, a microphone sensor, especially, a capacitive microphone sensor, is used. In this embodiment, since it is unnecessary to consider a sealing property of a site where the microphone sensor has been disposed (namely, the through-hole for arrangement 215a in which the three-dimensional solid knitted fabric 210 has been disposed), lead wires of the microphone sensor can be wired easily. A vibration of a body surface generated by a biological signal via a muscle of a person is transmitted to not only the three-dimensional solid knitted fabric 210 but also the plate-shaped expanded bodies 221, 222 and the film 216, so that it is amplified due to overlapping of vibrations (string vibration and membrane oscillation) of these members. Therefore, the vibration sensor 230 is not limited to fixation to the three-dimensional solid knitted fabric 210 but the sensing portion 230a thereof may be fixed to the plate-shaped expanded bodies 221, 222 and the film 216 configuring a vibration transmission route.

The above-described biological signal measuring apparatus 200 is arranged inside a skin 1200 covering a seatback frame 1100 of an automobile seat 1000, for example, as shown in FIG. 29. Incidentally, in order to facilitate an arrangement work, it is preferred that the three-dimensional solid knitted fabric 210, the three-dimensional solid knitted fabric supporting member 215, the film 216, the plate-shaped expanded bodies 221, 222, the vibration sensor 230, and the like configuring the biological signal measuring apparatus 200 are unitized in advance.

According to the above-described biological signal measuring apparatus 200, a membrane oscillation occurs in the plate-shaped expanded bodies 221, 222 and the film 216 having the load-deflection characteristic similar to the load-deflection characteristic of a muscle and a string vibration occurs in the three-dimensional solid knitted fabric 210 having the load-deflection characteristic similar to the load-deflection characteristic of a muscle of a person by a biological signal. Then, the string vibration of the three-dimensional knitted fabric 210 affects the membrane oscillation of the film 216 and the like again, and these vibration and oscillation serve in an overlapping state. As a result, vibration inputted from a body surface according to occurrence of a biological signal is directly detected by the vibration sensor 230 as a solid vibration amplified due to overlapping thereof with the string vibration and the membrane oscillation.

In the case of the biological signal measuring apparatus 1 which detects air pressure fluctuation within the air pack 10, shown in FIG. 1 and the like, since a volume and pressure are inversely proportional to each other, it is difficult to detect pressure fluctuation unless the volume of a sealing bag is made small. On the other hand, according to the biological signal measuring apparatus 200 shown in FIG. 28 and FIG. 29, since an amplified solid vibration transmitted via the mechanical amplifying device (the three-dimensional solid knitted fabric 210, the plate-shaped expanded bodies 221, 222, and the film 216) is detected instead of the air pressure fluctuation, the volume (cubic volume) of the apparatus is hardly limited from the viewpoint of a detection sensitivity, so that a vibration with small amplitude as an aortic pulse wave can be detected with a high sensitivity. Therefore, the biological signal measuring apparatus 200 can accommodate persons having various physical bodies. Accordingly, the biological signal measuring apparatus 200 shown in FIG. 28 and FIG. 29 can detect a biological signal with a high sensitivity even under such an environment where the apparatus is utilized by persons having various physical bodies and inputted with various external vibrations like an automobile seat.

Reference Signs List
1: biological signal measuring apparatus
10: air pack
11: surface side air pack
111: small airbag
111b: sensor
112: three-dimensional solid knitted fabric
12: back surface side air pack
121: large airbag
122: three-dimensional solid knitted fabric
15: receiving body
100: air-pack unit
20: first elastic member made of expanded resin beads
30: second elastic member made of expanded resin beads
40, 45: three-dimensional solid knitted fabric
500: seat
510: seatback section
511: skin member
512: cushion supporting member
520: seat cushion section
60: biological body state analyzing device
610: state analyzing section
611: pulse wave frequency computing means
611a: first pulse wave frequency computing means
611b: second pulse wave frequency computing means
612: frequency slope time-series analyzing means
612a: first frequency slope time-series analyzing means
612b: second frequency slope time-series analyzing means
613: frequency fluctuation time-series analyzing means
614: waveform determining means
614a: sleep-onset point determining means 614*b*: sleepiness waveform determining means
614*c*: first integral curve computing means
614*d*: second integral curve computing means
614*e*: integral curve determining means
614*f*: fatigue state estimating means
200: biological signal measuring apparatus
210: three-dimensional solid knitted fabric
215: three-dimensional solid knitted fabric supporting member
215*a*: through-hole for arrangement
216: film
221, 222: plate-shaped expanded body
230: vibration sensor

The invention claimed is:

1. A biological body state analyzing device provided with a state analyzing section which is configured to analyze a time-series waveform of a biological signal obtained from an upper body of a person by a biological signal measuring device to analyze a state of the person, wherein the state analyzing section comprises:
   a frequency computing means for obtaining a time-series waveform of a frequency in the time-series waveform of the biological signal;
   a frequency slope time-series analyzing and computing means for i) setting a predetermined time window in a predetermined overlapped time in the time-series waveform of the frequency of the biological signal obtained by the frequency computing means; ii) performing movement calculation for obtaining a slope of the frequency for each predetermined time window set in the predetermined overlapped time in the time-series waveform of the frequency of the biological signal obtained by the frequency computing means; and iii) outputting a time series change of the slope of the frequency obtained for each time window as a frequency slope time-series waveform;
   a frequency fluctuation time-series analyzing and computing means for i) setting a predetermined time window in a predetermined overlapped time in the time-series waveform of the frequency of the biological signal obtained by the frequency computing means; ii) performing movement calculation for obtaining a mean value of the frequency for each predetermined time window set in the predetermined overlapped time in the time-series waveform of the frequency of the biological signal obtained by the frequency computing means; and iii) outputting a time series change of the mean value of the frequency obtained for each time window as a frequency fluctuation time-series waveform; and
   a waveform determining means for analyzing the frequency slope time-series waveform obtained by the frequency slope time-series analyzing and computing means, the frequency fluctuation time-series waveform obtained by the frequency fluctuation time-series analyzing and computing means, and a state of change of a base line of the frequency fluctuation time-series waveform, thereby making determination.

2. The biological body state analyzing device according to claim 1, further comprising:
   a base line computing means for outputting a base line of the frequency fluctuation time-series waveform,
   wherein the frequency fluctuation time-series analyzing and computing means is configured to generate a fluctuation waveform steep gradient portion indicating a steep gradient change in the frequency fluctuation time-series waveform,
   wherein the waveform determining means includes a sleep-onset point determining means for determining a terminal point of the fluctuation waveform steep gradient portion as sleep-onset point, when the fluctuation waveform steep gradient portion emerges, a position of a base line of the frequency fluctuation time-series waveform thereafter does not return to the position of the base line of the frequency fluctuation time-series waveform before emergence of the fluctuation waveform steep gradient portion, both an amplitude of the frequency fluctuation time-series waveform and an amplitude of the frequency slope time-series waveform after emergence of the fluctuation waveform steep gradient portion are smaller than the amplitude of the frequency fluctuation time-series waveform and the amplitude of the frequency slope time-series waveform before emergence of the fluctuation waveform steep gradient portion, and the base line of the frequency fluctuation time-series waveform after emergence of the fluctuation waveform steep gradient portion is downward sloping.

3. The biological body state analyzing device according to claim 2, further comprising:
   data storing means for storing teaching data of a sleepiness state leading to sleep onset,
   wherein the sleep-onset point determining means performs comparison with the teaching data of a sleepiness state leading to sleep onset, and the frequency fluctuation time-series waveform and the frequency slope time-series waveform at an occurrence time of the sleep-onset point, which are preliminarily measured, to determine emergence of the fluctuation waveform steep gradient portion.

4. The biological body state analyzing device according to claim 2, wherein the waveform determining means further includes a sleepiness waveform determining means which, when a slope line of the fluctuation waveform steep gradient portion obtained by the frequency fluctuation time-series analyzing and computing means is substantially parallel to a slope line of a slope waveform steep gradient portion in the frequency slope time-series waveform immediately before emergence of the fluctuation waveform steep gradient portion, determines a waveform at that time as a sleepiness state.

5. The biological body state analyzing device according to claim 4, wherein the sleepiness waveform determining means performs comparison with teaching data of a sleepiness state leading to sleep onset, and the frequency fluctuation time-series analysis waveform and the frequency slope time-series analysis waveform at an occurrence time of the sleep-onset point, which are preliminarily measured, to determine emergences of the fluctuation waveform steep gradient portion and the slope waveform steep gradient portion.

6. The biological body state analyzing device according to claim 1, wherein the waveform determining means further includes a fatigue state estimating means for comparing the frequency slope time-series waveform obtained from the frequency slope time-series analyzing and computing means and the frequency fluctuation time-series waveform obtained from the frequency fluctuation time-series analyzing and computing means, to estimate a fatigue state from a degree of a difference between both the waveforms.

7. The biological body state analyzing device according to claim 6, wherein the fatigue state estimating means includes a means for determining a case where the frequency fluctuation time-series waveform transitions with an approximately equal amplitude at an approximately equal frequency while involving a predetermined phase delay relative to the frequency slope time-series waveform as a fatigue-free well state and estimates a fatigue state in a stepwise fashion according to whether or not a predetermined or more change occurs from the well state regarding at least one item of an initial phase angle, a phase difference, an amplitude, and an angular frequency.

8. The biological body state analyzing device according to claim 6, wherein the fatigue state estimating means converts the frequency slope time-series waveform and the frequency fluctuation time-series waveform into sinusoidal models of a single harmonic motion, respectively, to perform estimation of the fatigue state between both the sinusoidal models.

9. The biological body state analyzing device according to claim 6, wherein the fatigue state estimating means converts the frequency slope time-series waveform and the frequency fluctuation time-series waveform into sinusoidal models of a single harmonic motion, then synthesizes both the sinusoidal models to obtain a synthesized wave, compares the synthesized wave thus obtained with a synthesized wave obtained in a fatigue-free well state to perform estimation of a fatigue state.

10. The biological body state analyzing device according to claim 1, wherein the frequency computing means includes at least one of a means for smoothing-differentiating the time-series waveform of the biological signal to obtain a maximum value and obtain a time-series waveform of the frequency of the biological signal using the maximum value, and a means for obtaining a zero-crossing point at which a positive value changes to a negative value in the time-series waveform of the biological signal and obtains a time-series waveform of the frequency of the biological signal using the zero-crossing point.

11. The biological body state analyzing device according to claim 1, wherein
the frequency computing means includes:
a first frequency computing means for smoothing-differentiating the time-series waveform of the biological signal to obtain a maximum value and obtain a time-series waveform of the frequency of the biological signal using the maximum value; and
a second frequency computing means for obtaining a zero-crossing point at which a positive value changes to a negative value in the time-series waveform of the biological signal and for obtaining a time-series waveform of the frequency of the biological signal using the zero-crossing point;
the frequency slope time-series analyzing and computing means includes:
a first frequency slope time-series analyzing and computing means for i) setting a predetermined time window in a predetermined overlapped time in the time-series waveform of the frequency of the biological signal obtained by the first frequency computing means; ii) performing movement calculation for obtaining a slope of the frequency for each predetermined time window set in the predetermined overlapped time in the time-series waveform of the frequency of the biological signal obtained by the first frequency computing means; and iii) outputting a time series change of the slope of the frequency obtained for each time window as a frequency slope time-series waveform; and
a second frequency slope time-series analyzing and computing means for i) setting a predetermined time window in a predetermined overlapped time in the time-series waveform of the frequency of the biological signal obtained by the second frequency computing means; ii) performing movement calculation for obtaining a slope of the frequency for each predetermined time window set in the predetermined overlapped time in the time-series waveform of the frequency of the biological signal obtained by the second frequency computing means; and iii) outputting a time series change of the slope of the frequency obtained for each time window as a frequency slope time-series waveform; and
the waveform determining means includes:
a first integral curve computing means for applying absolute value processing to the frequency slope time-series waveform obtained by the first frequency slope time-series analyzing and computing means to integrate the same and obtain a first integral curve;
a second integral curve computing means for applying absolute value processing to the frequency slope time-series waveform obtained by the second frequency slope time-series analyzing and computing means to integrate the same and obtain a second integral curve; and
an integral curve determining means for comparing the respective integral curves obtained by the first integral curve computing means and the second integral curve computing means, respectively, with each other.

12. The biological body state analyzing device according to claim 11, wherein the integral curve determining means determines a state of a person from shape patterns of the respective integral curves.

13. The biological body state analyzing device according to claim 1, wherein the biological signal measuring device is configured to be disposed corresponding to a dorsal region of a person and is for detecting a time-series waveform of a biological signal due to movement of an atrium and fluctuation of an aorta obtained through the dorsal region, and the state analyzing section is for analyzing a state of a person using the time-series waveform of the biological signal.

14. A non-transitory computer program configuring a state analyzing section provided in a storage section of a biological body state analyzing device which analyzes a time-series waveform of a biological signal obtained from an upper body of a person by a biological signal measuring device to analyze a state of the person, wherein the computer program comprises:
a frequency calculating step of obtaining a time-series waveform of a frequency in a time-series waveform of the biological signal;
a frequency slope time-series analyzing and computing step of setting a predetermined time window in a predetermined overlapped time in the time-series waveform of the frequency of the biological signal obtained by the frequency computing step; performing movement calculation for obtaining a slope of the frequency for each predetermined time window set in the predetermined overlapped time in the time-series waveform of the frequency of the biological signal obtained by the frequency computing step; and outputting a time series change of the slope of the frequency obtained for each time window as a frequency slope time-series waveform;
a frequency fluctuation time-series analyzing and computing step of setting a predetermined time window in a predetermined overlapped time in the time-series waveform of the frequency of the biological signal obtained by the frequency computing step; performing movement calculation for obtaining a mean value of the frequency for each predetermined time window set in the predetermined overlapped time in the time-series waveform of the frequency of the biological signal obtained by the frequency computing step; and outputting a time series change of the mean value of the frequency obtained for each time window as a frequency fluctuation time-series waveform; and a waveform determining step of analyzing the frequency slope time-series waveform obtained at the frequency slope time-series analyzing and computing step, the frequency fluctuation time-series waveform obtained at the frequency fluctuation time-series analyzing and computing step, and a state of change of a base line of the frequency fluctuation time-series waveform, thereby making determination.

15. The non-transitory computer program according to claim 14, further comprising:

a base line computing step of outputting a base line of the frequency fluctuation time-series waveform, wherein the frequency fluctuation time-series analyzing and computing step generates a fluctuation waveform steep gradient portion indicating a steep gradient change in the frequency fluctuation time-series waveform, wherein the waveform determining step includes a sleep-onset point determining step of determining a terminal point of the fluctuation waveform steep gradient portion as a sleep-onset point when, the fluctuation waveform steep gradient portion emerges, a position of a base line of the frequency fluctuation time-series waveform thereafter does not return to the position of the base line of the frequency fluctuation time-series waveform before emergence of the fluctuation waveform steep gradient portion, both an amplitude of the frequency fluctuation time-series waveform and an amplitude of frequency slope time-series waveform after emergence of the fluctuation waveform steep gradient portion are smaller than the amplitude of the frequency fluctuation time-series waveform and the amplitude of the frequency slope time-series waveform before emergence of the fluctuation waveform steep gradient portion, and the base line of the frequency fluctuation time-series waveform after emergence of the fluctuation waveform steep gradient portion is downward sloping.

16. The non-transitory computer program according to claim 15, further comprising:

data storing step of storing teaching data of a sleepiness state leading to sleep onset, wherein the sleep-onset point determining step performs comparison with the teaching data of a sleepiness state leading to sleep onset, and the frequency fluctuation time-series waveform and the frequency slope time-series waveform at an occurrence time of the sleep-onset point, which are preliminarily measured, to determine emergence of the fluctuation waveform steep gradient portion.

17. The non-transitory computer program according to claim 15, wherein the waveform determining step further includes a sleepiness waveform determining step of, when a slope line of the fluctuation waveform steep gradient portion obtained at the frequency fluctuation time-series analyzing and computing step is substantially parallel to a slope line of a slope waveform steep gradient portion in the frequency slope time-series waveform immediately before emergence of the fluctuation waveform steep gradient portion, determining a waveform at that time as a sleepiness state.

18. The non-transitory computer program according to claim 17, wherein the sleepiness waveform determining step performs comparison with teaching data of a sleepiness state leading to sleep onset, and the frequency fluctuation time-series waveform and the frequency slope time-series waveform at an occurrence time of the sleep-onset point, which are preliminarily measured, to determine emergences of the fluctuation waveform steep gradient portion and the slope waveform steep gradient portion.

19. The non-transitory computer program according to claim 14, wherein the waveform determining step further includes a fatigue state estimating step of comparing the frequency slope time-series waveform obtained from the frequency slope time-series analyzing and computing step and the frequency fluctuation time-series waveform obtained from the frequency fluctuation time-series analyzing and computing step, to estimate a fatigue state from a degree of a difference between the both waveforms.

20. The non-transitory computer program according to claim 19, wherein the fatigue state estimating step includes a means for determining a case where the frequency fluctuation time-series waveform transitions with an approximately equal amplitude at an approximately equal frequency while involving a predetermined phase delay relative to the frequency slope time-series waveform as a fatigue-free well state and estimating a fatigue state in a stepwise fashion according to whether or not a predetermined or more change occurs from the well state regarding at least one item of an initial phase angle, a phase difference, an amplitude, and an angular frequency.

21. The non-transitory computer program according to claim 19, wherein the fatigue state estimating step converts the frequency slope time-series waveform and the frequency fluctuation time-series waveform into sinusoidal models of a single harmonic motion, respectively, to perform estimation of the fatigue state between both the sinusoidal models.

22. The non-transitory computer program according to claim 19, wherein the fatigue state estimating step converts the frequency slope time-series waveform and the frequency fluctuation time-series waveform into sinusoidal models of a single harmonic motion, then synthesizes both the sinusoidal models to obtain a synthesized wave, compares the synthesized wave thus obtained with a synthesized wave obtained in a fatigue-free well state to perform estimation of a fatigue state.

23. The non-transitory computer program according to claim 14, wherein the frequency calculating step includes at least one of a step which smoothing-differentiates the time-series waveform of the biological signal to obtain a maximum value and obtain a time-series waveform of the frequency of the biological signal using the maximum value, and a step which obtains a zero-crossing point at which a positive value changes to a negative value in the time-series waveform of the biological signal and obtains a time-series waveform of the frequency of the biological signal using the zero-crossing point.

24. The non-transitory computer program according to claim 14, wherein the frequency computing step includes a first frequency computing step of smoothing-differentiating the time-series waveform of the biological signal to obtain a maximum value and obtain a time-series waveform of the frequency of the biological signal using the maximum value and a second frequency computing step of obtaining a zero-crossing point at which a positive value changes to a negative value in the time-series waveform of the biological signal and obtaining a time-series waveform of the frequency of the biological signal using the zero-crossing point;

the frequency slope time-series analyzing and computing step includes a first frequency slope time-series analyzing and computing step of performing movement calculation for obtaining a slope of the frequency for each predetermined time window set in a predetermined overlapped time in the time-series waveform of the frequency of the biological signal obtained by the first frequency computing means and outputting a time series change of the slope of the frequency obtained for each time window as a frequency slope time-series waveform, and a second frequency slope time-series analyzing and computing step of performing movement calculation for obtaining a slope of the frequency for each predetermined time window set in a predetermined overlapped time in the time-series waveform of the frequency of the biological signal obtained by the second frequency computing step and outputting a time series change of the slope of the frequency obtained for each time window as a frequency slope time-series waveform; and the waveform determining step includes a first integral curve computing step of applying absolute value processing to the frequency slope time-series waveform obtained by the first frequency slope time-series analyzing and computing step to integrate the same and obtain a first integral curve, a second integral curve computing step of applying absolute value processing to the frequency slope time-series waveform obtained by the second frequency slope time-series analyzing and computing step to integrate the same and obtain a second integral curve, and an integral curve determining step of comparing the respective integral curves obtained by the first integral curve computing step and the second integral curve computing step, respectively, with each other.

25. The non-transitory computer program according to claim 24, wherein the integral curve determining step determines a state of a person from shape patterns of the respective integral curves.

* * * * *